US012637494B2

(12) United States Patent
Yoshii et al.

(10) Patent No.: US 12,637,494 B2
(45) Date of Patent: May 26, 2026

(54) METHOD FOR PRODUCING PEPTIDE CONTAINING NON-NATURAL AMINO ACID

(71) Applicant: CHUGAI SEIYAKU KABUSHIKI KAISHA, Tokyo (JP)

(72) Inventors: Sakiko Yoshii, Kamakura (JP); Koichiro Shimomura, Kamakura (JP); Sou Ishino, Kamakura (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 1015 days.

(21) Appl. No.: 17/783,076

(22) PCT Filed: Dec. 11, 2020

(86) PCT No.: PCT/JP2020/046213

§ 371 (c)(1),
(2) Date: Jun. 7, 2022

(87) PCT Pub. No.: WO2021/117848

PCT Pub. Date: Jun. 17, 2021

(65) Prior Publication Data

US 2023/0069218 A1 Mar. 2, 2023

(30) Foreign Application Priority Data

Dec. 12, 2019 (JP) ................................ 2019-224297

(51) Int. Cl.

| | |
|---|---|
| ***C07K 14/245*** | (2006.01) |
| ***C12N 15/10*** | (2006.01) |
| ***C12N 15/11*** | (2006.01) |

(52) U.S. Cl.

CPC ........ *C07K 14/245* (2013.01); *C12N 15/1062* (2013.01); *C12N 15/11* (2013.01)

(58) Field of Classification Search

None

See application file for complete search history.

(56) References Cited

U.S. PATENT DOCUMENTS

| | | | |
|---|---|---|---|
| 5,556,768 | A | 9/1996 | Yamashita |
| 9,409,952 | B2 | 8/2016 | Kariyuki et al. |
| 10,815,489 | B2 | 10/2020 | Ohta et al. |
| 11,891,457 | B2 | 2/2024 | Kariyuki et al. |
| 12,163,134 | B2 | 12/2024 | Ohta et al. |
| 2006/0008871 | A1 | 1/2006 | Chumpolkulwong et al. |
| 2015/0080549 | A1 | 3/2015 | Kariyuki et al. |
| 2016/0311858 | A1 | 10/2016 | Kariyuki et al. |
| 2018/0127761 | A1 | 5/2018 | Ohta et al. |
| 2019/0338050 | A1 | 11/2019 | Nakano et al. |
| 2020/0040039 | A1 | 2/2020 | Inoue et al. |
| 2020/0040372 | A1 | 2/2020 | Tanaka et al. |
| 2020/0131669 | A1 | 4/2020 | Muraoka et al. |
| 2021/0061860 | A1 | 3/2021 | Kariyuki et al. |
| 2021/0087572 | A1 | 3/2021 | Ohta et al. |
| 2022/0205009 | A1 | 6/2022 | Shinohara et al. |
| 2023/0096766 | A1 | 3/2023 | Muraoka et al. |
| 2023/0108274 | A1 | 4/2023 | Kagotani et al. |
| 2024/0052340 | A1 | 2/2024 | Nishimura et al. |
| 2024/0166689 | A1 | 5/2024 | Kariyuki et al. |
| 2025/0051784 | A1 | 2/2025 | Ohta et al. |

FOREIGN PATENT DOCUMENTS

| | | | |
|---|---|---|---|
| CN | 101535338 | A | 9/2009 |
| CN | 102827827 | A | 12/2012 |
| EP | 2615455 | B1 | 11/2017 |
| JP | H078289 | A | 1/1995 |
| JP | 2004173627 | A | 6/2004 |
| WO | WO2006110182 | A2 | 10/2006 |
| WO | WO2008073184 | A2 | 6/2008 |
| WO | WO2013100132 | A1 | 7/2013 |
| WO | WO2016148044 | A1 | 9/2016 |
| WO | WO2017150732 | A1 | 9/2017 |
| WO | WO2018143145 | A1 | 8/2018 |
| WO | WO2018174078 | A1 | 9/2018 |
| WO | WO2018225864 | A1 | 12/2018 |
| WO | WO2020122182 | A1 | 6/2020 |
| WO | WO2020138336 | A1 | 7/2020 |
| WO | WO2021132546 | A1 | 7/2021 |
| WO | WO2021261577 | A1 | 12/2021 |

OTHER PUBLICATIONS 50S ribosomal protein L31 from Citrobacter koseri A0A3S41763, deposited Apr. 2019; retrieved from < https://www.uniprot.org/uniprotkb/A0A3S41763/entry > on Jun. 9, 2025.*

Chadani, Y., et al., "Intrinsic Ribosome Destabilization Underlies Translation and Provides an Organism with a Strategy of Environmental Sensing," Mol Cell, 68(3), 528-539 (2017).

Du, F., et al., "On the Modification of Proteins by Unnatural Amino Acids," Journal of Hangzhou Normal University (Natural Science Edition), 12(5):437-445 (2013), with partial English translation.

Hartman, M. C. T., et al., "An Expanded Set of Amino Acid Analogs for the Ribosomal Translation of Unnatural Peptides," PLoS ONE, 2(10):e972 (2007).

Jing, J., "A Cell-Free Translational System for Mutant Prourokinase," Journal of Beijing Normal University (Natural Science), College of Life Sciences, Beijing Key Laboratory of Genetic Engineering Drugs and Biotechnology: Beijing Normal University, 100875, Beijing, China, 44(2):185-187 (2008), with partial English translation.

Josephson, K., et al., "Ribosomal Synthesis of Unnatural Peptides," J Am Chem Soc., 127(33):11727-11735 (2005).

Lilleorg, S., et al., "The Intersubunit Bridge B1b of the Bacterial Ribosome Facilitates Initiation of Protein Synthesis and Maintenance of Translational Fidelity," J Mol Biol., 429(7), 1067-1080 (2017).

(Continued)

*Primary Examiner* — Suzanne M Noakes

(74) *Attorney, Agent, or Firm* — Nixon & Vanderhye P.C.

(57) ABSTRACT

The present invention revealed that translating an mRNA that encodes a peptide containing an unnatural amino acid in a translation system that contains a ribosome containing an engineered L31 protein can increase the amount of the translated peptide. Furthermore, the invention revealed that by using this ribosome, the relative amount of by-products can also be reduced. An engineered L31 protein of the present invention has an amino acid sequence with deletion of 6 or more amino acid residues from the C terminus in the amino acid sequence of the wild-type *Escherichia coli* L31 protein.

5 Claims, 3 Drawing Sheets

Specification includes a Sequence Listing.

(56) References Cited

OTHER PUBLICATIONS

Maini, R., "Ribosome-mediated synthesis of natural product-like peptides via cell-free translation," Curr Opin Chem Biol., 34:44-52 (2016).
Singh-Blom, A., et al., "An amino acid depleted cell-free protein synthesis system for the incorporation of non-canonical amino acid analogs into proteins," Journal of Biotechnology, 178:12-22 (2014).
Ueda, M., et al., "A translation activity of *Escherichia coli* ribosome is 40% higher than a conventional measured value—Effects of L31 protein damage are excluded," Abstracts of the 39th Annual Conference of the Molecular Biology Society of Japan, 39, abstract No. 3P-0236 (2016).
Ueta, M. et al., "Ribosomal protein L31 in *Escherichia coli* contributes to ribosome subunit association and translation, whereas short L31 cleaved by protease 7 reduces both activities," Genes to Cells, 22:452-471 (2017).
"UniprotKB-A0A377B8T0 (A0A377B8T0_ECOLX)," UniProt [online], [retrieved on Jan. 14, 2021] (2018).
Wada, A., et al., "The Discovery of Ribosomal Protein bL31 from *Escherichia coli*: A Long Story Revisited," Int J Mol Sci., 24(4):3445 (2023).
Zhang, M., et al., "Research progress and applications of cell-free protein synthesis system," Chinese Bulletin of Life Sciences, College of Life Science, Shandong Normal University, Jinan 250014, China, 30(1):95-99 (2018), with partial English translation.
U.S. Appl. No. 14/368,564, filed Jun. 25, 2014, Kariyuki et al., related application.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/479,736, filed Jul. 22, 2019, Tanaka et al., related application.
U.S. Appl. No. 16/619,014, filed Dec. 3, 2019, Muraoka et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/787,809, filed Jun. 21, 2022, Kagotani et al., related application.
U.S. Appl. No. 18/010,608, filed Dec. 19, 2023, Nishimura et al., related application.
U.S. Appl. No. 18/460,300, filed Sep. 1, 2023, Kariyuki et al., related application.
U.S. Appl. No. 18/926,665, filed Oct. 25, 2024, Ohta et al., related application.

* cited by examiner

SEQUENCE LISTING

<160> NUMBER OF SEQ ID NOS: 49

<210> SEQ ID NO 1
<211> LENGTH: 70
<212> TYPE: PRT
<213> ORGANISM: Escherichia coli

<400> SEQUENCE: 1

Met Lys Lys Asp Ile His Pro Lys Tyr Glu Glu Ile Thr Ala Ser Cys
1 5 10 15

Ser Cys Gly Asn Val Met Lys Ile Arg Ser Thr Val Gly His Asp Leu
20 25 30

Asn Leu Asp Val Cys Ser Lys Cys His Pro Phe Phe Thr Gly Lys Gln
35 40 45

Arg Asp Val Ala Thr Gly Gly Arg Val Asp Arg Phe Asn Lys Arg Phe
50 55 60

Asn Ile Pro Gly Ser Lys
65 70

<210> SEQ ID NO 2
<211> LENGTH: 62
<212> TYPE: PRT
<213> ORGANISM: Artificial Sequence
<220> FEATURE:
<223> OTHER INFORMATION: L31 short

<400> SEQUENCE: 2

Met Lys Lys Asp Ile His Pro Lys Tyr Glu Glu Ile Thr Ala Ser Cys
1 5 10 15

Ser Cys Gly Asn Val Met Lys Ile Arg Ser Thr Val Gly His Asp Leu
20 25 30

-continued

```
Asn Leu Asp Val Cys Ser Lys Cys His Pro Phe Phe Thr Gly Lys Gln
        35                  40                  45

Arg Asp Val Ala Thr Gly Gly Arg Val Asp Arg Phe Asn Lys
    50                  55                  60


<210> SEQ ID NO 3
<211> LENGTH: 72
<212> TYPE: DNA
<213> ORGANISM: Artificial Sequence
<220> FEATURE:
<223> OTHER INFORMATION: An artificially synthesized nucleotide sequence

<400> SEQUENCE: 3

atataaaaaa tacatattca atcattaaaa cgattgaatg gagaactttt aattaaccct     60

cactaaaggg cg                                                          72


<210> SEQ ID NO 4
<211> LENGTH: 73
<212> TYPE: DNA
<213> ORGANISM: Artificial Sequence
<220> FEATURE:
<223> OTHER INFORMATION: An artificially synthesized nucleotide sequence

<400> SEQUENCE: 4

agttattccc cggggcgatt ttcacctcgg ggaaatttta gttggcgttc taatacgact     60

cactataggg ctc                                                         73


<210> SEQ ID NO 5
<211> LENGTH: 68
<212> TYPE: DNA
<213> ORGANISM: Artificial Sequence
<220> FEATURE:
<223> OTHER INFORMATION: An artificially synthesized nucleotide sequence

<400> SEQUENCE: 5

tggcaaacag cgtgatgttg ctaccggtgg ccgtgttgac cgcttcaaca agtaaccctc     60

actaaagg                                                               68


<210> SEQ ID NO 6
<211> LENGTH: 68
<212> TYPE: DNA
<213> ORGANISM: Artificial Sequence
<220> FEATURE:
<223> OTHER INFORMATION: An artificially synthesized nucleotide sequence

<400> SEQUENCE: 6

caggcacaaa aaaagcgccg tgcggcgctt ttttcggaaa tccggtctta taatacgact     60

cactatag                                                               68


<210> SEQ ID NO 7
<211> LENGTH: 74
<212> TYPE: RNA
<213> ORGANISM: Artificial Sequence
<220> FEATURE:
<223> OTHER INFORMATION: An artificially synthesized nucleotide sequence

<400> SEQUENCE: 7

guccccuucg ucuagaggcc caggacaccg cccucuuacg gcgguaacag ggguucgaau     60

ccccuagggg acgc                                                        74


<210> SEQ ID NO 8
<211> LENGTH: 74
```

<212> TYPE: RNA
<213> ORGANISM: Artificial Sequence
<220> FEATURE:
<223> OTHER INFORMATION: An artificially synthesized nucleotide sequence

<400> SEQUENCE: 8
guccccuucg ucuagaggcc caggacaccg cccucugacg gcgguaacag ggguucgaau 60
ccccuagggg acgc 74

<210> SEQ ID NO 9
<211> LENGTH: 75
<212> TYPE: RNA
<213> ORGANISM: Artificial Sequence
<220> FEATURE:
<223> OTHER INFORMATION: An artificially synthesized nucleotide sequence

<400> SEQUENCE: 9
ggcggggugg agcagccugg uagcucgucg ggcucauaac ccgaagaucg ucgguucaaa 60
uccggccccc gcaac 75

<210> SEQ ID NO 10
<211> LENGTH: 67
<212> TYPE: RNA
<213> ORGANISM: Artificial Sequence
<220> FEATURE:
<223> OTHER INFORMATION: An artificially synthesized nucleotide sequence

<400> SEQUENCE: 10
ggguuaacuu uaauaaggag auauaaauau gcaguuuauu auugguuuua agauuauucc 60
gauuggu 67

<210> SEQ ID NO 11
<211> LENGTH: 67
<212> TYPE: RNA
<213> ORGANISM: Artificial Sequence
<220> FEATURE:
<223> OTHER INFORMATION: An artificially synthesized nucleotide sequence

<400> SEQUENCE: 11
ggguuaacuu uaauaaggag auauaaauau gacuuuuauu auugguuuua agauuauucc 60
gauuggu 67

<210> SEQ ID NO 12
<211> LENGTH: 85
<212> TYPE: DNA
<213> ORGANISM: Artificial Sequence
<220> FEATURE:
<223> OTHER INFORMATION: An artificially synthesized nucleotide sequence

<400> SEQUENCE: 12
gtaatacgac tcactatagg gttaacttta ataaggagat ataaatatgc agtttattat 60
tggttttaag attattccga ttggt 85

<210> SEQ ID NO 13
<211> LENGTH: 85
<212> TYPE: DNA
<213> ORGANISM: Artificial Sequence
<220> FEATURE:
<223> OTHER INFORMATION: An artificially synthesized nucleotide sequence

<400> SEQUENCE: 13
gtaatacgac tcactatagg gttaacttta ataaggagat ataaatatga cttttattat 60
tggttttaag attattccga ttggt 85

<210> SEQ ID NO 14
<211> LENGTH: 13
<212> TYPE: PRT
<213> ORGANISM: Artificial Sequence
<220> FEATURE:
<223> OTHER INFORMATION: iRT peptide
<220> FEATURE:
<221> NAME/KEY: MISC_FEATURE
<222> LOCATION: (1)..(1)
<223> OTHER INFORMATION: Xaa = Acbz-MeCys(StBu)
<220> FEATURE:
<221> NAME/KEY: MISC_FEATURE
<222> LOCATION: (2)..(2)
<223> OTHER INFORMATION: Xaa = MeSer(tBuOH)
<220> FEATURE:
<221> NAME/KEY: MISC_FEATURE
<222> LOCATION: (3)..(3)
<223> OTHER INFORMATION: Xaa = MePhe
<220> FEATURE:
<221> NAME/KEY: MISC_FEATURE
<222> LOCATION: (7)..(7)
<223> OTHER INFORMATION: Xaa = MePhe
<220> FEATURE:
<221> NAME/KEY: MISC_FEATURE
<222> LOCATION: (8)..(8)
<223> OTHER INFORMATION: Xaa = BODIPYFL-4-AMF

<400> SEQUENCE: 14

Xaa Xaa Xaa Ile Ile Gly Xaa Xaa Ile Ile Pro Ile Gly
1 5 10

<210> SEQ ID NO 15
<211> LENGTH: 11
<212> TYPE: PRT
<213> ORGANISM: Artificial Sequence
<220> FEATURE:
<223> OTHER INFORMATION: iRT peptide
<220> FEATURE:
<221> NAME/KEY: MISC_FEATURE
<222> LOCATION: (1)..(1)
<223> OTHER INFORMATION: Xaa = MePhe
<220> FEATURE:
<221> NAME/KEY: MISC_FEATURE
<222> LOCATION: (5)..(5)
<223> OTHER INFORMATION: Xaa = MePhe
<220> FEATURE:
<221> NAME/KEY: MISC_FEATURE
<222> LOCATION: (6)..(6)
<223> OTHER INFORMATION: Xaa = BODIPYFL-4-AMF

<400> SEQUENCE: 15

Xaa Ile Ile Gly Xaa Xaa Ile Ile Pro Ile Gly
1 5 10

<210> SEQ ID NO 16
<211> LENGTH: 13
<212> TYPE: PRT
<213> ORGANISM: Artificial Sequence
<220> FEATURE:
<223> OTHER INFORMATION: iRT peptide
<220> FEATURE:
<221> NAME/KEY: MISC_FEATURE
<222> LOCATION: (1)..(1)
<223> OTHER INFORMATION: Xaa = Acbz-MeCys(StBu)
<220> FEATURE:
<221> NAME/KEY: MISC_FEATURE
<222> LOCATION: (3)..(3)

<223> OTHER INFORMATION: Xaa = MePhe
<220> FEATURE:
<221> NAME/KEY: MISC_FEATURE
<222> LOCATION: (7)..(7)
<223> OTHER INFORMATION: Xaa = MePhe
<220> FEATURE:
<221> NAME/KEY: MISC_FEATURE
<222> LOCATION: (8)..(8)
<223> OTHER INFORMATION: Xaa = BODIPYFL-4-AMF

<400> SEQUENCE: 16

```
Xaa Thr Xaa Ile Ile Gly Xaa Xaa Ile Ile Pro Ile Gly
1               5                   10
```

<210> SEQ ID NO 17
<211> LENGTH: 17
<212> TYPE: PRT
<213> ORGANISM: Artificial Sequence
<220> FEATURE:
<223> OTHER INFORMATION: LCT12

<400> SEQUENCE: 17

```
Phe Thr Ile Phe Pro Gly Phe Ile Ile Thr Thr Gly Thr Gly Thr Gly
1               5                   10                  15

Ala
```

<210> SEQ ID NO 18
<211> LENGTH: 69
<212> TYPE: DNA
<213> ORGANISM: Artificial Sequence
<220> FEATURE:
<223> OTHER INFORMATION: Forward Primer for L31(1-27)

<400> SEQUENCE: 18

```
gaaattactg ctagctgctc ttgcggtaac gtaatgaaaa tccgctccac ctaaccctca     60

ctaaagggc                                                             69
```

<210> SEQ ID NO 19
<211> LENGTH: 69
<212> TYPE: DNA
<213> ORGANISM: Artificial Sequence
<220> FEATURE:
<223> OTHER INFORMATION: Forward Primer for L31(1-32)

<400> SEQUENCE: 19

```
tgctcttgcg gtaacgtaat gaaaatccgc tccaccgttg gtcatgacct gtaaccctca     60

ctaaagggc                                                             69
```

<210> SEQ ID NO 20
<211> LENGTH: 69
<212> TYPE: DNA
<213> ORGANISM: Artificial Sequence
<220> FEATURE:
<223> OTHER INFORMATION: Forward Primer for L31(1-37)

<400> SEQUENCE: 20

```
gtaatgaaaa tccgctccac cgttggtcat gacctgaacc tcgacgtgtg ctaaccctca     60

ctaaagggc                                                             69
```

<210> SEQ ID NO 21
<211> LENGTH: 69
<212> TYPE: DNA
<213> ORGANISM: Artificial Sequence
<220> FEATURE:
<223> OTHER INFORMATION: Forward Primer for L31(1-42)

<400> SEQUENCE: 21
tccaccgttg gtcatgacct gaacctcgac gtgtgcagca agtgccaccc gtaaccctca 60
ctaaagggc 69

<210> SEQ ID NO 22
<211> LENGTH: 69
<212> TYPE: DNA
<213> ORGANISM: Artificial Sequence
<220> FEATURE:
<223> OTHER INFORMATION: Forward Primer for L31(1-47)

<400> SEQUENCE: 22
gacctgaacc tcgacgtgtg cagcaagtgc cacccgttct tcactggcaa ataaccctca 60
ctaaagggc 69

<210> SEQ ID NO 23
<211> LENGTH: 69
<212> TYPE: DNA
<213> ORGANISM: Artificial Sequence
<220> FEATURE:
<223> OTHER INFORMATION: Forward Primer for L31(1-52)

<400> SEQUENCE: 23
gtgtgcagca agtgccaccc gttcttcact ggcaaacagc gtgatgttgc ttaaccctca 60
ctaaagggc 69

<210> SEQ ID NO 24
<211> LENGTH: 69
<212> TYPE: DNA
<213> ORGANISM: Artificial Sequence
<220> FEATURE:
<223> OTHER INFORMATION: Forward Primer for L31(1-57)

<400> SEQUENCE: 24
cacccgttct tcactggcaa acagcgtgat gttgctaccg gtggccgtgt ttaaccctca 60
ctaaagggc 69

<210> SEQ ID NO 25
<211> LENGTH: 69
<212> TYPE: DNA
<213> ORGANISM: Artificial Sequence
<220> FEATURE:
<223> OTHER INFORMATION: Forward Primer for L31(1-67)

<400> SEQUENCE: 25
gttgctaccg gtggccgtgt tgaccgcttc aacaagcgtt tcaacatccc gtaaccctca 60
ctaaagggc 69

<210> SEQ ID NO 26
<211> LENGTH: 68
<212> TYPE: DNA
<213> ORGANISM: Artificial Sequence
<220> FEATURE:
<223> OTHER INFORMATION: Reverse Primer for mutantL31

<400> SEQUENCE: 26
caggcacaaa aaaagcgccg tgcggcgctt ttttcggaaa tccggtctta taatacgact 60
cactatag 68

<210> SEQ ID NO 27

<211> LENGTH: 85
<212> TYPE: DNA
<213> ORGANISM: Artificial Sequence
<220> FEATURE:
<223> OTHER INFORMATION: An artificially synthesized nucleotide sequence

<400> SEQUENCE: 27
gtaatacgac tcactatagg gttaacttta agaaggagat atacatatga ctcagattat 60
tggttttaag attattccga ttggt 85

<210> SEQ ID NO 28
<211> LENGTH: 67
<212> TYPE: RNA
<213> ORGANISM: Artificial Sequence
<220> FEATURE:
<223> OTHER INFORMATION: mR-1

<400> SEQUENCE: 28
ggguuaacuu uaagaaggag auauacauau gacucagauu auugguuuua agauuauucc 60
gauuggu 67

<210> SEQ ID NO 29
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzMeCStBu
<220> FEATURE:
<221> NAME/KEY: MISC_FEATURE
<222> LOCATION: (2)..(2)
<223> OTHER INFORMATION: Xaa = MeG
<220> FEATURE:
<221> NAME/KEY: MISC_FEATURE
<222> LOCATION: (3)..(3)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 29

Xaa Xaa Xaa Ile Ile Gly Xaa Xaa Ile Ile Pro Ile Gly
1 5 10

<210> SEQ ID NO 30
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzMeCStBu
<220> FEATURE:
<221> NAME/KEY: MISC_FEATURE
<222> LOCATION: (2)..(2)
<223> OTHER INFORMATION: Xaa = MeStBuOH
<220> FEATURE:
<221> NAME/KEY: MISC_FEATURE
<222> LOCATION: (3)..(3)
<223> OTHER INFORMATION: Xaa = MeF
<220> FEATURE:

<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 30

```
Xaa Xaa Xaa Ile Ile Gly Xaa Xaa Ile Ile Pro Ile Gly
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzMeCStBu
<220> FEATURE:
<221> NAME/KEY: MISC_FEATURE
<222> LOCATION: (3)..(3)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 31

```
Xaa Leu Xaa Ile Ile Gly Xaa Xaa Ile Ile Pro Ile Gly
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: 1iRT of seq id no. 29
<220> FEATURE:
<221> NAME/KEY: MISC_FEATURE
<222> LOCATION: (1)..(1)
<223> OTHER INFORMATION: Xaa = MeG
<220> FEATURE:
<221> NAME/KEY: MISC_FEATURE
<222> LOCATION: (2)..(2)
<223> OTHER INFORMATION: Xaa = MeF
<220> FEATURE:
<221> NAME/KEY: MISC_FEATURE
<222> LOCATION: (6)..(6)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = Bdp4AMF

<400> SEQUENCE: 32

```
Xaa Xaa Ile Ile Gly Xaa Xaa Ile Ile Pro Ile Gly
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: 1iRT of seq id no. 30
<220> FEATURE:

<221> NAME/KEY: MISC_FEATURE
<222> LOCATION: (1)..(1)
<223> OTHER INFORMATION: Xaa = MeStBuOH
<220> FEATURE:
<221> NAME/KEY: MISC_FEATURE
<222> LOCATION: (2)..(2)
<223> OTHER INFORMATION: Xaa = MeF
<220> FEATURE:
<221> NAME/KEY: MISC_FEATURE
<222> LOCATION: (6)..(6)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = Bdp4AMF

<400> SEQUENCE: 33

Xaa Xaa Ile Ile Gly Xaa Xaa Ile Ile Pro Ile Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 1iRT of seq id no. 31
<220> FEATURE:
<221> NAME/KEY: MISC_FEATURE
<222> LOCATION: (2)..(2)
<223> OTHER INFORMATION: Xaa = MeF
<220> FEATURE:
<221> NAME/KEY: MISC_FEATURE
<222> LOCATION: (6)..(6)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = Bdp4AMF

<400> SEQUENCE: 34

Leu Xaa Ile Ile Gly Xaa Xaa Ile Ile Pro Ile Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: 2iRT of seq id nos. 29-31
<220> FEATURE:
<221> NAME/KEY: MISC_FEATURE
<222> LOCATION: (1)..(1)
<223> OTHER INFORMATION: Xaa = MeF
<220> FEATURE:
<221> NAME/KEY: MISC_FEATURE
<222> LOCATION: (5)..(5)
<223> OTHER INFORMATION: Xaa = MeF
<220> FEATURE:
<221> NAME/KEY: MISC_FEATURE
<222> LOCATION: (6)..(6)
<223> OTHER INFORMATION: Xaa = Bdp4AMF

<400> SEQUENCE: 35

Xaa Ile Ile Gly Xaa Xaa Ile Ile Pro Ile Gly
1               5                   10

<210> SEQ ID NO 36
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:

```
<221> NAME/KEY: MISC_FEATURE
<222> LOCATION: (1)..(1)
<223> OTHER INFORMATION: Xaa = AcbzdMeCStBu
<220> FEATURE:
<221> NAME/KEY: MISC_FEATURE
<222> LOCATION: (2)..(2)
<223> OTHER INFORMATION: Xaa = Nle, S3F5MePyr, SPh2Cl, I, T, or L
<220> FEATURE:
<221> NAME/KEY: MISC_FEATURE
<222> LOCATION: (3)..(3)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 36

Xaa Xaa Xaa Ile Ile Gly Xaa Xaa Ile Ile Pro Ile Gly
1               5                   10


<210> SEQ ID NO 37
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzMeCStBu
<220> FEATURE:
<221> NAME/KEY: MISC_FEATURE
<222> LOCATION: (2)..(2)
<223> OTHER INFORMATION: Xaa =  Nle, MeG, MeF, S3F5MePyr, MeHph,
      MeA3Pyr, SPh2Cl, G, I, T, MeStBuOH, or L
<220> FEATURE:
<221> NAME/KEY: MISC_FEATURE
<222> LOCATION: (3)..(3)
<223> OTHER INFORMATION: Xaa =  MeF
<220> FEATURE:
<221> NAME/KEY: MISC_FEATURE
<222> LOCATION: (7)..(7)
<223> OTHER INFORMATION: Xaa =  MeF
<220> FEATURE:
<221> NAME/KEY: MISC_FEATURE
<222> LOCATION: (8)..(8)
<223> OTHER INFORMATION: Xaa =  Bdp4AMF

<400> SEQUENCE: 37

Xaa Xaa Xaa Ile Ile Gly Xaa Xaa Ile Ile Pro Ile Gly
1               5                   10


<210> SEQ ID NO 38
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzCStBu
<220> FEATURE:
<221> NAME/KEY: MISC_FEATURE
<222> LOCATION: (2)..(2)
<223> OTHER INFORMATION: Xaa = Nle, MeG, MeF, S3F5MePyr, MeHph, MeA3Pyr,
      SPh2Cl, G, I, T, MeStBuOH, or L
<220> FEATURE:
<221> NAME/KEY: MISC_FEATURE
<222> LOCATION: (3)..(3)
<223> OTHER INFORMATION: Xaa = MeF
```

<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 38

Xaa Xaa Xaa Ile Ile Gly Xaa Xaa Ile Ile Pro Ile Gly
1 5 10

<210> SEQ ID NO 39
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = fMet
<220> FEATURE:
<221> NAME/KEY: MISC_FEATURE
<222> LOCATION: (2)..(2)
<223> OTHER INFORMATION: Xaa = Nle, MeG, MeF, S3F5MePyr, Pic(2), MeHph,
MeA3Pyr, SPh2Cl, G, I, T, MeStBuOH, or L
<220> FEATURE:
<221> NAME/KEY: MISC_FEATURE
<222> LOCATION: (3)..(3)
<223> OTHER INFORMATION: Xaa = MeF
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 39

Xaa Xaa Xaa Ile Ile Gly Xaa Xaa Ile Ile Pro Ile Gly
1 5 10

<210> SEQ ID NO 40
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = AcbzMeCStBu
<220> FEATURE:
<221> NAME/KEY: MISC_FEATURE
<222> LOCATION: (3)..(3)
<223> OTHER INFORMATION: Xaa = Nle, MeF, S3F5MePyr, Pic(2), MeHph,
MeA3Pyr, SPh2Cl, G, I, P, T, MeStBuOH, dA, or L
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 40

Xaa Thr Xaa Ile Ile Gly Xaa Xaa Ile Ile Pro Ile Gly
1 5 10

<210> SEQ ID NO 41
<211> LENGTH: 13
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa = fMet
<220> FEATURE:
<221> NAME/KEY: MISC_FEATURE
<222> LOCATION: (3)..(3)
<223> OTHER INFORMATION: Xaa = Nle, MeG, MeF, S3F5MePyr, Pic(2), MeHph, MeA3Pyr, SPh2Cl, G, I, P, T, MeStBuOH, dA, or L
<220> FEATURE:
<221> NAME/KEY: MISC_FEATURE
<222> LOCATION: (7)..(7)
<223> OTHER INFORMATION: Xaa = MeF
<220> FEATURE:
<221> NAME/KEY: MISC_FEATURE
<222> LOCATION: (8)..(8)
<223> OTHER INFORMATION: Xaa = Bdp4AMF

<400> SEQUENCE: 41

```
Xaa Thr Xaa Ile Ile Gly Xaa Xaa Ile Ile Pro Ile Gly
1               5                   10
```

<210> SEQ ID NO 42
<211> LENGTH: 27
<212> TYPE: PRT
<213> ORGANISM: Artificial Sequence
<220> FEATURE:
<223> OTHER INFORMATION: L31(1-27)

<400> SEQUENCE: 42

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr
            20                  25
```

<210> SEQ ID NO 43
<211> LENGTH: 32
<212> TYPE: PRT
<213> ORGANISM: Artificial Sequence
<220> FEATURE:
<223> OTHER INFORMATION: L31(1-32)

<400> SEQUENCE: 43

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30
```

<210> SEQ ID NO 44
<211> LENGTH: 37
<212> TYPE: PRT
<213> ORGANISM: Artificial Sequence
<220> FEATURE:
<223> OTHER INFORMATION: L31(1-37)

<400> SEQUENCE: 44

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys
        35
```

<210> SEQ ID NO 45
<211> LENGTH: 42
<212> TYPE: PRT
<213> ORGANISM: Artificial Sequence
<220> FEATURE:
<223> OTHER INFORMATION: L31(1-42)

<400> SEQUENCE: 45

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys Ser Lys Cys His Pro
        35                  40
```

<210> SEQ ID NO 46
<211> LENGTH: 47
<212> TYPE: PRT
<213> ORGANISM: Artificial Sequence
<220> FEATURE:
<223> OTHER INFORMATION: L31(1-47)

<400> SEQUENCE: 46

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys Ser Lys Cys His Pro Phe Phe Thr Gly Lys
        35                  40                  45
```

<210> SEQ ID NO 47
<211> LENGTH: 52
<212> TYPE: PRT
<213> ORGANISM: Artificial Sequence
<220> FEATURE:
<223> OTHER INFORMATION: L31(1-52)

<400> SEQUENCE: 47

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys Ser Lys Cys His Pro Phe Phe Thr Gly Lys Gln
        35                  40                  45

Arg Asp Val Ala
    50
```

<210> SEQ ID NO 48
<211> LENGTH: 57
<212> TYPE: PRT
<213> ORGANISM: Artificial Sequence
<220> FEATURE:
<223> OTHER INFORMATION: L31(1-57)

<400> SEQUENCE: 48

```
Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys Ser Lys Cys His Pro Phe Phe Thr Gly Lys Gln
        35                  40                  45
```

-continued

```
Arg Asp Val Ala Thr Gly Gly Arg Val
    50                  55


<210> SEQ ID NO 49
<211> LENGTH: 67
<212> TYPE: PRT
<213> ORGANISM: Artificial Sequence
<220> FEATURE:
<223> OTHER INFORMATION: L31(1-67)

<400> SEQUENCE: 49

Met Lys Lys Asp Ile His Pro Lys Tyr Glu Glu Ile Thr Ala Ser Cys
1               5                   10                  15

Ser Cys Gly Asn Val Met Lys Ile Arg Ser Thr Val Gly His Asp Leu
            20                  25                  30

Asn Leu Asp Val Cys Ser Lys Cys His Pro Phe Phe Thr Gly Lys Gln
        35                  40                  45

Arg Asp Val Ala Thr Gly Gly Arg Val Asp Arg Phe Asn Lys Arg Phe
    50                  55                  60

Asn Ile Pro
65
```

METHOD FOR PRODUCING PEPTIDE CONTAINING NON-NATURAL AMINO ACID

CROSS-REFERENCE TO RELATED APPLICATIONS

This application is a U.S. National Phase of PCT Application No. PCT/JP2020/046213, filed Dec. 11, 2020, which claims the benefit of Japanese Patent Application No. 2019-224297, filed Dec. 12, 2019, each of which is incorporated herein by reference in its entirety.

REFERENCE TO SEQUENCE LISTING SUBMITTED ELECTRONICALLY

The content of the electronically submitted sequence listing (Name: 6663_0214 Sequence_Listing.txt; Size: 21,016 bytes; and Date of Creation: Jun. 7, 2022) filed with the application is incorporated herein by reference in its entirety.

TECHNICAL FIELD

The present invention relates to methods for producing peptides comprising unnatural amino acids and libraries comprising the peptides. The present invention also relates to engineered L31 proteins and such for use in these methods.

BACKGROUND ART

Drug discovery methods that involve selecting pharmaceutical candidates from a library of various peptides containing a plurality of unnatural amino acids have been devised recently. In particular, mRNA display libraries etc. of unnatural amino acid-containing peptides that utilize cell-free translation systems are increasingly seen as promising because of their diversity and ease of screening. There are a number of reports on methods for synthesizing unnatural amino acid-containing peptides using a translation system (NPL 1 and NPL 2). However, the efficiency of translational synthesis is low in the methods described in these documents.

In vivo, peptides are synthesized by polymerization of amino acids in accordance with the nucleotide sequence information carried by mRNAs. This peptide synthesis process is called translation. Ribosomes play a central role in the process of translation. In cell-free translation systems used to prepare mRNA display libraries, purified ribosomes are usually added.

The L31 protein is known as a protein constituting the ribosome. The L31 protein is a protein that forms the inter subunit Bridge Bib, and serves to stabilize the associated state between 30S and 50S (70S) (NPL 3).

It is known that the L31 protein is degraded by protease 7 during its purification. Comparison of the activity of ribosomes prepared from a wild-type *Escherichia coli* strain, ribosomes prepared from a protease 7-deficient strain, protease 7 KO, and ribosomes prepared from an L31 protein-deficient strain, L31 KO, reportedly shows that ribosomes prepared from the protease 7-deficient strain have greater activity than ribosomes prepared from the wild-type *Escherichia coli* strain and ribosomes prepared from the L31-deficient strain (NPL 3). Also, ribosomes prepared from an L31-deficient strain have been reported to show a 38% reduction in initiation rate in vivo and a slower rate of 70S formation in vitro (NPL 4). Furthermore, the L31-deficient strain has also been reported to show lowered fidelity (NPL 4). Thus, it was known that in the translation of peptides composed of natural amino acids, ribosomes containing the L31 protein not degraded by protease 7 have greater activity than ribosomes containing the cleaved L31 protein and ribosomes not containing the L31 protein.

CITATION LIST

Non-Patent Literature

[NPL 1] Maini, R., Umemoto, S. & Suga, H. Ribosome-mediated synthesis of natural product-like peptides via cell-free translation. Current opinion in chemical biology 34, 44-52, doi:10.1016/j.cbpa.2016.06.006 (2016).

[NPL 2] Hartman, M. C., Josephson, K., Lin, C. W. & Szostak, J. W. An expanded set of amino acid analogs for the ribosomal translation of unnatural peptides. PloS one 2, e972, doi:10.1371/journal.pone.0000972 (2007).

[NPL 3] Ueta M, Wada C, Bessho Y, Maeda M, Wada A. Genes Cells. 2017 May; 22(5):452-471. doi: 10.1111/gtc.12488. Epub 2017 Apr. 10. Genes Cells. 2017

[NPL 4] Lilleorg S, Reier K, Remme J, Liiv A. J Mol Biol. 2017 Apr. 7; 429(7):1067-1080. doi: 10.1016/j.jmb.2017.02.015. Epub 2017 Feb. 24. J Mol Biol. 2017

[NPL 5] Chadani Y, Niwa T, Izumi T, Sugata N, Nagao A, Suzuki T, Chiba S, Ito K, Taguchi H. Mol Cell. 2017 Nov. 2; 68(3):528-539.e5. doi: 10.1016/j.molcel.2017.10.020. Mol Cell. 2017

SUMMARY OF INVENTION

Technical Problem

In one aspect, an objective of the present invention is to provide efficient methods for producing peptides comprising unnatural amino acids, and provide engineered L31 proteins and ribosomes comprising the same for use in these methods.

Solution to Problem

In producing peptides comprising unnatural amino acids using a translation system, the present inventors examined whether the efficiency of mRNA translation would differ between ribosomes comprising L31 protein not degraded by protease 7 and ribosomes comprising L31 protein cleaved by protease 7. As a result, the present inventors discovered that, when translating mRNA encoding a peptide comprising an unnatural amino acid by the Initiation Suppression (iSP) method, the use of ribosomes comprising the L31 protein cleaved by protease 7 led to an increased amount of the translated target molecule as compared to the use of ribosomes comprising the L31 protein not degraded by protease 7. The inventors also found that the relative amount of by-products can also be reduced by using ribosomes comprising the protease 7-cleaved L31 protein. These results were contrary to the facts previously known in the translation of peptides not comprising unnatural amino acids. Furthermore, the present inventors performed peptide synthesis with various magnesium ion concentrations in the translation system, and revealed that when the magnesium ion concentration is within a certain concentration range, the amount of translation is large and the proportion of by-products is low.

The present invention is based on such findings, and specifically relates to the following:

[1] a method for producing a peptide, comprising a step of translating an mRNA encoding a peptide comprising one or more types of unnatural amino acids in a translation system that comprises a ribosome comprising an engineered L31 protein, wherein the ribosome comprising the engineered L31 protein has greater activity for translation of the peptide comprising the unnatural amino acids, as compared to a ribosome comprising wild-type *Escherichia coli* L31 that comprises the amino acid sequence of SEQ ID NO: 1;

[2] a method for producing a peptide, comprising a step of translating an mRNA encoding a peptide comprising one or more types of unnatural amino acids in a translation system that comprises a ribosome comprising an engineered L31 protein, wherein the engineered L31 protein is selected from the group consisting of the proteins of (1) to (3) below:

(1) a protein comprising an amino acid sequence with deletion of 6 or more amino acid residues from the C terminus in the amino acid sequence set forth in SEQ ID NO: 1;

(2) a protein comprising an amino acid sequence with one or more amino acid insertions, substitutions, deletions, and/or additions in the amino acid sequence of the protein of (1); and (3) a protein comprising an amino acid sequence having 80% or more sequence identity to the amino acid sequence of the protein of (1);

[3] a method for producing a peptide, comprising a step of translating an mRNA encoding a peptide comprising one or more types of unnatural amino acids in a translation system that comprises a ribosome comprising an engineered L31 protein, wherein the engineered L31 protein is selected from the group consisting of the proteins of (1) to (3) below:

(1) a protein consisting of an amino acid sequence with deletion of 6 or more amino acid residues from the C terminus in the amino acid sequence set forth in SEQ ID NO: 1;

(2) a protein consisting of an amino acid sequence with one or more amino acid insertions, substitutions, deletions, and/or additions in the amino acid sequence of the protein of (1);

(3) a protein consisting of an amino acid sequence having 80% or more sequence identity to the amino acid sequence of the protein of (1);

[4] the method of [2] or [3], wherein the amino acid sequence with deletion of 6 or more amino acid residues from the C terminus of (1) is an amino acid sequence with deletion of 8 or more amino acid residues from the C terminus;

[5] the method of [4], wherein the amino acid sequence with deletion of 8 or more amino acid residues from the C terminus in the amino acid sequence set forth in SEQ ID NO: 1 of (1), is an amino acid sequence selected from the group consisting of SEQ ID NOs: 2 and 42 to 48;

[6] the method of any one of [2] to [5], wherein the ribosome comprising the protein of (2) and (3) has greater activity for translation of the peptide comprising the unnatural amino acids, as compared to the ribosome comprising the wild-type *Escherichia coli* L31 that comprises the amino acid sequence of SEQ ID NO: 1;

[7] the method of any one of [2] to [6], wherein the ribosome comprising the protein of (1) has greater activity for translation of the peptide comprising the unnatural amino acids, as compared to the ribosome comprising the wild-type *Escherichia coli* L31 that comprises the amino acid sequence of SEQ ID NO: 1;

[8] the method of any one of [2] to [7], wherein the amino acid sequence with deletion of 6 or more amino acid residues from the C terminus is an amino acid sequence with deletion of 6 to 50 amino acid residues from the C terminus;

[9] the method of any one of [2] to [7], wherein the amino acid sequence with deletion of 6 or more amino acid residues from the C terminus is an amino acid sequence with deletion of 8 to 50 amino acid residues from the C terminus;

[10] the method of any one of [2] to [7], wherein the amino acid sequence with deletion of 6 or more amino acid residues from the C terminus is an amino acid sequence with deletion of 6 to 43 amino acid residues from the C terminus;

[11] the method of any one of [2] to [7], wherein the amino acid sequence with deletion of 6 or more amino acid residues from the C terminus is an amino acid sequence with deletion of 8 to 43 amino acid residues from the C terminus;

[12] the method of any one of [1] to [11], wherein the engineered L31 protein is a protein consisting of an amino acid sequence with deletion of 8 or more amino acid residues from the C terminus in the amino acid sequence set forth in SEQ ID NO: 1;

[13] the method of any one of [1] to [12], wherein the engineered L31 protein is a protein consisting of an amino acid sequence set forth in any one selected from the group consisting of SEQ ID NOs: 2 and 42 to 48;

[14] the method of any one of [1] to [13], wherein the proportion of ribosomes comprising the engineered L31 protein relative to all ribosomes in the translation system is 50% or more;

[15] the method of any one of [1] to [14], wherein the translation system further comprises 2 to 8 mM magnesium ions;

[16] the method of any one of [1] to [15], further comprising a step of cyclizing the peptide;

[17] the method of any one of [1] to [16], wherein the peptide comprises an unnatural amino acid at a position corresponding to its initial amino acid;

[18] the method of any one of [1] to [17], wherein the translation is performed by initiation suppression;

[19] the method of any one of [1] to [18], wherein the initiator tRNA comprised in the translation system is acylated with an unnatural amino acid;

[20] the method of any one of [1] to [19], wherein the activity for translation is evaluated by the percentage of translation products in which amino-acid read-through has occurred relative to all translation products (iRT percentage);

[21] the method of any one of [1] to [20], wherein the activity for translation is evaluated by translation into the peptide of SEQ ID NO: 29 using the template mRNA of SEQ ID NO: 10;

[22] the method of any one of [1] to [21], wherein the iRT percentage of the ribosome comprising the engineered L31 protein is 15% or more lower than the iRT percentage of the ribosome comprising the wild-type *Escherichia coli* L31 that comprises the amino acid sequence of SEQ ID NO:1;

[23] a peptide produced by the method of any one of [1] to [22] or a library comprising peptides produced by the method of any one of [1] to [22];

[24] a method of screening for a peptide that binds to a target substance, comprising steps (a) and (b) below:

(a) contacting a target substance with a peptide obtained by the method of any one of [1] to [22] or a library comprising peptides obtained by the method of any one of [1] to [22], or the peptide or library of [23]; and (b) selecting a peptide that binds to the target substance;

[25] the engineered L31 protein of any one of [2] to [24];

[26] the engineered L31 protein of [25](provided that the L31 protein consisting of the amino acid sequence set forth in SEQ ID NO: 2 is excluded);

[27] an isolated nucleic acid encoding the engineered L31 protein of [25] or [26];

[28] a vector or cell comprising the nucleic acid of [27];

[29] a method for producing a ribosome comprising an engineered L31 protein, comprising steps (a) to (c) below:

(a) culturing the cell of [28];

(b) producing a lysate from culture of the cell; and (c) purifying a ribosome from the lysate;

[30] a method for producing an engineered L31 protein, comprising steps (a) and (b) below:

(a) culturing the cell of [28]; and (b) isolating an expression product from culture of the cell;

[31] a method for producing a ribosome, comprising steps (a) and (b) below:

(a) producing a lysate from a wild-type *Escherichia coli* culture using a French press under a condition where the magnesium ion concentration is 5 mM or less, and (b) purifying a ribosome from the lysate;

[32] a ribosome comprising the engineered L31 protein of [25] or [26];

[33] a composition comprising the ribosome of [32];

[34] the composition of [33], wherein the percentage of ribosomes comprising the engineered L31 protein relative to all ribosomes is 50% or more;

[35] the composition of [33] or [34], further comprising (a) and/or (b) below:

(a) an aminoacyl-tRNA formed by bonding an unnatural amino acid to a tRNA; and (b) an mRNA encoding a peptide comprising one or more types of unnatural amino acids;

[36] the composition of any one of [33] to [35], further comprising an initiator tRNA acylated with an unnatural amino acid; and

[37] a method for producing a cell-free translation system, comprising the steps of:

(a) producing a ribosome by the method of [29] or [31]; and (b) mixing the ribosome and an initiator tRNA acylated with an unnatural amino acid.

Effects of the Invention

The present invention provides efficient methods for producing peptides comprising an unnatural amino acid and libraries comprising the peptides. Furthermore, the present invention provides engineered L31 proteins for use in the methods, and ribosomes comprising them. Peptides comprising an unnatural amino acid and libraries thereof can be efficiently produced by using the methods of the present invention.

Conventionally, it has been suggested that ribosomes comprising the L31 protein cleaved by protease 7 are inferior in activity to ribosomes comprising the uncleaved L31 protein. In light of this fact, it is surprising that the use of ribosomes comprising the engineered L31 protein herein allows efficient translation into peptides comprising an unnatural amino acid.

DESCRIPTION OF EMBODIMENTS

Figure 1:
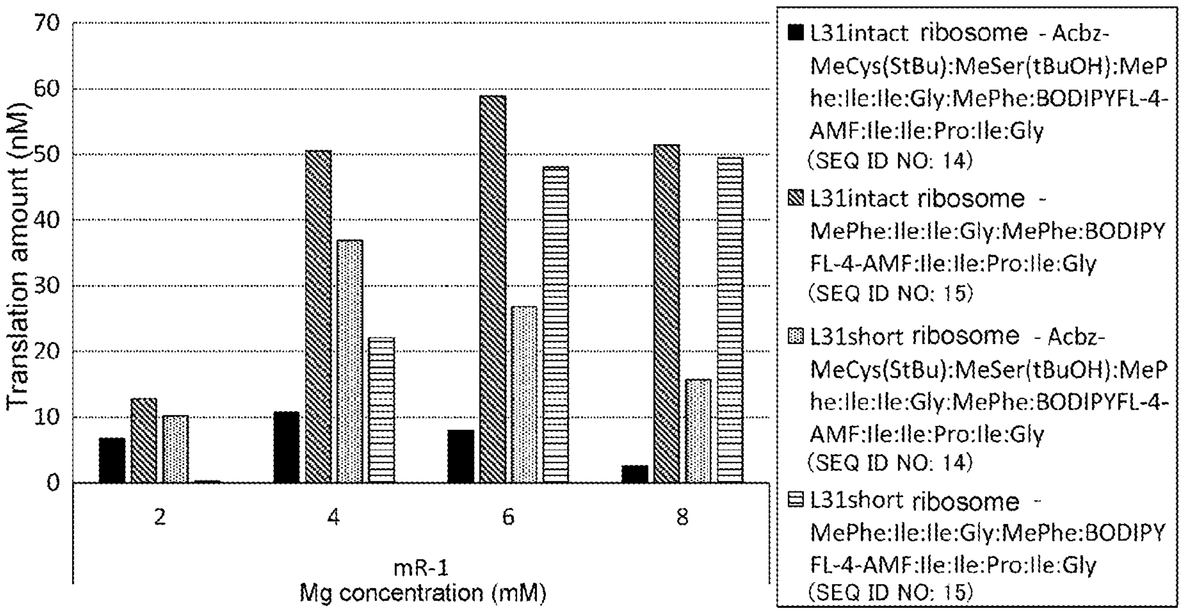
FIG. 1 is a graph showing the amount of translated target molecule and the amount of translated iRT peptide when translating the mR-1 sequence using the L31short ribosome or the L31intact ribosome.
Figure 2:
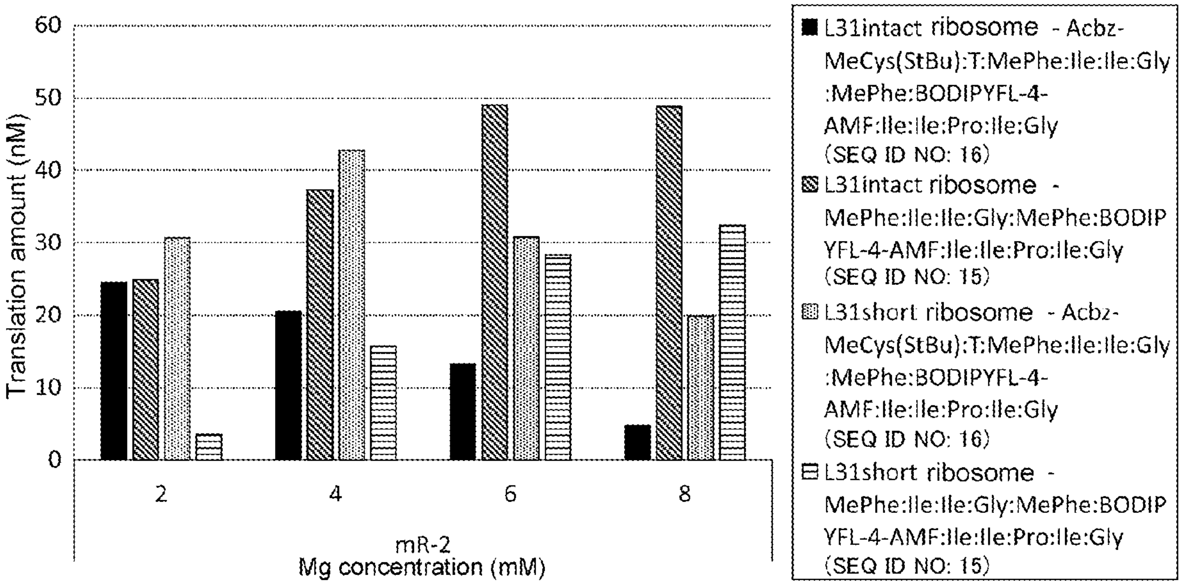
FIG. 2 is a graph showing the amount of translated target molecule and the amount of translated iRT peptide when translating the mR-2 sequence using the L31short ribosome or the L31intact ribosome.
Figure 3:
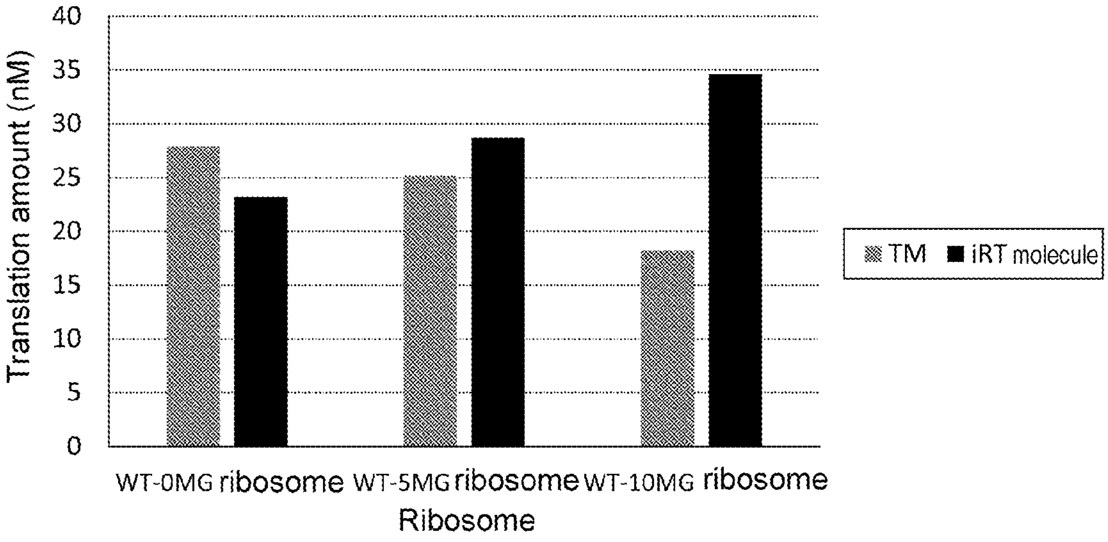
FIG. 3 is a graph showing the amount of translated target molecule and the amount of translated iRT peptide when translating the mR-1 sequence using the WT-0MG ribosome, the WT-5MG ribosome, or the WT-10MG ribosome.

The present invention relates to a method for producing a peptide or a library of peptides, comprising a step of translating an mRNA encoding a peptide comprising one or more types of unnatural amino acids in a translation system that comprises a ribosome comprising an engineered L31 protein. In the present invention, a peptide or a library of peptides can be produced by mixing a translation system that comprises a ribosome comprising an engineered L31 protein with an mRNA encoding the peptide comprising one or more types of unnatural amino acids. Therefore, the present invention relates to a method for producing a peptide or a library of peptides, comprising a step of mixing a translation system that comprises a ribosome comprising an engineered L31 protein with an mRNA encoding the peptide comprising one or more types of unnatural amino acids to translate the mRNA. The production method of the present invention allows efficient translation into peptides comprising an unnatural amino acid as compared with such translation when using ribosomes comprising the wild-type L31 protein having the amino acid sequence of SEQ ID NO: 1 derived from wild-type *Escherichia coli.*

The L31 protein is a protein constituting the ribosome, and plays an important role in the association of the 50S subunit and the 30S subunit. The present inventors discovered that when a peptide comprising one or more types of unnatural amino acids is synthesized in a translation system that comprises a ribosome comprising an engineered L31 protein in which amino acid residues at the C terminus have been deleted from the wild-type L31 protein having the amino acid sequence of SEQ ID NO: 1 derived from wild-type *Escherichia coli*, the amount of translated product increases compared to when the peptide is synthesized in a translation system that comprises a ribosome comprising the wild-type *Escherichia coli* L31 protein. Furthermore, the present inventors discovered that when a translation system that comprises a ribosome comprising an engineered L31 protein is used, the relative amount of by-products generated can also be reduced compared to when a translation system that comprises a ribosome comprising the wild-type *Escherichia coli* L31 protein is used.

Herein, "wild-type *Escherichia coli* L31 protein" refers to L31 having the amino acid sequence of SEQ ID NO: 1, and it may be referred to as "wild-type *Escherichia coli* L31", "intact L31", or "L31intact". Furthermore, herein, "engineered L31 protein" refers to "an engineered protein in which 6 or more amino acid residues have been deleted from the C terminus in the wild-type *Escherichia coli* L31 protein". Herein, among such proteins, "the engineered L31 protein in which the 63rd and subsequent amino acid residues have been deleted from the wild-type *Escherichia coli* L31 protein" or more specifically L31 having the amino acid sequence of SEQ ID NO: 2 may be referred to as "shortL31" or "L31short". Furthermore, "the engineered L31 protein in which the (X+1)th and subsequent amino acid residues have been deleted from the wild-type *Escherichia coli* L31 protein" may be referred to as "L31(1-X)". That is, the above-mentioned shortL31 is also referred to as "L31(1-62)". Furthermore, herein, a ribosome comprising a certain L31 protein may be named with the name of the L31 protein followed by "ribosome"; for example, a ribosome comprising "intact L31", "L31intact", "shortL31", "L31(1-62)", or "L31short" may be referred to as "intactL31 ribosome", "L31intact ribosome", "shortL31 ribosome", "L31(1-62) ribosome", or "L31short ribosome", respectively. Furthermore, a ribosome purified from a wild-type *E. coli* strain may be referred to as a "WT ribosome".

Engineered L31 Proteins

In the production methods of the present disclosure, use of a ribosome comprising an engineered L31 protein allows efficient translation into peptides comprising an unnatural amino acid, as compared to use of a ribosome comprising a wild-type *E. coli* L31. In an embodiment of the present invention, examples of the engineered L31 protein are:

(1) a protein comprising an amino acid sequence with deletion of 6 or more amino acid residues from the C terminus in the amino acid sequence set forth in SEQ ID NO: 1;

(2) a protein comprising an amino acid sequence with one or more amino acid insertions, substitutions, deletions, and/or additions in the amino acid sequence of the protein of (1); and (3) a protein comprising an amino acid sequence having 80% or more sequence identity to the amino acid sequence of the protein of (1).

The protein of (1) above may be a protein comprising an amino acid sequence with deletion of 8 or more amino acid residues or deletion of 9 or more amino acid residues from the C terminus in the amino acid sequence set forth in SEQ ID NO: 1, and examples include proteins comprising an amino acid sequence with deletion of amino acid residues from the C terminus, wherein the number of the deleted amino acid residues ranges from a lower limit selected from 6 residues, 7 residues, 8 residues, 9 residues, 10 residues, 11 residues, 12 residues, and 13 residues, to an upper limit selected from 50 residues, 49 residues, 48 residues, 47 residues, 46 residues, 45 residues, 44 residues, 43 residues, 42 residues, 41 residues, 40 residues, 39 residues, and 38 residues. In one embodiment, examples of the protein of (1) above include proteins comprising an amino acid sequence with deletion of amino acid residues from the C terminus in the amino acid sequence set forth in SEQ ID NO: 1, wherein the number of the deleted amino acid residues is any number included in the range of 6 to 50, 6 to 43, 8 to 50, or 8 to 43. In a further embodiment, examples of the protein of (1) above include proteins comprising the amino acid sequence with deletion of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 27, 38, 39, 40, 41, 42, 43, 44, 45, 46, 47, 48, 49, or 50 amino acid residues from the C terminus in the amino acid sequence set forth in SEQ ID NO: 1. More specifically, the engineered L31 proteins of the present disclosure include proteins comprising the amino acid sequence with deletion of 8, 43, 38, 33, 28, 23, 18, or 13 amino acids from the C terminus in the amino acid sequence set forth in SEQ ID NO: 1, and proteins resulting from alteration (deletion, substitution, and/or insertion) of amino acid residues in these proteins. More specifically, the engineered L31 proteins of the present disclosure also include, (1) a protein comprising an amino acid sequence set forth in any one selected from SEQ ID NOs: 2 and 42 to 48;

(2) a protein comprising an amino acid sequence with one or more amino acid deletions, insertions, substitutions, and/or additions in the amino acid sequence set forth in any one selected from SEQ ID NOs: 2 and 42 to 48; and (3) a protein comprising an amino acid sequence having 80% or more sequence identity to the amino acid sequence set forth in any one selected from SEQ ID NOs: 2 and 42 to 48.

The engineered L31 protein of the present invention is preferably a protein functionally equivalent to a protein comprising the amino acid sequence of any of SEQ ID NOs: 2 and 42 to 48, or the amino acid sequence of SEQ ID NO: 2.

Herein, the term "comprise" means both "comprise" and "consist of".

In some embodiments, the engineered L31 protein of the present disclosure may be a protein comprising an amino acid sequence with one or more (for example, not more than 10, not more than 9, not more than 8, not more than 7, not more than 6, not more than 5, not more than 4, or not more than 3, or 2, 3, 4, 5, 6, 7, 8, 9, or 10, or more than 10) amino acid insertions, substitutions, deletions, and/or additions in the amino acid sequence of (i) a protein comprising an amino acid sequence with deletion of 6 or more or 8 or more amino acid residues from the C terminus in the amino acid sequence set forth in SEQ ID NO: 1 or (ii) a protein comprising an amino acid sequence set forth in any selected from SEQ ID NOs: 2 and 42 to 48. The amino acid additions, deletions, substitutions, and/or insertions can be performed by methods known to those skilled in the art. For example, site-specific mutagenesis (Kunkel et al., Proc. Natl. Acad. Sci. USA 82, 488-492(1985)), Overlap extension PCR, and such can be performed on a nucleic acid encoding the amino acid sequence. These may be carried out individually or in combination, as appropriate.

Generally, alterations (for example, conservative substitutions, deletions, insertions, and/or additions) of one or more (for example, not more than 10, not more than 9, not more than 8, not more than 7, not more than 6, not more than 5, not more than 4, or not more than 3, or 2, 3, 4, 5, 6, 7, 8, 9, or 10, or more than 10) amino acids in a protein have been known not to affect its peptide's function and to even enhance the function of the original protein. Depending on the characteristics of their side chains, amino acids are classified into hydrophobic amino acids (A, I, L, M, F, P, W, Y, and V) and hydrophilic amino acids (R, D, N, C, E, Q, G, H, K, S, and T). Furthermore, amino acid side chains can be classified into aliphatic side chains (G, A, V, L, I, and P), side chains containing hydroxyl groups (S, T, and Y), side chains containing sulfur atoms (C and M), side chains containing carboxylic acids and amides (D, N, E, and Q), side chains containing bases (R, K, and H), and side chains containing aromatics (H, F, Y, and W). Proteins resulting from altering amino acids included in a protein having the amino acid sequence set forth in any of SEQ ID NOs: 1, 2, and 42 to 48 to other amino acids classified into the group with the same characteristics, are also included in the engineered L31 proteins of the present invention. An engineered L31 protein of the present invention may also comprise non-conservative alterations, provided that the protein is functionally equivalent to a protein comprising the amino acid sequence of any of SEQ ID NOs: 2 and 42 to 48, or the amino acid sequence of SEQ ID NO: 2.

In an embodiment of the present invention, proteins comprising an amino acid sequence having high sequence identity to the amino acid sequence with deletion of 6 or more or 8 or more amino acid residues from the C terminus in the amino acid sequence set forth in SEQ ID NO: 1 or the amino acid sequence set forth in any of SEQ ID NOs: 1, 2 and 42 to 48 are also included in the engineered L31 proteins of the present disclosure. High identity in the present disclosure refers to sequence identity of at least 50% or more, more preferably 70% or more, even more preferably 80% or more, still more preferably 85% or more, yet even more preferably 90% or more (for example, 91%, 92%, 93%, 94%, 95%, 96%, 97%, 98%, 99% or more) in the entire amino acid sequence or the entire nucleotide sequence. Sequence identity can be determined using the algorithm BLAST (Proc. Natl. Acad. Sci. USA 87: 2264-2268, 1990; and Proc. Natl. Acad. Sci. USA 90: 5873, 1993) by Karlin and Altschul. Programs called BLASTN and BLASTX based on the BLAST algorithm have been developed (Altschul S F, et al: J. Mol. Biol. 215: 403, 1990). When nucleotide sequences are analyzed by BLASTN, the parameters are set, for example, to score=100 and wordlength=12. When amino acid sequences are analyzed by BLASTX, the parameters are set, for example, to score=50 and wordlength=3. When using the BLAST and Gapped BLAST programs, default parameters of the respective programs are used. Specific techniques for these analysis methods are known.

In the present disclosure, "functionally equivalent" means that the ribosome comprising the engineered L31 protein shows activity for translation equivalent to that of the ribosome comprising the L31 protein consisting of an amino acid sequence with deletion of 6 or more amino acid residues from the C terminus in the amino acid sequence set forth in SEQ ID NO: 1 (for example, the amino acid sequence of any of SEQ ID NOs: 2 and 42 to 48), in terms of the translation of an mRNA encoding a peptide comprising an unnatural amino acid. Therefore, when a ribosome comprising a certain protein has the same degree of activity in terms of the translation of the mRNA encoding a peptide comprising an unnatural amino acid, as compared to that of the ribosome comprising the L31 protein consisting of an amino acid sequence with deletion of 6 or more amino acid residues from the C terminus in the amino acid sequence set forth in SEQ ID NO: 1 (for example, the amino acid sequence of any of SEQ ID NOs: 2 and 42 to 48), the certain protein can be referred to as "a protein functionally equivalent to an amino acid sequence with deletion of 6 or more amino acid residues from the C terminus in the amino acid sequence set forth in SEQ ID NO: 1 (for example, a protein consisting of the amino acid sequence of any of SEQ ID NOs: 2 and 42 to 48)". The present inventors revealed that compared to a ribosome comprising the L31 protein that comprises the amino acid sequence of SEQ ID NO: 1, ribosomes comprising an L31 protein comprising an amino acid sequence with deletion of 6 or more amino acid residues from the C terminus in the amino acid sequence set forth in SEQ ID NO: 1 (for example, the amino acid sequence of any of SEQ ID NOs: 2 and 42 to 48), have greater activity to translate an mRNA encoding a peptide comprising an unnatural amino acid. Therefore, when ribosomes comprising a certain protein have greater activity to translate an mRNA encoding a peptide comprising an unnatural amino acid, as compared to a ribosome comprising the L31 protein that comprises the amino acid sequence of SEQ ID NO: 1, the certain protein can be referred to as "a protein functionally equivalent to a protein consisting of an amino acid sequence with deletion of 6 or more amino acid residues from the C terminus in the amino acid sequence set forth in SEQ ID NO: 1 (for example, the amino acid sequence of any of SEQ ID NOs: 2 and 42 to 48)". Alternatively, if a certain protein, when constituting a ribosome, provides the ribosome with greater activity to translate an mRNA encoding a peptide comprising an unnatural amino acid as compared to the L31 protein comprising the amino acid sequence of SEQ ID NO: 1, the certain protein can be referred to as "a protein functionally equivalent to a protein consisting of an amino acid sequence with deletion of 6 or more amino acid residues from the C terminus in the amino acid sequence set forth in SEQ ID NO: 1 (for example, the amino acid sequence of any of SEQ ID NOs: 2 and 42 to 48)".

In the present disclosure, "activity to translate an mRNA encoding a peptide comprising an unnatural amino acid" can also be expressed as "efficiency in translating an mRNA encoding a peptide comprising an unnatural amino acid", and specifically, it includes easiness of incorporation of tRNAs carrying unnatural amino acids, degree of read-through of codons encoding unnatural amino acids, amount of translated peptide, and/or amount of by-products generated.

In the present disclosure, "greater activity to translate an mRNA encoding a peptide comprising an unnatural amino acid" can also be expressed as "higher efficiency in translating an mRNA encoding a peptide comprising an unnatural amino acid", and specifically, it means easier incorporation of tRNAs carrying unnatural amino acids, less frequent read-through of codons encoding unnatural amino acids, larger amount of the target peptide generated, and/or smaller amount of by-products generated.

The "activity to translate an mRNA encoding a peptide comprising an unnatural amino acid" in the present disclosure can be evaluated using the percentage of translation products in which amino-acid read-through has occurred relative to all translation products as an indicator. When an mRNA encoding a peptide comprising an unnatural amino acid is translated, the translation products may include, in addition to the target molecule (TM), initiation read-through (iRT) peptides such as a peptide resulting from translation from the amino acid corresponding to the second letter from the beginning due to the read-through of the initial amino acid (referred to as "1iRT" in the present disclosure), and a peptide resulting from translation from the amino acid corresponding to the third letter from the beginning due to the read through of the initial amino acid and the amino acid corresponding to the second letter from the beginning (referred to as "2iRT" in the present disclosure). In the present disclosure, the "iRT percentage" calculated from the initiation read-through (iRT) and the target molecule (TM) concentrations using the equation below can be employed as the "activity to translate an mRNA encoding a peptide comprising an unnatural amino acid". The "total iRT concentration" in the equation can be calculated as the sum of the concentrations of 1iRT (peptide produced by translation started from the second letter from the beginning) and 2iRT (peptide produced by translation started from the third letter from the beginning).

iRT percentage=(total iRT concentration [nM]/(total iRT concentration [nM]+TM concentration [nM])×100 (Equation 1)

Specifically, the iRT percentage enables evaluation by methods described in the Examples using the aminoacyl-tRNAs, translation systems, and such described in the Examples. As an example, translation of the template mRNA of SEQ ID NO: 10 into the peptide of any of SEQ ID NOs: 29 to 31 or preferably SEQ ID NO: 29 enables evaluation of the "activity to translate an mRNA encoding a peptide comprising an unnatural amino acid".

In the present disclosure, "greater activity to translate an mRNA encoding a peptide comprising an unnatural amino acid" can mean that the iRT ratio is low. The phrase "greater activity for translation of the peptide comprising the unnatural amino acid, as compared to a ribosome comprising the wild-type *E. coli* L31 that comprises the amino acid sequence of SEQ ID NO: 1" can mean, for example, that the iRT percentage of a ribosome comprising the engineered L31 protein of the present disclosure is lower than the iRT percentage of a ribosome comprising the wild-type *E. coli* L31 that comprises the amino acid sequence of SEQ ID NO: 1 by 15%, 20%, 25%, 30%, or more.

Prokaryotic ribosome contains the 50S large subunit and the 30S small subunit. Furthermore, the 50S subunit is composed of 23SrRNA and 5SrRNA as well as multiple proteins. Furthermore, the 30S subunit is composed of 16SrRNA and multiple proteins. On the other hand, eukaryotic ribosomes contain the 60S large subunit and the 40S small subunit. Furthermore, the 60S subunit is composed of 28SrRNA, 5.8SrRNA, and 5SrRNA, as well as multiple proteins. Furthermore, the 40S subunit is composed of 18SrRNA and multiple proteins. Factors constituting ribosomes are known to those skilled in the art.

Amino Acids

In the present disclosure, "amino acids" constituting peptides include "natural amino acids" such as α-amino acids and "unnatural amino acids" such as β-amino acids and γ-amino acids. The three-dimensional structure of an amino acid may be either an L-type amino acid or a D-type amino acid. "Amino acid", "natural amino acid", and "unnatural amino acid" may be referred to as "amino acid residue", "natural amino acid residue", and "unnatural amino acid residue", respectively.

In particular embodiments, the natural amino acids are the following 20 types of α-amino acids: glycine (Gly), alanine (Ala), serine (Ser), threonine (Thr), valine (Val), leucine (Leu), isoleucine (Ile), phenylalanine (Phe), tyrosine (Tyr), tryptophan (Trp), histidine (His), glutamic acid (Glu), aspartic acid (Asp), glutamine (Gln), asparagine (Asn), cysteine (Cys), methionine (Met), lysine (Lys), arginine (Arg), and proline (Pro). Alternatively, amino acids resulting from exclusion of any one or more types of amino acids from the above-mentioned 20 types of amino acids may be used as the natural amino acids in the present disclosure. In one embodiment, the natural amino acids consist of 19 types of amino acids which exclude isoleucine. In one embodiment, the natural amino acids consist of 19 different types of amino acids which exclude methionine. In a further embodiment, the natural amino acids consist of 18 types of amino acids which exclude isoleucine and methionine. Natural amino acids are usually L-type amino acids.

Unnatural Amino Acids

In the present disclosure, unnatural amino acids refer to all amino acids excluding the natural amino acids consisting of the 20 types of α-amino acids mentioned above. Examples of the unnatural amino acid include, β-amino acids, γ-amino acids, D-type amino acids, α-amino acids having side chains that are different from those of natural amino acids, α,α-disubstituted amino acids, and amino acids having a substituent on its main-chain amino group (N-substituted amino acids). The side chain of an unnatural amino acid is not particularly limited, but in addition to a hydrogen atom, it may carry alkyl, alkenyl, alkynyl, aryl, heteroaryl, aralkyl, cycloalkyl, or such. Furthermore, in the case of α,α-disubstituted amino acids, two side chains may form a ring. In addition, these side chains may carry one or more substituents. In a specific embodiment, the substituents may be selected from any functional group containing a halogen atom, an O atom, an S atom, an N atom, a B atom, an Si atom, or a P atom. For example, in the present disclosure, "C1-C6 alkyl having halogen as a substituent" means "C1-C6 alkyl" in which at least one hydrogen atom in the alkyl is substituted with a halogen atom, and specifically includes, for example, trifluoromethyl, difluoromethyl, fluoromethyl, pentafluoroethyl, tetrafluoroethyl, trifluoroethyl, difluoroethyl, fluoroethyl, trichloromethyl, dichloromethyl, chloromethyl, pentachloroethyl, tetrachloroethyl, trichloroethyl, dichloroethyl, and chloroethyl. Furthermore, for example, "C5-C10 aryl C1-C6 alkyl having a substituent" means "C5-C10 aryl C1-C6 alkyl" in which at least one hydrogen atom in aryl and/or alkyl is substituted with a substituent. "Having two or more substituents" also means having a certain functional group (for example, a functional group containing an S atom) as a substituent which further has another substituent (for example, a substituent such as amino or halogen). For specific examples of unnatural amino acids, one can also refer to WO2013/100132, WO2018/143145 and such.

The main chain amino group of an unnatural amino acid may be an unsubstituted amino group ($NH_2$ group) or a substituted amino group (NHR group). Here, R represents alkyl, alkenyl, alkynyl, aryl, heteroaryl, aralkyl, or cycloalkyl which may carry a substituent. Furthermore, the carbon chain bonded to the N atom of the main chain amino group and the carbon atom at the a position may form a ring, as in proline. Examples of alkyl substitutions of amino groups include N-methylation, N-ethylation, N-propylation, and N-butylation, and examples of aralkyl substitutions include N-benzylation. Specific examples of N-methyl amino acids include N-methylalanine, N-methylglycine, N-methylphenylalanine, N-methyltyrosine, N-methyl-3-chlorophenylalanine, N-methyl-4-chlorophenylalanine, N-methyl-4-methoxyphenylalanine, N-methyl-4-thiazolealanine, N-methylhistidine, N-methylserine, and N-methylaspartic acid.

Examples of a substituent containing halogen include an alkyl group, a cycloalkyl group, an alkenyl group, an alkynyl group, an aryl group, a heteroaryl group, and an aralkyl group carrying halogen as a substituent, and more specifically, examples include fluoroalkyl, difluoroalkyl, and trifluoroalkyl.

Examples of O atom-contained substituents include hydroxyl (—OH), oxy (—OR), carbonyl (—C═O—R), carboxyl (—$CO_2$H), oxycarbonyl (—C═O—OR), carbonyloxy (—O—C═O—R), thiocarbonyl (—C═O—SR), carbonylthio group (—S—C═O—R), aminocarbonyl (—C═O—NHR), carbonylamino (—NH—C═O—R), oxycarbonylamino (—NH—C═O—OR), sulfonylamino (—NH—$SO_2$—R), aminosulfonyl (—$SO_2$—NHR), sulfamoylamino (—NH—$SO_2$—NHR), thiocarboxyl (—C(═O)—SH), and carboxylcarbonyl (—C(═O)—$CO_2$H).

Examples of oxy (—OR) include alkoxy, cycloalkoxy, alkenyloxy, alkynyloxy, aryloxy, heteroaryloxy, and aralkyloxy.

Examples of carbonyl (—C═O—R) include formyl (—C═O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C═O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.
(—C═O—OR)

Examples of carbonyloxy (—O—C═O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C═O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C═O—R) include, alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C═O—NHR) include alkylaminocarbonyl, cycloalkylaminocarbonyl, alkenylaminocarbonyl, alkynylaminocarbonyl, arylaminocarbonyl, heteroarylaminocarbonyl, and aralkylaminocarbonyl. Additional examples include groups produced by further substitution of an alkyl, a cycloalkyl, an alkenyl, an alkynyl, an aryl, a heteroaryl, or an aralkyl for the H atom bonded to the N atom in —C═O—NHR.

Examples of carbonylamino (—NH—C═O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include groups produced by further substitution of an alkyl, a cycloalkyl, an alkenyl, an alkynyl, an aryl, a heteroaryl, or an aralkyl for the H atom bonded to the N atom in —NH—C═O—R.

Examples of oxycarbonylamino (—NH—C═O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include groups produced by further substitution of an alkyl, a cycloalkyl, an alkenyl, an alkynyl, an aryl, a heteroaryl, or an aralkyl for the H atom bonded to the N atom in —NH—C═O—OR.

Examples of sulfonylamino (—NH—$SO_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include groups produced by further substitution of an alkyl, a cycloalkyl, an alkenyl, an alkynyl, an aryl, a heteroaryl, or an aralkyl for the H atom bonded to the N atom in —NH—$SO_2$—R.

Examples of aminosulfonyl (—$SO_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include groups produced by further substitution of an alkyl, a cycloalkyl, an alkenyl, an alkynyl, an aryl, a heteroaryl, or an aralkyl for the H atom bonded to the N atom in —$SO_2$—NHR.

Examples of sulfamoylamino (—NH—$SO_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. Additionally, the two H atoms bonded to the N atoms in —NH—$SO_2$—NHR may be substituted with a substituent independently selected from the group consisting of an alkyl, a cycloalkyl, an alkenyl, an alkynyl, an aryl, a heteroaryl, and an aralkyl; or these two substituents may form a ring.

For S atom-contained substituents, examples include thiol (—SH), thio (—S—R), sulfinyl (—S═O-R), sulfonyl (—S(O)$_2$—R), and sulfo (—$SO_3$H).

Examples of thio (—S—R) include alkylthio, cycloalkylthio, alkenylthio, alkynylthio, arylthio, heteroarylthio, aralkylthio, and such.

Examples of sulfonyl (—S═O-R) include alkylfulfnyl, cycloalkylsulfinyl, alkenylsulfinyl, alkynylsulfinyl, arylsulfinyl, heteroarylsulfinyl, and aralkylsulfinyl.

Examples of sulfonyl (—S(O)$_2$—R) include alkylsulfonyl, cycloalkylsulfonyl, alkenylsulfonyl, alkynylsulfonyl, arylsulfonyl, heteroarylsulfonyl, and aralkylsulfonyl.

For N atom-contained substituents, examples include azide (—$N_3$, also called "azido group"), cyano (—CN), primary amino (—$NH_2$), secondary amino (—NH—R), tertiary amino (—NR(R')), amidino (—C(═NH)—$NH_2$), substituted amidino (—C(═NR)—NR'R"), guanidino (—NH—C(═NH)—$NH_2$), substituted guanidino (—NR—C(═NR''')—NR'R"), and aminocarbonylamino (—NR—CO—NR'R").

Examples of secondary amino (—NH—R) include alkylamino, cycloalkylamino, alkenylamino, alkynylamino, arylamino, heteroarylamino, and aralkylamino.

Examples of tertiary amino (—NR(R')) include amino groups, such as alkyl(aralkyl)amino, having any two substituents each independently selected from alkyl, cycloalkyl, alkenyl, alkynyl, aryl, heteroaryl, and aralkyl; and these two arbitrary substituents may form a ring.

Examples of substituted amidino (—C(═NR)—NR'R") include groups in which each of the three substituents R, R', and R" on the N atoms is independently selected from among alkyl, cycloalkyl, alkenyl, alkynyl, aryl, heteroaryl, and aralkyl; and such examples include alkyl(aralkyl)(aryl)amidino.

Examples of substituted guanidino (—NR—C(═NR''')—NR'R") include groups in which each of R, R', R", and R''' is independently selected from alkyl, cycloalkyl, alkenyl, alkynyl, aryl, heteroaryl, and aralkyl; or groups in which they form a ring.

Examples of aminocarbonylamino (—NR—CO—NR'R") include groups in which each of R, R', and R" is independently selected from a hydrogen atom, alkyl, cycloalkyl, alkenyl, alkynyl, aryl, heteroaryl, and aralkyl; or groups in which they form a ring.

Examples of B atom-contained substituents include boryl (—BR(R')) and dioxyboryl (—B(OR)(OR')). These two substituents, R and R', are each independently selected from alkyl, cycloalkyl, alkenyl, alkynyl, aryl, heteroaryl, and aralkyl; or they may form a ring.

At least one atom constituting an "amino acid" constituting the peptide may be an atom (isotope) of the same atomic number (number of protons) and different mass number (total number of protons and neutrons). Examples of the isotope contained in the "amino acid" constituting the peptide include a hydrogen atom, a carbon atom, a nitrogen atom, an oxygen atom, a phosphorus atom, a sulfur atom, a fluorine atom, and a chlorine atom, including $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$.

Examples of "halogen atoms" as used herein include F, Cl, Br, and I.

Herein, "alkyl" refers to a monovalent group derived by removing any one hydrogen atom from an aliphatic hydrocarbon, and covers a subset of hydrocarbyl or hydrocarbon group structures that contain hydrogen and carbon atoms, but do not contain a heteroatom (which refers to an atom other than carbon and hydrogen atoms) or an unsaturated carbon-carbon bond in the skeleton. Alkyl includes not only linear chain alkyl, but also branched chain alkyl. Alkyl is specifically alkyl having 1 to 20 carbon atoms ($C_1$-$C_{20}$; hereinafter, "$C_p$-$C_q$" means that the number of carbon atoms is p to q), and preferred examples include $C_1$-$C_{10}$ alkyl, and more preferably $C_1$-$C_6$ alkyl. Specific examples of the alkyl include methyl, ethyl, n-propyl, i-propyl, n-butyl, s-butyl, t-butyl, isobutyl(2-methylpropyl), n-pentyl, s-pentyl(1-methylbutyl), t-pentyl(1,1-dimethylpropyl), neopentyl(2,2-dimethylpropyl), isopentyl(3-methylbutyl), 3-pentyl(1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

Herein, "alkenyl" refers to a monovalent group having at least one double bond (two adjacent $SP^2$ carbon atoms). Depending on the configuration of the double bond and a substituent (if present), the geometry of the double bond can be an entgegen (E) or zusammen (Z) or a cis or trans configuration. Alkenyl includes not only linear chain alkenyl but also branched chain alkenyl. Examples of the alkenyl are preferably $C_2$-$C_{10}$ alkenyl, more preferably $C_2$-$C_6$ alkenyl, and specifically vinyl, allyl, 1-propenyl, 2-propenyl, 1-butenyl, 2-butenyl (including cis and trans), 3-butenyl, pentenyl, 3-methyl-2-butenyl, and hexenyl.

Herein, "alkynyl" refers to a monovalent group having at least one triple bond (two adjacent SP carbon atoms). Alkynyl includes not only linear chain alkynyl but also branched chain alkynyl. Examples of the alkynyl are preferably $C_2$-$C_{10}$ alkynyl, more preferably $C_2$-$C_6$ alkynyl, and specifically ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

Herein, "cycloalkyl" means a saturated or partially saturated cyclic monovalent aliphatic hydrocarbon group, including single rings, bicyclo rings, and spiro rings. Examples of the cycloalkyl are preferably $C_3$-$C_8$ cycloalkyl, and specifically cyclopropyl, cyclobutyl, cyclopentyl, cyclohexyl, cycloheptyl, cyclooctyl, bicyclo[2.2.1]heptyl, and spiro[3.3]heptyl.

Herein, "aryl" means a monovalent aromatic hydrocarbon ring, and preferred examples include $C_6$-$C_{10}$ aryl. Specific examples of the aryl include phenyl and naphthyl (for example, 1-naphthyl and 2-naphthyl).

Herein, "heteroaryl" means a monovalent aromatic ring group containing 1 to 5 heteroatoms in addition to carbon atoms. The ring may be a single ring or a fused ring formed with another ring, which may be partially saturated. The number of the ring-constituting atoms is preferably 5 to 10 (5- to 10-membered heteroaryl), and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

Herein, "alkoxy" means an oxy group to which the above-defined "alkyl" is bonded, and preferred examples include $C_1$-$C_6$ alkoxy. Specific examples of the alkoxy include methoxy, ethoxy, 1-propoxy, 2-propoxy, n-butoxy, i-butoxy, s-butoxy, t-butoxy, pentyloxy, and 3-methylbutoxy.

Herein, "alkenyloxy" means an oxy group to which the above-defined "alkenyl" is bonded, and preferred examples include $C_2$-$C_6$ alkenyloxy. Specific examples of the alkenyloxy include vinyloxy, aryloxy, 1-propenyloxy, 2-propenyloxy, 1-butenyloxy, 2-butenyloxy (including cis and trans), 3-butenyloxy, pentenyloxy, and hexenyloxy.

Herein, "cycloalkoxy" means an oxy group to which the above-defined "cycloalkyl" is bonded, and preferred examples include $C_3$-$C_8$ cycloalkoxy. Specific examples of the cycloalkoxy include cyclopropoxy, cyclobutoxy, and cyclopentyloxy.

Herein, "aryloxy" means an oxy group to which the above-defined "aryl" is bonded, and preferred examples include $C_6$-$C_{10}$ aryloxy. Specific examples of the aryloxy include phenoxy, 1-naphthyloxy, and 2-naphthyloxy.

Herein, "amino" means $-NH_2$ in a narrow sense, and means —NRR' in a broad sense, wherein R and R' are independently selected from hydrogen, alkyl, alkenyl, alkynyl, cycloalkyl, heterocyclyl, aryl, or heteroaryl, or wherein R and R', together with the nitrogen atom to which they are attached, form a ring. Preferred examples of the amino include $-NH_2$, mono $C_1$-$C_6$ alkylamino, di $C_1$-$C_6$ alkylamino, and 4- to 8-membered cyclic amino.

Herein, "monoalkylamino" means a group corresponding to the above-defined "amino" in which R is hydrogen and R' is the above-defined "alkyl", and preferred examples include mono $C_1$-$C_6$ alkylamino. Specific examples of the monoalkylamino include methylamino, ethylamino, n-propylamino, i-propylamino, n-butylamino, s-butylamino, and t-butylamino.

Herein, "dialkylamino" means a group corresponding to the above-defined "amino" in which R and R' are independently the above-defined "alkyl", and preferred examples include di $C_1$-$C_6$ alkylamino. Specific examples of the dialkylamino include dimethylamino and diethylamino.

Herein, "aminoalkyl" means a group in which one or more hydrogens of the above-defined "alkyl" are substituted with the above-defined "amino", and is preferably $C_1$-$C_6$ aminoalkyl. Specific examples of the aminoalkyl include 1-pyridylmethyl, 2-(1-piperidyl)ethyl, 3-(1-piperidyl)propyl, and 4-aminobutyl.

Herein, "aralkyl (arylalkyl)" means a group in which at least one hydrogen atom in the above-defined "alkyl" is substituted with the above-defined "aryl", and is preferably $C_7$-$C_{14}$ aralkyl and more preferably $C_7$-$C_{10}$ aralkyl. Specific examples of the aralkyl include benzyl, phenethyl, and 3-phenylpropyl.

For specific examples of the unnatural amino acid, one may refer to WO2013/100132, WO2018/143145, and such.

In an embodiment, peptides that includes one or more types of amino acids obtained by the production method of the present invention can be utilized as pharmaceuticals. In case peptides are used as pharmaceuticals, high metabolic stability and membrane permeability are preferred. Such characteristics as used herein refer to "drug-likeness" or "drug-like." The term "drug-like amino acid" as used herein refers to α-, β-, and γ-amino acids, where one of the two hydrogen atoms of the main chain amino group ($NH_2$ group), or one or two of the hydrogen atoms of the main chain methylene group (—$CH_2$— group), may be substituted with an alkyl group, a cycloalkyl group, an alkenyl group, an alkynyl group, an aryl group, a heteroaryl group, an aralkyl group, or the like. These substituents may be further substituted with a "substituent contributing to drug-likeness." Preferred examples of the drug-like amino acid are amino acids having a "long side chain" disclosed in WO2018/225864. Drug-like amino acids may also be L-amino acids, D-amino acids, α,α-disubstituted amino acids, N-substituted amino acids, or the like. Drug-like amino acids do not necessarily have to be translatable. Drug-like amino acids include side chain moieties of peptides obtained from "translated amino acids" (e.g., a D-amino acid obtained by chemically modifying D-tyrosine when a hit compound is obtained at D-tyrosine, or a β-amino acid obtained by chemically modifying β-alanine when a hit compound is obtained at β-alanine), or amino acids that can be chemically synthesized by optimizing the structure of the N-substituted moiety by chemical transformation of N-methylamino acid. Such amino acids function as a constituent of a drug-like peptide, and therefore are selected from a range of amino acids that can provide a drug-like peptide by post-translational chemical modification. For example, as described below, lysines having an aminoalkyl group are not included in drug-like amino acids when amino groups are not involved in post-translational modification. However, lysine units are included as units of drug-like amino acids when amino groups of lysines are utilized as reactive functional groups in post-translational modification (e.g., intersection units). In this manner, whether amino acids are "drug-like amino acids" is determined by the functional group that has been transformed by post-translational modification. Examples of the substituents separately defined above that can be such substituents include an ester group (—CO—OR), a thioester group (—CO—SR), a thiol group (—SH) or a protected thiol group, an amino group (—$NH_2$), a monosubstituted amino group (—NH—R) or a disubstituted amino group (—NRR'), or a protected amino group, a substituted sulfonylamino group (—NH—$SO_2$—R), an alkylborane group (—BRR'), an alkoxyborane group (—B(OR)(OR')), an azido group (—$N_3$), a keto acid group (—CO—COH), a thiocarboxylic acid group (—CO—SH), a phosphoryl ester group (—CO—PO(R)(R')), and an acylhydroxyamino group (—NH—O—CO—R). One or two non-adjacent methylene groups contained in the side chain of the drug-like amino acid may be substituted with an oxygen atom, a carbonyl group (—CO—), or a sulfonyl group (—$SO_2$—).

Examples of the "substituent contributing to drug-likeness" as used herein include substituents such as halogen (such as F, Cl, Br, or I), hydroxy (—OH), alkoxy (—OR), oxy (—OR), amido (—NR—COR' or —CO—NRR'), sulfonyl (—$SO_2$—R), sulfinyl (—SOR), oxyamino (—NR—OR'), aminooxy (—O—NRR'), oxycarbonyl (—CO—OR), thiocarbonyl (—CO—SR), thiol (—SH), thio (—SR), primary amino (—$NH_2$), secondary amino (—NHR), or tertiary amino (—NRR'), sulfonylamino (—NH—$SO_2$—R), boryl (—BRR'), dioxyboryl (—B(OR)(OR')), azido (—$N_3$), carboxycarbonyl (—CO—$CO_2$H), phosphorylcarbonyl (—CO—PO(R)(R')), carbonyloxyamino (—NH—O—CO—R), hydroxyamino (—NR—OR'), and aminohydroxy (—O—NRR').

Particularly specific examples of the unnatural amino acids constituting the peptide comprising one or more types of unnatural amino acids of the present disclosure include MeSer(tBuOH), BODIPYFL-4-AMF, MeCys(StBu), MeG, MeStBuOH, Nle, S3F5MePyr, SPh2Cl, MeF, MeHph, MeA3Pyr, SPh2Cl, Pic(2), MeHph, and dA. These unnatural amino acids may be incorporated, for example, at positions corresponding to the second letter or the third letter of the peptides.

Peptides

In the present disclosure, a peptide refers to two or more amino acids connected by amide bonds and/or ester bonds. Without any limitation intended, peptides of the present disclosure include linear peptides and cyclic peptides. Peptides of the present disclosure also include peptides, complexes of peptides and nucleic acids (peptide-nucleic acid complexes), and complexes of peptides, ribosomes, and nucleic acids. "Nucleic acids" of the present disclosure include DNAs, mRNAs, and tRNAs. "Peptides" of the present disclosure may include pharmaceutically acceptable salts thereof.

In one embodiment, peptides of the present disclosure have 2 to 100, 3 to 50, 4 to 30, or 5 to 30 amino acids linked by amide bonds and/or ester bonds. For example, in one embodiment, when the peptide comprising one or more types of unnatural amino acids of the present invention is used as a pharmaceutical, to acquire high membrane permeability, the number of amino acids constituting the peptide is preferably 20 or less, more preferably 18 or less, 16 or less, 15 or less, or 14 or less, and particularly preferably 13 or less, and specific examples include 9, 10, 11, 12, and 13. Furthermore, to acquire high metabolic stability, the number of amino acids constituting the peptide is preferably 8 or more, more preferably 9 or more, even more preferably 10 or more, and particularly preferably 11 or more. When considering acquisition of both membrane permeability and metabolic stability, the number of amino acids constituting the peptide is preferably 5 to 20, or 7 to 20, more preferably 7 to 17, 8 to 16, 9 to 16, or 10 to 16, even more preferably 8 to 13, 10 to 15, 11 to 15, 10 to 14, 10 to 13, or 11 to 14, and particularly preferably 11 to 13.

The number of amino acids constituting the cyclic portion of a cyclic peptide of the present disclosure is not limited, but examples include 4 or more, 6 or more, 7 or more, 8 or more, 9 or more, 10 or more, 11 or more, 12 or more, 20 or less, 18 or less, 16 or less, 15 or less, 14 or less, 13 or less, 12 or less, 11 or less, 7, 8, 9, 10, 11, 12, 13, 14, 15, and 16. When considering acquisition of both membrane permeability and metabolic stability, the number of amino acids constituting the above-mentioned cyclic portion is preferably 5 to 15, more preferably 5 to 14, 7 to 14, or 8 to 14, even more preferably 8 to 13, 9 to 13, 8 to 12, 8 to 11, or 9 to 12, and particularly preferably 9 to 11. Herein, "cyclic portion" of a peptide means a cyclic portion formed by two or more linked amino acid residues.

In a non-limiting embodiment, a cyclic peptide of the present disclosure may have a linear portion. Herein, "linear portion" used to refer to a partial structure of a cyclic peptide, refers to a portion that is not contained in the main chain structure of the cyclic portion, and has at least one amide bond and/or ester bond on the chain of this portion. The number of amino acids (the number of units) in the linear portion is preferably 0 to 8, more preferably 0 to 5, and still more preferably 0 to 3. In a non-limiting embodiment, linear portions in the present disclosure may include natural amino acids and unnatural amino acids (including chemically modified or skeletally transformed amino acids).

In a non-limiting embodiment, examples of the number of unnatural amino acids comprised in a peptide of the present disclosure are preferably 2 or more, more preferably 4 or more, 5 or more, or 6 or more, still more preferably 7 or more, and particularly preferably 8 or more, and also preferably 20 or less, 15 or less, 14 or less, 13 or less, 12 or less, 10 or less, or 9 or less. Examples of the number of unnatural amino acids comprised in a peptide of the present disclosure are 30% or more, 40% or more, 50% or more, 60% or more, 70% or more, or 80% or more relative to the number of amino acids constituting the cyclic portion. Furthermore, a peptide of the present disclosure comprises, for example, preferably 1 or more, more preferably 2 or more, 3 or more, or 4 or more, even more preferably 7 or more, particularly preferably 8 or more types of unnatural amino acids, and also preferably 20 or less, 15 or less, 14 or less, 13 or less, 12 or less, 10 or less, or 9 or less types of unnatural amino acids.

In a peptide comprising one or more types of unnatural amino acids of the present disclosure, the site(s) at which it comprises the unnatural amino acid(s) is not limited, but in one embodiment, the peptide may comprise an unnatural amino acid at the position corresponding to the initial amino acid, and may further comprise unnatural amino acids at positions corresponding to the second-letter and/or the third-letter amino acids.

It is known that when an amino acid other than fMet is introduced at the initial amino acid site, a phenomenon defined as initiation read through (iRT), in which translation starts from the amino acid corresponding to the second letter or the third letter from the beginning, is observed (herein below, peptides produced in this manner are defined as initiation read through peptides (iRT peptides)). By using an engineered L31 protein or a ribosome comprising this protein of the present disclosure, the phenomenon of initiation read through can be avoided even when synthesizing a peptide with an unnatural amino acid introduced at the initial amino acid site. In addition, iRT peptides are not cyclized. Therefore, when producing a library comprising cyclic peptides, if most of the mRNAs encoding these peptides become those coding for iRT peptides, the number of molecules that can be displayed becomes limited, the number of cyclic peptides displayed decreases, and the diversity of the library decreases. Use of the engineered L31 protein of the present disclosure or a ribosome comprising this protein can prevent such decrease in quality of the library.

Peptide-Encoding mRNAs

In the present disclosure, peptides are produced by translating mRNAs encoding peptides comprising one or more types of unnatural amino acids. The mRNAs are RNAs carrying genetic information which may be translated into proteins. Genetic information is encoded on an mRNA as codons, each of which corresponds to one of the total 20 types of amino acids. Protein translation begins at the start codon and ends at the stop codon. In principle, the start codon in eukaryotes is AUG; however, in prokaryotes (eubacteria and archaea), GUG, UUG, and such may be used as start codons in addition to AUG. AUG is a codon encoding methionine (Met), and in eukaryotes and archaea, translation is started from methionine as is. On the other hand, in eubacteria, since the start codon AUG exclusively corresponds to N-formylmethionine (fMet), translation is started from formylmethionine. There are three types of stop codons: UAA (ocher), UAG (amber), and UGA (opal). When the stop codon is recognized by a protein called the translation termination factor (release factor; RF), the peptide chain that has previously been synthesized dissociates from the tRNA and the translation process ends. In one embodiment, the mRNA encoding a peptide comprising one or more types of unnatural amino acids of the present disclosure can be exemplified by an mRNA comprising codons encoding a peptide comprising an unnatural amino acid at least at the position corresponding to the initial amino acid.

In the mRNA encoding a peptide comprising one or more types of unnatural amino acids of the present disclosure, the site at which it comprises the unnatural amino acid(s) is not limited, but in one embodiment, the mRNA may comprise a codon encoding the unnatural amino acid at the position corresponding to the initial amino acid.

Peptide Translation

As described above, in the present disclosure, a peptide comprising one or more types of unnatural amino acids can be produced by translation from the mRNA encoding the peptide. Herein, "translation" means synthesizing a peptide by translation from a nucleic acid (such as DNA or RNA) encoding the peptide. Translation is a step of obtaining a linear peptide by repeated amide bonding and/or ester bonding reactions by action of a ribosome using mRNA as a template.

In one aspect, the present disclosure provides methods for producing peptides comprising at least one type, 2 or more types, 3 or more types, 4 or more types, or 5 or more types of unnatural amino acids and libraries comprising the peptides. Without limitation, such production methods may comprise steps (i) and (ii) below:

(i) preparing at least one type, 2 or more types, 3 or more types, 4 or more types, or 5 or more types of tRNAs to which an unnatural amino acid is attached;

(ii) obtaining the above-mentioned peptide by translating a nucleic acid comprising at least one of the codons corresponding to the anticodons of the above tRNAs in a translation system.

Here, the nucleic acid may comprise at least one of the codons corresponding to the anticodons of the above tRNAs. In another non-limiting embodiment, the mRNA encoding the peptide comprising one or more types of unnatural amino acids of the present disclosure may be an mRNA comprising codons encoding a peptide comprising an unnatural amino acid at least at the position corresponding to the initial amino acid.

In the translation of natural amino acids, 20 types of proteinaceous amino acids and translation termination are assigned to each of the 64 kinds of codons. When a specific amino acid is removed from the translation system, the codon corresponding to that amino acid becomes an empty codon. Therefore, if a desired unnatural amino acid linked to a tRNA having an anticodon complementary to that empty codon is added to the translation system and then translation is performed, this amino acid is encoded by that codon, and a peptide into which the desired unnatural amino acid has been introduced instead of the removed amino acid is formed by the translation.

In an embodiment of the present disclosure, the initiation suppression (iSP) method is preferably used for peptide translation. In a typical translation, generally, as the translation initiation amino acid, methionine is translated as the N-terminal amino acid. For the beginning of translation, there is a specialized "initiator tRNA". When the initiator tRNA is bonded to methionine (formylmethionine in prokaryotes) and then transported to the ribosome, translation is initiated with the N-terminal amino acid being methionine (formylmethionine in prokaryotes). In contrast, producing a peptide having a desired amino acid at the N-terminus by translation in a translation system in which the initiator tRNA aminoacylated with methionine has been removed (or prevented from being generated) and an initiator tRNA aminoacylated with the desired amino acid prepared in advance has been added instead, is called the initiation suppression method. It is known that the tolerance for unnatural amino acids is greater for introduction at the N terminus than during amino acid elongation, and unnatural amino acids having structures significantly different from natural amino acids can be used as the N-terminal amino acid (Non-Patent Literature: J. Am. Chem. Soc. 2009 Apr. 15; 131(14): 5040-1. Translation initiation with initiator tRNA charged with exotic peptides. Goto, Y, Suga, H.). In one embodiment of the present disclosure, the initiator tRNA contained in the translation system may be one acylated with an unnatural amino acid.

Translation Systems

In the present disclosure, "translation system" is defined as a concept that includes both a method for peptide translation and a composition for peptide translation. In the present disclosure, the "translation system" is not limited as long as it contains a ribosome comprising an engineered L31 protein of the present disclosure. The "translation system" of the present disclosure refers to a system further combined with a group of protein factors involved in translation, tRNAs, amino acids, energy sources such as ATPs, and regenerating systems thereof, and preferably includes systems that can translate mRNAs into proteins. Furthermore, systems in which translation is progressing may also be included in the "translation system" herein. The translation systems herein can contain nucleic acids that will serve as templates during peptide translation, and can additionally contain initiation factors, elongation factors, release factors, aminoacyl-tRNA synthetases, and such. These factors can be obtained by purification from various cell extracts. Examples of the cells to purify the factors from may include prokaryotic cells and eukaryotic cells. Examples of the prokaryotic cells are *E. coli* cells, cells of extreme thermophiles, and *Bacillus subtilis* cells. Known eukaryotic cells for use as materials include yeast cells, wheat germs, rabbit reticulocytes, plant cells, insect cells, or animal cells. In addition to naturally-occurring tRNAs and aminoacyl-tRNA synthetases (ARSs), artificial tRNAs and artificial aminoacyl-tRNA synthetases that recognize unnatural amino acids can also be used. Peptides in which unnatural amino acids are introduced site-specifically can be synthesized by using artificial tRNAs and artificial aminoacyl-tRNA synthetases. Furthermore, when necessary, transcription can be performed from template DNAs by adding RNA polymerases such as T7 RNA polymerase to the translation systems.

Herein, "a translation system comprises a certain substance" includes embodiments where even if the system does not include the substance at the start of translation, the substance will be synthesized within the system in the process of translation and included in the system. For example, when a tRNA acylated with an amino acid is synthesized in the process of translation, the translation system is understood to comprise that aminoacyl-tRNA.

The major types of translation systems are translation systems that use living cells and translation systems that use cell extracts (cell-free translation systems). Known translation systems using living cells include, for example, a system in which desired aminoacyl-tRNA and mRNA are introduced into living cells such as *Xenopus* oocytes and mammalian cells by a microinjection method or a lipofection method to perform peptide translation (Nowak et al., Science (1995) 268: 439-442). Known examples of cell-free translation systems are those that use extracts from *E. coli* (Chen et al., Methods Enzymol (1983) 101: 674-690), yeast (Gasior et al., J Biol Chem (1979) 254: 3965-3969), wheat germ (Erickson et al., Methods Enzymol (1983) 96: 38-50), rabbit reticulocytes (Jackson et al., Methods Enzymol (1983) 96: 50-74), HeLa cells (Barton et al., Methods Enzymol (1996) 275: 35-57), insect cells (Swerdel et al., Comp Biochem Physiol B (1989) 93: 803-806), and such. Such a translation system can be appropriately prepared by a method known to those skilled in the art or a method similar thereto. Cell-free translation systems also include a translation system (reconstituted cell-free translation system) constructed by isolating and purifying each of the factors required for peptide translation and reconstituting them (Shimizu et al., Nat Biotech (2001) 19: 751-755). Reconstituted cell-free translation systems may typically contain ribosomes, amino acids, tRNAs, aminoacyl-tRNA synthetase (aaRS), translation initiation factors (for example, IF1, IF2, and IF3), translation elongation factors (for example, EF-Tu, EF-Ts, and EF-G), translation release factors (for example, RF1, RF2, and RF3), ribosome recycling factor (RRF), NTPs as an energy source, energy regeneration system, and other factors required for translation. When the transcription reaction from DNA is also carried out, RNA polymerase and such may be further contained. Various factors to be contained in a cell-free translation system can be isolated and purified by a method well known to those skilled in the art, and used to construct a reconstituted cell-free translation system appropriately. Alternatively, commercially available reconstituted cell-free translation systems such as Genefrontier's PUREfrex (registered trademark) and New England Biolabs' PURExpress (registered trademark) can be used. In the case of a reconstituted cell-free translation system, it is possible to construct a desired translation system by reconstructing only necessary components from among the components of the translation system.

PURESYSTEM (registered trademark) (BioComber, Japan) is a reconstituted cell-free translation system in which protein factors, energy-regenerating enzymes, and ribosomes necessary for translation in *E. coli* are respectively extracted and purified and then mixed with tRNAs, amino acids, ATP, GTP, and such. Since this system not only has a low content of impurities, but is also a reconstituted system, it is possible to easily prepare a system free from protein factors and amino acids desired to be excluded ((i) Nat. Biotechnol. 2001; 19: 751-5. Cell-free translation reconstituted with purified components. Shimizu, Y., Inoue, A., Tomari, Y., Suzuki, T., Yokogawa, T., Nishikawa, K., Ueda, T.; (ii) Methods Mol. Biol. 2010; 607: 11-21. PURE technology. Shimizu, Y., Ueda, T.).

For example, there have been many reports of methods using a stop codon as a codon for introducing an unnatural amino acid. By using the PURESYSTEM mentioned above, synthesis systems can be constructed excluding natural amino acids and ARSs. This allows assignment of the codons encoding the excluded natural amino acids to unnatural amino acids (J. Am. Chem. Soc. 2005; 127:

11727-35. Ribosomal synthesis of unnatural peptides. Josephson, K., Hartman, M C., Szostak, J W.). Furthermore, unnatural amino acids can be added without the exclusion of natural amino acids by breaking codon degeneracy (Kwon, I., et al., Breaking the degeneracy of the genetic code. J. Am. Chem. Soc. 2003, 125, 7512-3.). Peptides comprising N-methylamino acids can be ribosomally synthesized by utilizing the cell-free translation systems such as PURE-SYSTEM.

More specifically, ribosomal synthesis can be carried out, for example, by the addition of mRNA to a known cell-free translation system such as the PURESYSTEM in which protein factors necessary for translation in *E. coli* (methionyl-tRNA transformylase, EF-G, RF1, RF2, RF3, RRF, IF1, IF2, IF3, EF-Tu, EF-Ts and ARS (necessary ones are selected from AlaRS, ArgRS, AsnRS, AspRS, CysRS, GlnRS, GluRS, GlyRS, HisRS, IleRS, LeuRS, LysRS, MetRS, PheRS, ProRS, SerRS, ThrRS, TrpRS, TyrRS and ValRS)), ribosome, amino acids, creatine kinase, myokinase, inorganic pyrophosphatase, nucleoside diphosphate kinase, *E. coli*-derived tRNAs, creatine phosphate, potassium glutamate, HEPES-KOH (pH 7.6), magnesium acetate, spermidine, dithiothreitol, GTP, ATP, CTP, UTP and the like are appropriately selected and mixed. Also, addition of T7 RNA polymerase enables coupled transcription/translation from template DNAs containing T7 promoter. In addition, a group of desired aminoacyl tRNAs and a group of unnatural amino acids (for example, F-Tyr) acceptable by aminoacyl tRNA synthetases (ARSs) can be added to a system to ribosomally synthesize peptide compounds comprising the unnatural amino acids (Kawakami, T., et al. Ribosomal synthesis of polypeptoids and peptoid-peptide hybrids. J. Am. Chem. Soc. 2008, 130, 16861-3; Kawakami, T., et al. Diverse backbone-cyclized peptides via codon reprogramming. Nat. Chem. Biol. 2009, 5, 888-90). Furthermore, mRNAs that encode peptides comprising unnatural amino acids can also be translated by adding variants of ARSs instead of or in addition to natural ARSs, and also adding a group of unnatural amino acids in the system. Alternatively, the efficiency of the translation of mRNAs that encode peptides comprising unnatural amino acids and its accompanying incorporation of unnatural amino acids may be increased by using variants of ribosome, EF-Tu, and the like (Dedkova L M, et al. Construction of modified ribosomes for incorporation of D-amino acids into proteins. Biochemistry. 2006, 45, 15541-51; Doi Y, et al. Elongation factor Tu mutants expand amino acid tolerance of protein biosynthesis system. J Am Chem Soc. 2007, 129, 14458-62; Park H S, et al. Expanding the genetic code of *Escherichia coli* with phosphoserine. Science. 2011, 333, 1151-4).

Further, the translation system in the present disclosure preferably contains ribosomes comprising the engineered L31 protein of the present disclosure at a percentage of at least 50% or more, preferably 60% or more, more preferably 70% or more, even more preferably 80% or more, or particularly preferably 90% or more (for example, 91%, 92%, 93%, 94%, 95%, 96%, 97%, 98%, or 99%, or more) by number of molecules relative to all ribosomes contained in the translation system. The term "all ribosomes" is not particularly limited as long as it refers to ribosomes contained in the translation system, but they can be exemplified by a sum of the ribosomes comprising the engineered L31 protein of the present disclosure and other ribosomes (for example, the ribosomes comprising wild-type *E. coli* L31 and ribosomes functionally equivalent thereto).

The percentage of the engineered L31 protein relative to all ribosomes in the translation system can be calculated, for example, based on the ratio of the mass spectrometric intensity of the engineered L31 protein to that of all ribosomes.

Further, the translation system in the present disclosure preferably contains magnesium ions. Magnesium ions are known to be required for maintaining the associated state of the small and large subunits of the ribosome. The L31 protein is one of the proteins forming the interaction between the large and small subunits of the ribosome. Ribosomes lacking the L31 protein and ribosomes comprising shortL31 have been shown to require a higher magnesium ion concentration to maintain the associated state than ribosomes comprising intact L31. Therefore, in the production method of the present disclosure in which a ribosome comprising an engineered L31 protein is used, the magnesium ion concentration is preferably made higher than the magnesium ion concentration in the translation system in which the ribosome comprising intact L31 is used. To prepare such a translation system, the method of the present invention can further comprise a step of adding magnesium ions to the translation system of the present invention. Alternatively, in the present invention, a translation system to which magnesium ions have been added in advance can also be used. The amount of magnesium added is not particularly limited, but examples include, for example, ranges that can be specified by any combination of a lower limit selected from values of 1 mM or more, 2 mM or more, 3 mM or more, 4 mM or more, 5 mM or more, 6 mM or more, or 7 mM or more, and an upper limit selected from 9 mM or less, 8 mM or less, 7 mM or less, 6 mM or less, 5 mM or less, 4 mM or less, or 3 mM or less.

tRNAs

For incorporation of unnatural amino acids into peptides by translating mRNAs that encode peptides comprising unnatural amino acids, aminoacylation of tRNAs that are orthogonal and efficiently incorporated into ribosomes is necessary ((i) Biochemistry. 2003; 42: 9598-608. Adaptation of an orthogonal archaeal leucyl-tRNA and synthetase pair for four-base, amber, and opal suppression. Anderson, J C., Schultz, P G.; and (ii) Chem. Biol. 2003; 10: 1077-84. Using a solid-phase ribozyme aminoacylation system to reprogram the genetic code. Murakami, H., Kourouklis, D., Suga, H.). The following five methods can be used as methods for aminoacylating tRNAs.

Within cells, aminoacyl tRNA synthetases (ARS) for respective amino acids are provided as enzymes for aminoacylating tRNAs. Therefore, the first method includes methods of utilizing the fact that certain ARSs accept unnatural amino acids such as N-Me His, or methods of preparing and using mutant aminoacyl tRNA synthetases that accept unnatural amino acids ((i) Proc. Natl. Acad. Sci. USA. 2002; 99: 9715-20. An engineered *Escherichia coli* tyrosyl-tRNA synthetase for site-specific incorporation of an unnatural amino acid into proteins in eukaryotic translation and its application in a wheat germ cell-free system. Kiga, D., Sakamoto, K., Kodama, K., Kigawa, T., Matsuda, T., Yabuki, T., Shirouzu, M., Harada, Y., Nakayama, H., Takio, K., Hasegawa, Y., Endo, Y., Hirao, I., Yokoyama, S.; (ii) Science. 2003; 301: 964-7. An expanded eukaryotic genetic code. Chin, J W., Cropp, T A., Anderson, J C., Mukherji, M., Zhang, Z., Schultz, P G., Chin, J W.; and (iii) Proc. Natl. Acad. Sci. USA. 2006; 103: 4356-61. Enzymatic aminoacylation of tRNA with unnatural amino acids. Hartman, M C., Josephson, K., Szostak, J W.). Second, a method in which tRNAs are aminoacylated in vitro, and then the amino acids are chemically modified can also be used (J. Am. Chem. Soc. 2008; 130: 6131-6. Ribosomal synthesis of N-methyl peptides. Subtelny, A O., Hartman, M C., Szostak, J W.). Third, tRNAs in which CA has been removed from the 3'-end CCA sequence can be linked with a separately prepared aminoacylated pdCpA by using RNA ligase to obtain aminoacyl tRNAs (Biochemistry. 1984; 23: 1468-73. T4 RNA ligase mediated preparation of novel "chemically misacylated" tRNAPheS. Heckler, T G., Chang, L H., Zama, Y., Naka, T., Chorghade, M S., Hecht, S M.). There is also aminoacylation by flexizymes, which are ribozymes that allow tRNAs to carry active esters of various unnatural amino acids (J. Am. Chem. Soc. 2002; 124: 6834-5. Aminoacyl-tRNA synthesis by a resin-immobilized ribozyme. Murakami, H., Bonzagni, N J., Suga, H.). Fourth, a method in which tRNA and the active ester of an amino acid are ultrasonically agitated within cationic micelles can also be used (Chem. Commun. (Camb). 2005; (34): 4321-3. Simple and quick chemical aminoacylation of tRNA in cationic micellar solution under ultrasonic agitation. Hashimoto, N., Ninomiya, K., Endo, T., Sisido, M.). Fifth, aminoacylation is also possible by linking an amino acid active ester to a PNA that is complementary to a sequence close to the 3'-end of a tRNA and adding this to the tRNA (J. Am. Chem. Soc. 2004; 126: 15984-9. In situ chemical aminoacylation with amino acid thioesters linked to a peptide nucleic acid. Ninomiya, K., Minohata, T., Nishimura, M., Sisido, M.).

More specifically, aminoacyl tRNAs can be prepared using methods such as the following. A template DNA encoding a desired tRNA sequence upstream of which a T7, T3 or SP6 promoter is placed is prepared. RNA can be synthesized by transcription of the DNA using an RNA polymerase compatible with the promoter, such as T7 RNA polymerase, or T3 or SP6 RNA polymerase. tRNAs can also be extracted from cells and purified, and a generated tRNA of interest can be extracted therefrom by using a probe having a sequence complementary to the tRNA sequence. In such extraction, cells transformed with an expression vector for the tRNA of interest may be used as a source. RNA with a desired sequence may also be synthesized chemically. For example, the tRNA thus obtained in which CA has been removed from the 3'-end CCA sequence may be linked to a separately prepared aminoacylated pdCpA or pCpA by RNA ligase to obtain an aminoacyl tRNA (pdCpA method, pCpA method). Such tRNAs are useful in the preparation of peptides. Alternatively, aminoacyl tRNAs can also be prepared by preparing full-length tRNAs and aminoacylating them using flexizymes, which are ribozymes that enable tRNAs to carry active esters of various unnatural amino acids. Without any limitation intended, aminoacyl tRNAs can also be prepared using native ARSs or variants thereof. When native ARSs or variants thereof are used, the aminoacyl tRNAs once consumed in the translation system can be regenerated by the native ARSs or variants thereof; therefore, there is no need for aminoacyl tRNAs prepared in advance to exist in a large amount in the translation system. Such ARS variants are described in WO 2016/148044. These methods for preparing aminoacyl tRNAs can also be combined appropriately.

Peptide Cyclization

In a non-limiting embodiment, the method for producing peptides or libraries comprising the peptides in the present disclosure may further comprise a step of cyclizing the translated peptides. Embodiments of the cyclization include, for example, cyclization that uses an amide bond, a carbon-carbon bond, a thioether bond, a disulfide bond, an ester bond, a thioester bond, a lactam bond, a bond mediated by a triazole structure, or a bond mediated by a fluorophore structure. Among them, an amide bond is preferable because of its high metabolic stability. The peptide translation step and the cyclization reaction step may proceed separately or in succession. The cyclization can be carried out by a method known to those skilled in the art described in WO2013/100132, WO2008/117833, WO2012/074129, and such.

The embodiment of bonding in the ring formation is not limited, but may be any of bonding between the N terminus and the C terminus of the peptide, bonding between the N terminus and the side chain of another amino acid residue of the peptide, bonding between the C terminus and the side chain of another amino acid residue of the peptide, or bonding between side chains of amino acid residues, or two or more of these may be used in combination.

In a non-limiting embodiment, the present invention relates to, for example, methods for producing peptides or libraries comprising the peptides, comprising the steps of:

(1) producing by the method described herein, an acyclic peptide comprising one or more types of unnatural amino acids, wherein the acyclic peptide comprises an amino acid residue having a reaction point at one side chain on the C-terminal side and an amino acid residue having another reaction point on the N-terminal side; and (2) bonding the reaction point of the amino acid residue on the N-terminal side with the reaction point at the side chain of the amino acid residue on the C-terminal side to form an amide bond, a carbon-carbon bond, or a thioether bond.

These steps (1) and (2) may proceed separately or in succession.

Specifically, non-limiting embodiments of the peptide cyclization method by amide bonding include a cyclization method in which the amino group of N-terminal methionine and the amino group of lysine positioned downstream (C-terminal side) are crosslinked using disuccinimidyl glutarate (DSG); a method of cyclization in which an amino acid derivative having a chloroacetyl group is introduced as an N-terminal translation initiation amino acid and Cys is positioned downstream, and they are thereby allowed to form a thioether through an intramolecular cyclization reaction; and a method in which a peptide having cysteine or a cysteine analog at the N-terminus and an active ester in the side chain of an amino acid on the C-terminal side is produced by translation and cyclized using native chemical ligation.

In a non-limiting embodiment, the C-terminal site of the peptide in the present disclosure may not remain as a carboxylic acid but undergo chemical modification. For example, the carboxylic acid site may be reacted with piperidine or such and thereby converted into piperidinamide or the like.

Libraries

The present invention relates to a peptide produced by the peptide production method described herein, and a library comprising such peptides. Furthermore, the present invention relates to the peptide-containing libraries comprising the step of producing the peptides by the peptide production method described herein. The libraries of the present disclosure include libraries comprising peptides of the present disclosure, and libraries comprising nucleic acids encoding the peptides of the present disclosure. Libraries in the present disclosure include libraries of peptides in the present disclosure and libraries of peptide-nucleic acid complexes. The library is preferably a display library. Examples of the display library include a display-utilizing library, and among them, an mRNA display library, a DNA display library, and a ribosome display library are preferable, and an mRNA display library is more preferable.

Display Libraries

The display library refers to a library in which peptides as phenotypes are associated with their peptide-encoding RNAs or DNAs as genotypes. By utilizing such library, the peptides that can specifically bind to the targeted molecules can be identified. For example, the library is contacted with desired immobilized targets, and peptides binding to the targets can be enriched by washing away molecules unbound with the targets (panning). The gene information associated with the peptides selected through such a process can be analyzed to determine the sequences of the peptides bound to the targets. For example, a method using the nonspecific conjugation of an antibiotic puromycin, an aminoacyl-tRNA analog, to proteins during their mRNA translation elongation by the ribosome has been reported as mRNA display (Proc. Natl. Acad. Sci. USA. 1997; 94: 12297-302. RNA-peptide fusions for the in vitro selection of peptides and proteins. Roberts, R. W., Szostak, J. W.) or in vitro virus (FEBS Lett. 1997; 414: 405-8. In vitro virus: bonding of mRNA bearing puromycin at the 3'-terminal end to the C-terminal end of its encoded protein on the ribosome in vitro. Nemoto, N., Miyamoto-Sato, E., Husimi, Y., Yanagawa, H.).

By conjugating spacers such as puromycin to the 3'-ends of an mRNA library obtained by transcription from a DNA library containing a promoter such as T7 promoter, when these mRNAs are translated into proteins in cell-free translation systems, puromycin is mistaken as amino acids by the ribosome, and is incorporated into proteins. The mRNA is linked to the proteins encoded thereby, thus a library in which mRNAs are associated with their products is obtained. This process, which does not involve the transformation of *E. coli* or the like, attains high efficiency and can construct a large-scale display library. cDNA is synthesized from the mRNA serving as a tag containing genetic information bound to the molecule enriched and selected by panning, and then amplified by PCR. The amplified products can be sequenced to determine the sequence of the peptide linked.

In addition to the mRNA display, the following libraries are known as display libraries using cell-free translation systems:

- cDNA display is a library comprising peptide-encoding cDNAs linked to peptide-puromycin complexes (Nucleic Acids Res. 2009; 37 (16): e108. cDNA display: a novel screening method for functional disulfide-rich peptides by solid-phase synthesis and stabilization of mRNA-protein fusions. Yamaguchi, J., Naimuddin, M., Biyani, M., Sasaki, T., Machida, M., Kubo, T., Funatsu, T., Husimi, Y., Nemoto, N.);
- ribosome display which utilizes characteristics that ribosome and translation products are in relatively stable complexes during mRNA translation (Proc. Natl. Acad. Sci. USA. 1994; 91: 9022-6. An in vitro polysome display system for identifying ligands from very large peptide libraries. Mattheakis, L C., Bhatt, R R., Dower, W J.);
- covalent display which utilizes characteristics that bacteriophage endonuclease P2A forms covalent bond with DNAs (Nucleic AcidsRes. 2005; 33: e10. Covalent antibody display—an in vitro antibody-DNA library selection system. Reiersen, H., Lobersli, I., Loset, G A., Hvattum, E., Simonsen, B., Stacy, J E., McGregor, D., Fitzgerald, K., Welschof, M., Brekke, O H., Marvik, O J.); and
- CIS display which utilizes characteristics that a microbial plasmid replication initiator protein RepA binds to a replication origin ori (Proc. Natl. Acad. Sci. USA. 2004; 101: 2806-10. CIS display: In vitro selection of peptides from libraries of protein-DNA complexes. Odegrip, R., Coomber, D., Eldridge, B., Hederer, R., Kuhlman, P A., Ullman, C., FitzGerald, K., McGregor, D.). Also, in vitro compartmentalization is known in which a transcription-translation system is encapsulated into a water-in-oil emulsion or liposome per DNA molecule constituting a DNA library, and subjected to translation reaction (Nat. Biotechnol. 1998; 16: 652-6. Man-made cell-like compartments for molecular evolution. Tawfik, S, Griffiths, D.). The methods described above can be employed appropriately using known methods.

Nucleic Acid Libraries

"Nucleic acid" in the present disclosure may include deoxyribonucleic acids (DNAs), ribonucleic acids (RNAs), or nucleotide derivatives having artificial bases. Peptide nucleic acids (PNAs) may also be included. Nucleic acids of the present disclosure may be any of these nucleic acids or hybrids thereof as long as they retain genetic information of interest. More specifically, the nucleic acids of the present disclosure also include DNA-RNA hybrid nucleotides, and chimeric nucleic acids in which different nucleic acids, such as DNA and RNA, are linked together to form a single strand.

Examples of libraries of nucleic acids serving as templates for the peptide compounds included in the peptide compound library include mRNA libraries and DNA libraries. A nucleic acid library can be obtained by synthesis with a mixture of bases for variable amino acid residue sites on a peptide sequence. For example, it can be synthesized as triplet repeats of a mixture of four bases (N) —A, T, G and C for a DNA library, and A, U, G, and C for an RNA library—or as those in which the first and second letters in each codon are N and the third letter is a mixture of two bases such as W, M, K, or S. Furthermore, if it is intended that the number of amino acid species to be introduced be reduced to 16 or fewer, the third letter may be one base. Alternatively, codon units corresponding to three-letter codons can be prepared and mixed at arbitrary ratios for use in the synthesis to adjust the frequency of appearance of amino acid residues freely.

These nucleic acid libraries can be translated by using cell-free translation systems. When a cell-free translation system is used, a spacer-encoding sequence is preferably included downstream of the nucleic acid of interest. Spacer sequences include, but are not limited to, sequences containing glycine or serine. In addition, it is preferred that a linker formed by RNA, DNA, hexaethylene glycol (spc18) polymers (for example, 5 polymers), or such is contained between the nucleic acid library and a compound which is incorporated into a peptide during ribosomal translation, such as puromycin or a derivative thereof.

The production of the libraries in the present disclosure can be carried out according to the methods of producing peptides in the present disclosure, and can appropriately be combined with known methods. In one embodiment, the peptide libraries in the present disclosure can be produced using the above-described cell-free translation systems in the present disclosure. More specifically, the library production methods in the present disclosure may comprise the step of synthesizing peptides using the cell-free translation systems in the present disclosure. In one embodiment, the examples, preferred ranges, and embodiments described for the cell-free translation systems in the present disclosure can also be applied, as they are, to the library production methods in the present disclosure.

Screening Methods

In a non-limiting embodiment, peptides that can specifically bind to a target molecule can be selected by screening which uses the libraries in the present disclosure.

In a non-limiting embodiment, the screening methods in the present disclosure can enrich peptides that bind to a target molecule by contacting the library of the peptide that includes one or more unnatural amino acids in the present disclosure with the target molecule, and washing off peptides unbound with the target molecules (panning). In one embodiment, the amino acid sequences of the bound peptides can be identified by synthesizing cDNAs from the mRNAs tags included in the peptides thus selected, which contain their nucleotide sequence information, then amplifying the cDNAs by PCR, and sequencing their nucleotide sequences. In one embodiment, a library of mRNAs can be obtained by transcribing the above-mentioned amplified cDNAs, and these can be used as templates to produce a library of peptides again. Since this library is enriched for peptides that can bind to a target molecule, this library can be used for panning again to further concentrate peptides that can specifically bind to the target molecule. The peptides of interest can further be concentrated by repeating these steps multiple times. In one embodiment, the amino acid sequences of the peptides concentrated in this manner can be determined based on the nucleotide sequence information contained in the peptides, and then the peptides that can specifically bind to the target molecule can be produced. In one embodiment, the screening methods in the present disclosure can be performed in vitro.

In a non-limiting embodiment, the peptides obtained by the screening methods in the present disclosure may be subjected to chemical modifications and such by known methods to optimize the peptides. Herein, "optimize (optimization)" means chemical modification of a translated peptide by transforming the structure of each amino acid within the peptide such that the compound becomes a more drug-like peptide, a peptide having stronger activity to a drug efficacy target, and/or a peptide whose toxicity is avoided to a higher extent.

In a non-limiting embodiment, the screening methods in the present disclosure comprise the steps of:

(a) contacting the peptides comprised in the library in the present disclosure with a target molecule; and (b) selecting peptides that can bind to the target molecule.

The screening methods in the present disclosure may comprise prior to step (a) above, the step of obtaining a library according to the method described herein. The library can be obtained in accordance with the production methods of the peptides in the present disclosure.

In one embodiment, in the screening methods in the present disclosure, the aforementioned steps (a) and (b) can be repeated two or more times to concentrate peptides that can specifically bind to a target molecule.

Target Molecules

Target molecules used in the screening methods in the present disclosure are not particularly limited, and include, for example, proteins, peptides, nucleic acids, sugars, and lipids, but, inter alia, proteins are preferably used as targets. The locations where the target molecule exists in vivo are also not particularly limited. In one embodiment, intracellular proteins can also become targets.

In a non-limiting embodiment, target molecules used in the screening methods in the present disclosure are used after being immobilized onto carriers. The carriers are not particularly limited as long as they can immobilize target molecules, and examples include beads and resins. Target molecules can be immobilized onto carriers by known methods.

As described above, the target molecules of the libraries and screening methods in the present disclosure are not particularly limited, but examples include GTPase KRas (KRAS), Dual specificity mitogen-activated protein kinase kinase 1 (MEK1), Mitogen-activated protein kinase 3 (ERK1), and interleukin 6 receptor (IL-6R). As described in the Examples, the libraries in the present disclosure include peptides that can specifically bind to various target molecules. Therefore, in one embodiment, they may enable drug development for "tough targets", for which drug discovery has been considered difficult.

In a non-limiting embodiment, the method for producing a peptide of the present disclosure may comprise the steps of:

(i) contacting the peptides comprised in the library of the present disclosure with a target molecule;

(ii) selecting the peptide that can bind to the target molecule; and (iii) producing the peptide based on the amino acid sequence of the peptide selected in (ii).

The above method can comprise the step of obtaining the library by a method described herein.

In a non-limiting embodiment, the method for producing a library, the method for producing a peptide, and/or the screening method of the present disclosure may be performed in vitro.

In one aspect, the peptides of the present disclosure may be cyclized peptides.

Nucleic Acids and the Like that Encode the Engineered L31 Proteins

The present invention also relates to the engineered L31 proteins of the present disclosure, ribosomes comprising the proteins, and isolated nucleic acids encoding the proteins. The present invention also relates to vectors or cells containing the nucleic acids.

Examples of the engineered L31 proteins of the present disclosure include (1) to (6) below:

(1) a protein comprising an amino acid sequence with deletion of 6 or more amino acid residues, 8 or more amino acid residues, or 9 or more amino acid residues from the C terminus in the amino acid sequence set forth in SEQ ID NO: 1;

(2) a protein comprising an amino acid sequence with one or more amino acid insertions, substitutions, deletions and/or additions in the amino acid sequence of the protein of (1);

(3) a protein comprising an amino acid sequence having 80% or more sequence identity to the amino acid sequence of the protein of (1);

(4) a protein comprising an amino acid sequence set forth in any one selected from SEQ ID NOs: 2 and 42 to 48;

(5) a protein comprising an amino acid sequence with one or more amino acid deletions, insertions, substitutions, and/or additions in the amino acid sequence set forth in any one selected from SEQ ID NOs: 2 and 42 to 48, wherein the protein is a protein functionally equivalent to the protein comprising the amino acid sequence set forth in SEQ ID NO: 2; and (6) a protein comprising an amino acid sequence having 80% or more sequence identity to the amino acid sequence set forth in any one selected from SEQ ID NOs: 2 and 42 to 48, wherein the protein is a protein functionally equivalent to the protein comprising the amino acid sequence set forth in SEQ ID NO: 2.

The engineered L31 proteins of the present disclosure, ribosomes comprising the proteins, isolated nucleic acids and such that encode the proteins can be used, for example, in the production of peptides comprising unnatural amino acids, and libraries comprising the peptides, of the present disclosure.

In the present disclosure, an "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. If the nucleic acid is not present on the natural chromosome, the isolated nucleic acid may be present at any location within the cell. "Nucleic acid" of the present disclosure includes DNA (genomic DNA and cDNA) and RNA.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), $(O)NR_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A method for preparing a nucleic acid encoding an engineered L31 protein of the present disclosure is, for example, a site-directed mutagenesis method (Kramer, W. and Fritz, H.-J. (1987) Oligonucleotide-directed construction of mutagenesis via gapped duplex DNA. Methods in Enzymology, 154: 350-367). Alternatively, a hybridization technique (Southern, E. M. (1975) Journal of Molecular Biology, 98, 503) can also be used to obtain nucleic acids encoding proteins functionally equivalent to the engineered L31 protein set forth in any one selected from SEQ ID NOs: 2 and 42 to 48. More specifically, the nucleic acid encoding the engineered L31 protein of the present disclosure may hybridize under stringent conditions with the nucleic acid encoding the amino acid sequence set forth in any one selected from SEQ ID NOs: 2 and 42 to 48. Stringent hybridization conditions can be appropriately selected by those skilled in the art. For example, in a hybridization solution containing 25% formamide, or 50% formamide under more stringent conditions, 4×SSC, 50 mM Hepes at pH 7.0, 10×Denhardt solution, and 20 μg/mL denatured salmon sperm DNA, prehybridization is performed at 42° C. overnight, and then hybridization is performed by adding a labeled probe and incubating the mixture at 42° C. overnight. The washing solution and temperature conditions for performing the subsequent washing may be, for example, approximately "2×SSC, 0.1% SDS, 50° C.", "2×SSC, 0.1% SDS, 42° C.", and "1×SSC, 0.1% SDS, 37° C."; for more stringent conditions, approximately "2×SSC, 0.1% SDS, 65° C." and "0.5×SSC, 0.1% SDS, 42° C."; and for even more stringent conditions, approximately "0.2×SSC, 0.1% SDS, 65° C.". As the hybridization conditions become more stringent as described above, nucleic acids having higher homology to the nucleic acid sequence encoding the amino acid sequence set forth in any one selected from SEQ ID NOs: 2 and 42 to 48 can be expected to be isolated. However, the combination of SSC, SDS, and temperature conditions described above is exemplary, and those skilled in the art can achieve the same stringency as above by appropriately combining the above-mentioned or other factors that will determine the stringency of hybridization (for example, probe concentration, probe length, and hybridization reaction time).

The nucleic acid thus isolated is believed to have high homology at the amino acid level to the engineered L31 protein set forth in any one selected from SEQ ID NOs: 2 and 42 to 48. Furthermore, at the nucleotide sequence level, it is considered to have high homology to the nucleotide sequence of the nucleic acid encoding the amino acid sequence set forth in any one selected from SEQ ID NO: 2 and 42 to 48. As described above, high homology refers to sequence identity of at least 50% or more, more preferably 70% or more, even more preferably 80% or more, still more preferably 85% or more, yet even more preferably 90% or more in the entire amino acid sequence or the entire nucleotide sequence (for example, 91%, 92%, 93%, 94%, 95%, 96%, 97%, 98%, 99%, or more).

Nucleic acids of the present invention can be used, for example, for preparing engineered L31 proteins or ribosomes comprising them. When preparing an engineered recombinant L31 protein or a ribosome comprising it, usually, a nucleic acid encoding the engineered L31 protein is inserted into a suitable expression vector, and the vector is introduced into a suitable cell, the transformed cells are cultured, and the expressed engineered L31 protein or ribosomes comprising it are isolated, purified, and cultured. The engineered L31 protein can also be expressed as a fusion protein with other proteins for the purpose of facilitating purification. For example, a method for preparing it as a fusion protein with maltose-binding protein using *E. coli* as a host (vector pMAL series commercially available from New England BioLabs, USA), a method for preparing it as a fusion protein with glutathione-S-transferase (GST) (Vector pGEX series commercially available from Amersham Pharmacia Biotech), a method for preparing it with a histidine tag added to it (pET series from Novagen), and such can be used.

In a non-limiting embodiment, the vector may be a knock-in vector to which the nucleic acid of the present invention has been knocked in by homologous recombination. That is, the engineered L31 protein of the present invention, or a ribosome comprising it, can also be prepared by knock-in of the nucleic acid of the present invention to a vector by homologous recombination. Such a vector may be constructed such that a nucleic acid of the present invention for preparing an engineered L31 protein or a ribosome comprising it is inserted in the same reading frame as a target gene in a host such as *E. coli*. In one embodiment, in the knock-in vector, the nucleic acid of the present invention is preferably inserted into an exon containing the translation start site of a target gene such that the translation start site of the nucleic acid coincides with the translation start site of the target gene. In this case, in the knock-in vector, a nucleotide sequence upstream of the translation start site of the target gene is preferably positioned at the 5' side of the translation start site of a foreign gene. In another embodiment, when an exon-intron structure sequence has been added to the 5' side of a foreign gene in the knock-in vector, the nucleic acid of the present invention is preferably inserted into an exon containing the translation start site of the target gene such that the 5' end of the exon-intron structure coincides with the translation start site of the target gene. In this case, in the knock-in vector, a nucleotide sequence upstream of the translation start site of the target gene is preferably positioned 5' upstream of the 5' end of the exon-intron structure.

Furthermore, the knock-in vectors preferably have the ability to replicate in host cells. The knock-in vectors are not particularly limited as long as they are vectors used in genetic engineering, and examples of known vectors include plasmid vectors, cosmid vectors, bacterial artificial chromosome (BAC) vectors, yeast artificial chromosome (YAC) vectors, retrovirus vectors, lentivirus vectors, and other virus vectors.

The host cell is not particularly limited as long as it is a cell suitable for expressing a recombinant protein, and in addition to the above-mentioned *E. coli*, for example, yeast, various animal and plant cells, insect cells and such can be used. Various methods known to those skilled in the art can be used to introduce the vector into the host cell. For example, for introduction into *E. coli*, an introduction method using calcium ions (Mandel, M., Higa, A. (1970) Journal of Molecular Biology, 53, 158-162; and Hanahan, D. (1983) Journal of Molecular Biology, 166, 557-580) can be used. The engineered L31 protein expressed in the host cell can be purified and recovered from the host cell or its cell culture or culture supernatant by a method known to those skilled in the art. When the engineered L31 protein is expressed as a fusion protein with the above-mentioned maltose-binding protein or the like, affinity purification can be easily performed.

In one embodiment of the present disclosure, the nucleic acid of the present invention may be one that has been inserted into a vector. For example, when *E. coli* is used as a host cell, vectors include but are not limited to a vector having an "ori" for amplification in *E. coli* (for example, JM109, DH5α, HB101, or XL1Blue) to achieve the amplification and preparation of a large quantity of the vector in *E. coli* or the like and also having a gene for selecting the transformed *E. coli* (for example, a drug resistance gene that allows discrimination using a drug (ampicillin, tetracycline, kanamycin, chloramphenicol, or such)). Examples of such a vector include M13 vectors, pUC vectors, pBR322, pBluescript, and pCR-Script. When a vector is used for subcloning and excision of cDNA, examples of such a vector include, for example, pGEM-T, pDIRECT, pT7 and the like in addition to the above-mentioned vectors. When a vector is used for producing the engineered L31 protein, an expression vector is particularly useful. When used for expression in *E. coli*, an expression vector must have the above-mentioned characteristics to allow vector amplification in *E. coli*, and, when the host *E. coli* is JM109, DH5u, HB101, XL1-Blue, or such, also carry a promoter that allows efficient expression in *E. coli*, such as lacZ promoter (Ward et al., Nature (1989) 341: 544-546; FASEB J. (1992) 6: 2422-2427), araB promoter (Better et al., Science (1988) 240, 1041-1043), or T7 promoter. Such vectors include pGEX-5X-1 (manufactured by Pharmacia), "QIAexpress system" (manufactured by Qiagen), pEGFP, pET, and such, in addition to the above-mentioned vectors.

The vectors may also contain a signal sequence for polypeptide secretion. As a signal sequence for polypeptide secretion, a pelB signal sequence (Lei, S. P. et al J. Bacteriol. (1987) 169: 4379) may be used when a polypeptide is produced into the *E. coli* periplasm. Introduction of a vector into host cells can be performed, for example, by the calcium chloride method or the electroporation method. Furthermore, examples of vectors for expression in plants include pMH1, pMH2, and pCAMBIA.

In addition to vectors for *E. coli*, examples of the vectors for producing engineered L31 proteins include mammalian expression vectors (for example, pcDNA3 (manufactured by Invitrogen), pEGF-BOS (Nucleic Acids. Res. 1990, 18(17), p 5322), pEF, and pCDM8), insect cell-derived expression vectors (for example, the "Bac-to-BAC baculovairus expression system" (manufactured by Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast-derived expression vectors (for example, "*Pichia* Expression Kit" (manufactured by Invitrogen), pNV11, and SP-QO1), and *Bacillus subtilis*-derived expression vectors (for example, pPL608 and pKTH50).

When used for expression in animal cells such as CHO, COS, and NIH3T3 cells, a vector must have a promoter essential for expression in cells, such as SV40 promoter (Mulligan et al., Nature (1979) 277: 108), MMLV-LTR promoter, EF1α promoter (Mizushima et al., Nucleic Acids Res. (1990) 18: 5322), and CMV promoter, and more preferably it has a gene for selecting transformed cells (for example, a drug resistance gene that allows discrimination using a drug (neomycin, G418, or such)). Examples of vectors with such characteristics include pMAM, pDR2, pBK-RSV, pBK-CMV, pOPRSV, and pOP13.

The transformed cells of the present invention can be used, for example, as a generation system for the production or expression of an engineered L31 protein or a ribosome comprising it. Generation systems for protein production include in vitro and in vivo systems.

When eukaryotic cells are used, for example, animal cells, plant cells, or fungal cells can be used as host cells. Known animal cells include mammalian cells (for example, cells such as 3T3, myeloma cells, baby hamster kidney (BHK), HeLa, and Vero, in addition to CHO cells, COS cells, and NIH3T3 cells described above), amphibian cells (for example, *Xenopus laevis* oocytes (Valle, et al., Nature (1981) 291, 358-340)), and insect cells (for example, sf9, sf21, and Tn5 cells). For CHO cells, in particular, dhfr-CHO (Proc. Natl. Acad. Sci. USA (1980) 77, 4216-4220), which is deficient in the DHFR gene, and CHO K-1 (Proc. Natl. Acad. Sci. USA (1968) 60, 1275), can be preferably used. CHO cells are particularly preferred when large-scale expression is intended.

For plant cells, in addition to the plant-derived cells described below, for example, *Nicotiana tabacum*-derived cells are known as a protein generation system, and this may be subjected to callus culture.

Meanwhile, known fungal cells include, but are not limited to, yeast cells, for example, cells of the genus *Saccharomyces*, such as *Saccharomyces cerevisiae*, and cells of filamentous fungi, for example, the genus *Aspergillus*, such as *Aspergillus niger*.

In the present disclosure, an engineered L31 protein or a ribosome comprising it can also be obtained by purification from a wild-type *E. coli* culture. More specifically, by suspending the cultured wild-type *E. coli* cells in a buffer containing magnesium ions at low concentration, and then disrupting the cells, a lysate containing the engineered L31 protein can be obtained. Specifically, by disrupting the wild-type *E. coli* cells in a buffer containing magnesium ions, for example, at 5 mM or less (more specifically, for example, 4 mM or less, 3 mM or less, 2 mM or less, 1 mM or less, or 0 mM), a lysate containing the wild-type *E. coli* L31 protein of SEQ ID NO: 1 described herein and the engineered L31 protein of the present disclosure can be obtained. Disruption of *E. coli* cells can be carried out using methods known to those skilled in the art, such as disruption by French press, ultrasonication, a homogenizer, glass beads, or a mortar, but disruption by French press is preferred in the present disclosure. The lysate prepared in this manner can be purified by a method known to those skilled in the art to isolate and obtain the engineered L31 protein or the ribosome comprising it.

Another aspect of the present invention provides a composition that comprises a ribosome comprising the engineered L31 protein of the present disclosure. The composition of the present disclosure can be used, for example, as a translation system used in production or such of peptides comprising unnatural amino acids, or a part of such a system. Therefore, the composition of the present disclosure preferably comprises the ribosome comprising the engineered L31 protein of the present disclosure, as well as, for example, an aminoacyl-tRNA formed by attachment of an unnatural amino acid to a tRNA, and an mRNA or such encoding a peptide comprising one or more types of unnatural amino acids. The composition of the present disclosure comprises the ribosome comprising the engineered L31 protein of the present disclosure; preferably, at a percentage of at least 50% or more, preferably 60% or more, more preferably 70% or more, even more preferably 80% or more, or particularly preferably 90% or more (for example, 91%, 92%, 93%, 94%, 95%, 96%, 97%, 98%, or 99%, or more) by number of molecules relative to all ribosomes contained in the composition.

All prior art literature cited herein are incorporated by reference into this description.

EXAMPLES

Herein below, the present invention will be described in more detail with reference to the Examples, but the contents of the present invention are not necessarily limited to the following Examples. The following abbreviations are used in the Examples.

AA: Ammonium acetate
$CH_2CN$: Cyanomethyl group
$CH_3CN$: Acetonitrile
CTACl: N,N,N-Trimethylhexadecan-1-aminium chloride
DBU: 1,8-Diazabicyclo[5.4.0]-7-undecene
DCM: Dichloromethane
DIPEA: N,N-Diisopropylethylamine
DMF: Dimethylformamide
DMSO: Dimethylsulfoxide
FA: Formic acid
Fmoc: 9-Fluorenylmethyloxycarbonyl group
F-Pnaz: 4-(2-(4-Fluorophenyl)acetamide)benzyloxycarbonyl group:

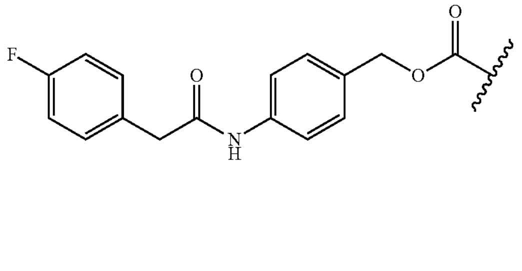 [SMILES: *C(=O)OCc1ccc(NC(=O)Cc2ccc(F)cc2)cc1]

MeCN: Acetonitrile

NMP: N-Methyl-2-pyrrolidone

TEA: Triethylamine

TFA: Trifluoroacetic acid

THF: Tetrahydrofuran

TM: Target molecule

The following abbreviations may be used: MePhe as MeF, Pic(2) as Pic2, Gly as G, Ile as I, Pro as P, Thr as T, MeSer(tBuOH) as MeStBuOH, D-Ala as dA, Leu as L, BODIPYFL-4-AMF as Bdp4AMF, Acbz-D-MeCys(StBu) as AcbzdMeCStBu, Acbz-MeCys(StBu) as AcbzMeCStBu, and Acbz-Cys(StBu) as AcbzCStBu.

Example 1. Construction of *E. coli* Strains

A strain deficient in ompT (Protease 7) (defined as L31intact strain) and an L31short strain expressing $1^{st}$ to $62^{nd}$ amino acids from the N-terminus of the L31 protein were constructed. During the ribosome purification process, Protease 7 is known to degrade between the $62^{nd}$ and $63^{rd}$ amino acids of the L31 protein.

The *E. coli* strains were constructed according to the procedure for the Quick and Easy Conditional Knockout Kit (loxP/Cre) (Gene Bridges).

Preparation of Functional Cassettes with Added Homology Arms

A PCR reaction was performed with the Prime STAR HS DNA Polymerase (Takara Bio Inc., R010A) using the functional cassette loxP-PGK-gb2-neo-loxP (Gene Bridges, A003) as a template. The obtained PCR product was purified using the QIAquick PCR Purification Kit (QIAGEN, 28104). The concentration of the functional cassette was approximately 200 ng/μL. The functional cassette for preparing the ompT (Protease 7)-deficient strain—Cassette-1—was subjected to PCR using as primers, Oligol (SEQ ID NO: 3) and Oligo2 (SEQ ID NO: 4). The functional cassette for preparing the L31short strain—Cassette-2—was subjected to PCR using the primer set of Oligo3 (SEQ ID NO: 5) and Oligo4 (SEQ ID NO: 6).

Preparation of *Escherichia coli* Strains

*E. coli* strains were prepared according to the protocol described in the Quick and Easy Conditional Knockout Kit (loxP/Cre) (Gene Bridges). The *E. coli* W3110 strain (*Escherichia coli* K-12 W3110) was transformed with pRed/ET to prepare competent cells expressing Red/ET. The functional cassette, Cassette-1 or Cassette-2, was electroporated into the prepared competent cells to induce homologous recombination. Colony PCR was performed using the obtained colonies, and the introduction of the kanamycin cassette and the deletion or partial deletion of the gene of interest were confirmed from the length of the amplified DNA. By following the protocol described in the kit, the kanamycin resistance gene cassette sandwiched between Loxp sequences was deleted from the obtained *E. coli* strain of interest. Single colonies were prepared from the obtained *E. coli*, and target strain production was confirmed by sequencing the genomic DNA at the recombination site.

Example 2. Method for Preparing Ribosomes

Culturing of *E. coli*

The W3110 strain (WT) was cultured.

The bacterial cells of the W3110 strain were inoculated into a preculture medium (Glycerol 5 g/L, Yeast Extract 6 g/L, $KH_2PO_4$ 4 g/L, $K_2HPO_4$ 9.3 g/L) and precultured. The precultured bacterial cells were added to 30 L of the main culture medium (Glycerol 10 g/L, Yeast Extract 10 g/L, polypeptone N 15 g/L, $KH_2PO_4$ 4 g/L, $MgSO_4·7H_2O$ 2.4 g/L, $FeSO_4·7H_2O$ 0.04 g/L, $CaCl_2·2H_2O$ 0.04 g/L, Adecanol LG-109 0.24 g/L) so that $OD_{600}$ was 0.1. Culturing was carried out in a 50-L culture vessel. The cells were cultured at 37° C. for 5.4 hours and recovered when $OD_{600}$ reached 33.5. The culture solution was aliquoted into 500 mL and left to stand at room temperature for one hour and at 4° C. for another one hour. Thereafter, the mixture was centrifuged at 6000×g for 10 min, and the precipitate was suspended in D-PBS(−) (Takara Bio Inc., T9181) and then centrifuged again at 6000×g for 10 min. The recovered bacterial cells were frozen using liquid nitrogen and stored at −80° C.

Culturing of the L31Short Strain or the L31Intact Strain

LB medium, Miller (Nacalai Tesque, 20068-75) was used for culturing. The bacterial cells were precultured. The precultured bacterial cells were added to the main culture medium so that $OD_{600}$ was 0.05. Culturing was carried out by adding 1 L of LB medium to a 3-L baffled flask (Corning, 431253). Using the Climo-shaker ISF-1-X, the cells were cultured at 37° C. and at 100 rpm for approximately 2 hours and 40 min. After confirming that $OD_{600}$ reached approximately 1.0, the flask was removed from the incubator and left to stand at room temperature for one hour. Subsequently, the flask was left to stand at 4° C. for one hour. Bacterial cells were collected by centrifugation at 5000×g for 10 min. PBS (Takara Bio Inc., T9181) at a volume equivalent to the medium was used to suspend the bacterial cells, and then centrifugation was performed again at 5000×g for ten min. The bacterial cells were frozen using liquid nitrogen and stored at −80° C.

Disruption of *E. coli*

Disruption of the L31Intact Strain and the L31Short Strain Using FP

The recovered bacterial cells were suspended in 0.004 mL of Lysis Buffer (10 mM HEPES-KOH, pH 7.6, 5 mM to 10 mM $MgCl_2$, 50 mM KCl, 1 mM DTT, 10 μg/mL DNaseI) per 1 OD of the cells. The cells were disrupted using French Press (Emulsi Flex B15, AVESTIN). The pressure setting was at 40 Bar. The disruption speed was controlled to be approximately 1 mL/min. Centrifugation was performed at 20000×g for 30 min at 4° C., and the supernatant was collected.

Disruption of the WT Strain Using FP

Three types of Lysis Buffers having the following compositions were prepared:

Mg10 Lysis Buffer (10 mM HEPES-KOH, pH 7.6, 50 mM KCl, 10 mM $MgCl_2$, 1 mM DTT, 10 μg/mL DNaseI);

Mg5 Lysis Buffer (10 mM HEPES-KOH, pH 7.6, 50 mM KCl, 5 mM $MgCl_2$, 1 mM DTT, 10 μg/mL DNaseI); and Mg0 Lysis Buffer (10 mM HEPES-KOH, pH 7.6, 50 mM KCl, 1 mM DTT, 10 μg/mL DNaseI).

Using each Lysis Buffer, the bacterial cells were suspended in 0.004 mL of Lysis Buffer per 1 OD of recovered bacterial cells. The cells were disrupted using French Press (Emulsi Flex B15, AVESTIN). The pressure setting was at 40 Bar. The disruption speed was controlled to be approximately 1 mL/min. Centrifugation was performed at 20000×g for 30 min at 4° C., and the supernatant was collected.

Purification of *E. coli*

Ammonium Sulfate Precipitation of the L31Short Strain or the L31Intact Strain

To the supernatant of the solution of disrupted *E. coli,* 2× Buffer for ammonium sulfate precipitation (10 mM HEPES-KOH, pH 7.6, 5 mM to 10 mM $MgCl_2$, 50 mM KCl, 3.24 M ammonium sulfate, 1 mM DTT) was added, and the mixture was stirred at 4° C. for 30 min. This was subjected to centrifugation at 20000×g for 40 min at 4° C., and the supernatant was collected. The supernatant was filtered through a 0.22 μm (Millipore) filter.

Ammonium Sulfate Precipitation of the WT Strain

To 1 mL of the supernatant of the solution of disrupted *E. coli,* 0.222 g of ammonium sulfate finely crushed in a mortar was added while stirring with a stirrer. The mixture was stirred at 4° C. for 30 min. This was subjected to centrifugation at 20380×g for 40 min at 4° C., and the supernatant was collected. The supernatant was filtered through a 0.22 μm (Millipore) filter.

Butyl Sepharose Purification

An XK50 column (GE Healthcare, 28988952) packed with Butyl Sepharose 4 FastFlow (GE Healthcare, 17098002) was used. The solvent in the column was replaced with Buffer A (20 mM HEPES-KOH, pH 7.6, 10 mM $Mg(OAc)_2$, 1.5 M $(NH4)_2SO_4$, 1 mM DTT). A sample that had undergone ammonium sulfate precipitation was added to the column at 2 mL/min. The column was washed with Buffer A, and further washed with 30% Buffer A and 70% Buffer B (20 mM HEPES-KOH, pH 7.6, 10 mM $Mg(OAc)_2$, 1 mM DTT). Subsequently, the column was subjected to elution with 50% Buffer A and 50% Buffer B.

Ultracentrifugation Purification

30% sucrose Buffer (20 mM HEPES-KOH, pH 7.6, 10 mM $Mg(OAc)_2$, 30 mM $NH_4Cl$, 30% Sucrose, 1 mM DTT) was added in half the volume of the ultracentrifugation tube, and the eluent that had been purified by Butyl sepharose was added thereto so as not to disturb the interface. Centrifugation was performed at 99700×g for 20 hours at 4° C. The pellet was suspended in Storage Buffer (20 mM HEPES-KOH, pH 7.6, 6 mM $Mg(OAc)_2$, 30 mM KCl, 1 mM DTT).

The final concentration was adjusted to from 20 μM to 30 μM.

Finally, five ribosomes were prepared: L31short ribosome, L31intact ribosome, WT-10MG ribosome (using Mg10 Lysis Buffer), WT-5MG ribosome (using Mg5 Lysis Buffer), and WT-0MG ribosome (using Mg0 Lysis Buffer).

Example 3. Analysis of L31 Degradation Percentage

Degradation percentages of L31 in the WT-10MG ribosome, the WT-5MG ribosome, and the WT-0MG ribosome were analyzed.

Sample Preparation Method

The ribosome (40 μmol) was diluted with 38 μL of water. Trifluoroacetic acid was added at 1% to precipitate ribosomal RNA. Centrifugation was performed and the supernatant was mixed with a matrix (50% acetonitrile, 5 mg/mL sinapinic acid) at a 1:1 ratio, and crystallized by spotting 1 μL on a plate for MALDI/MS.

Analysis by MALDI/MS

Measurements were performed on a mass spectrometer (ABS CIEX·TOF/TOF 5800) using the Liner Positive mode. Calibration was carried out using the ribosomal protein as an internal standard. Correctly calibrated measurement results were used. The percentage of intact L31 was calculated by dividing the MS intensity of intact L31 by the sum of the MS intensity of intact L31 and the MS intensity of short L31. The measurement was carried out at N=3, and the average value was taken as the percentage of intact L31.

Result of Analyzing the L31 Degradation Rate

In the WT-10MG ribosome, 71% were intact L31. Similarly, in the WT-5MG ribosome, 20% were intact L31, and in the WT-0MG ribosome, 7% were intact L31.

Example 4. Synthesis of pCpA-Amino Acids (Also Called Aminoacyl-pCpAs) Used for Cell-Free Translation Systems Analysis conditions of LCMS were as follows.

TABLE 1

| Preparative condition | Instrument | Column (I.D. × length) (mm) | Mobile phase | Gradient (A/B) | Flow rate (mL/min) | Column temperature (° C.) | Wavelength |
|---|---|---|---|---|---|---|---|
| SQD FA05 | Acquity UPLC/SQD | Aldrich Ascentis Express C18 (2.1 × 50) | A) 0.1% FA, H2O B) 0.1% FA CH3CN | 95/5 => 0/100 (1.0 min ) => 0/100 (0.4 min) | 1.0 | 35 | 210-400 nm PDA total |

Synthesis of Pnaz-MeSer(tBuOH)-pCpA (TS01)
Compound TS01 was synthesized according to the following scheme.
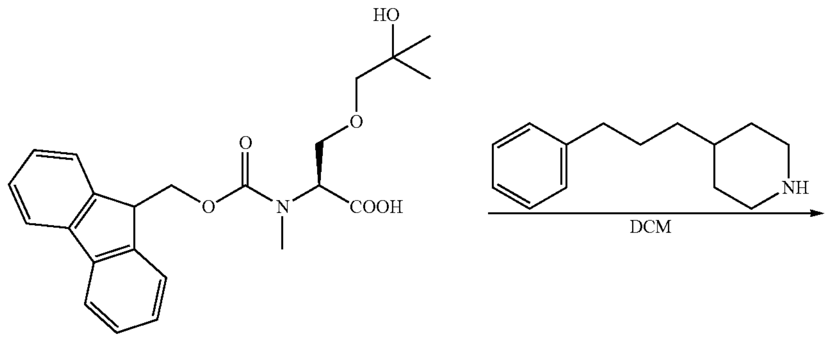
TS01-1
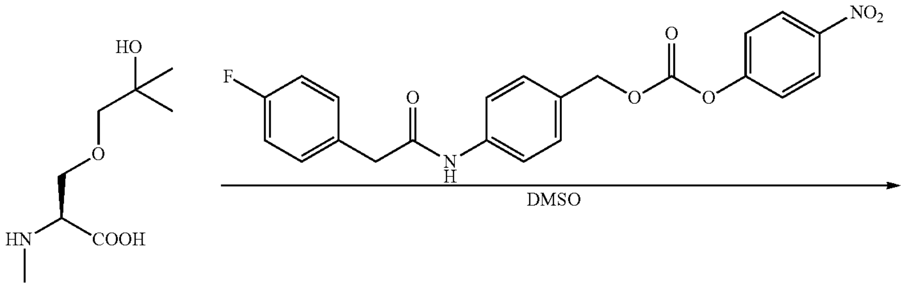
TS01-2
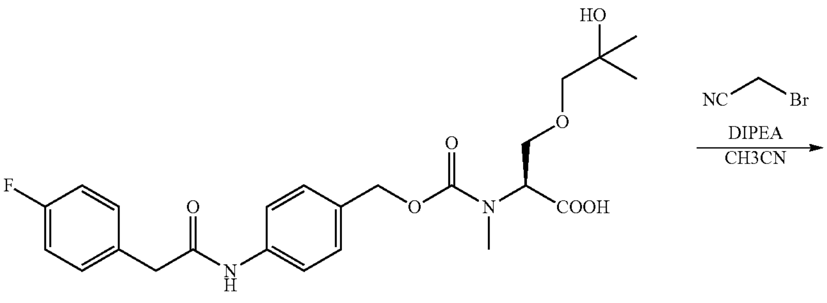
TS01-3

-continued
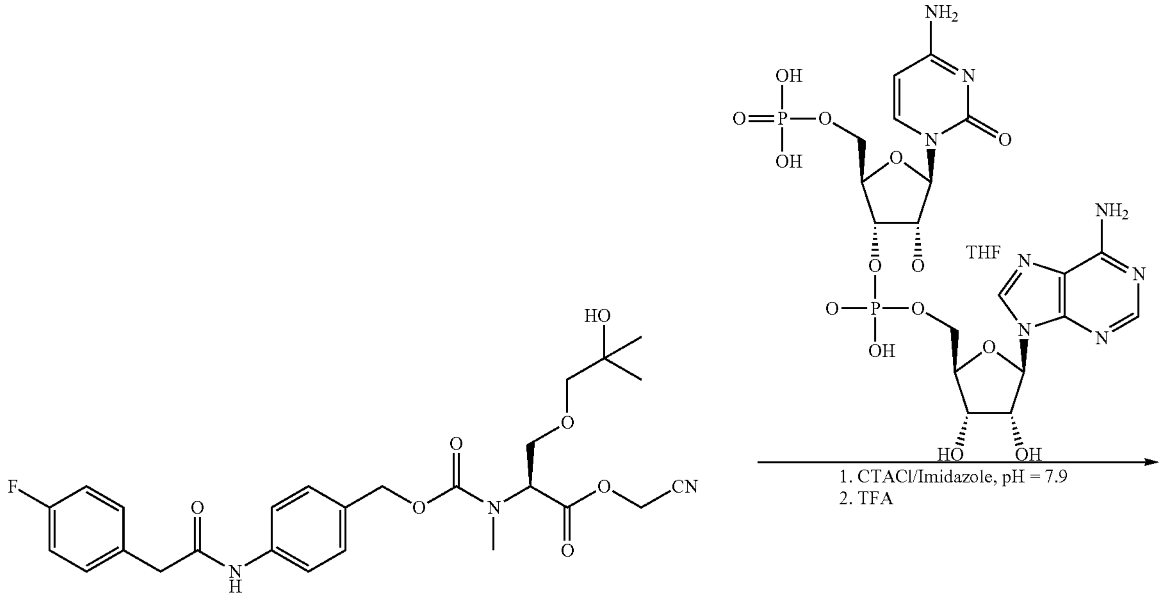
TS01-4
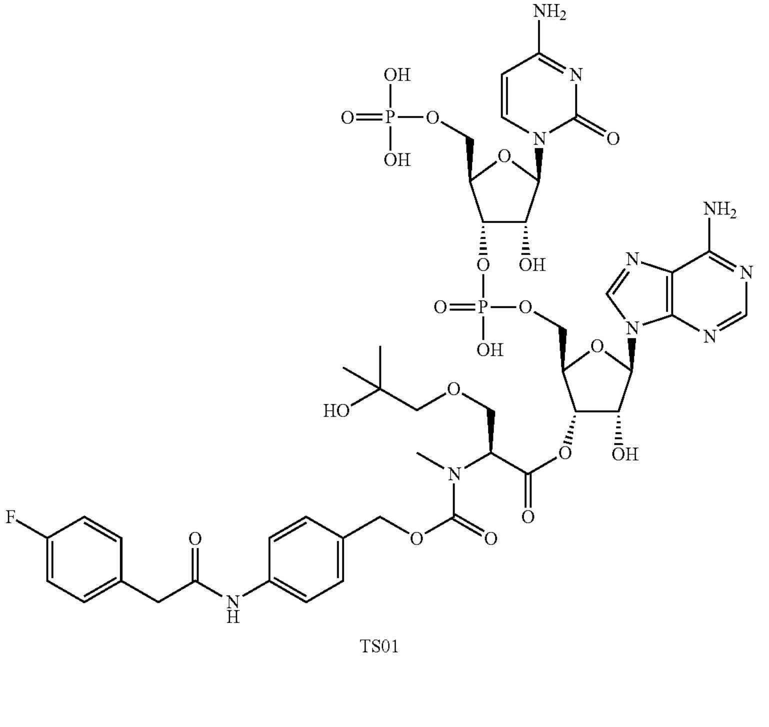
TS01

Synthesis of N-(((4-(2-(4-fluorophenyl)acetamide)benzyl)oxy)carbonyl)-O-(2-hydroxy-2-methylpropyl)-N-methyl-L-serine (TS01-3)

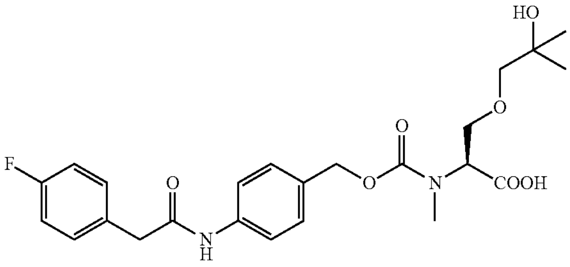 [SMILES: CN(C(=O)OCc1ccc(NC(=O)Cc2ccc(F)cc2)cc1)[C@@H](COCC(C)(C)O)C(=O)O]

(2S)-2-[[(9H-Fluoren-9-ylmethoxy)carbonyl](methyl)amino]-3-(2-hydroxy-2-methylpropxy)propanoic acid (TS01-1, 41.0 mg, 0.10 mmol) synthesized according to WO 2018225864 was dissolved in DCM (0.10 mL), 4-(3-phenylpropyl)piperidine (32.0 μL, 0.15 mmol) was added thereto, and this was stirred at room temperature for 15 hours. DCM was removed by concentration under reduced pressure to give (2S)-3-(2-hydroxy-2-methyl-propoxy)-2-(methylamino)propanoic acid (TS01-2) as a crude product. The obtained (2S)-3-(2-hydroxy-2-methyl-propoxy)-2-(methylamino)propanoic acid (TS01-2, crude product) and (4-nitrophenyl)-4-(2-(4-fluorophenyl)acetamide benzyl carbonate (110.0 mg, 0.26 mmol) synthesized according to WO 2018225864 were dissolved in DMSO (0.50 mL), triethylamine (41.8 μL, 0.30 mmol) was added, and then this was stirred at 50° C. for one hour. The reaction solution was purified by reverse-phase column chromatography (0.1% FA in $H_2O$/0.1% FA in $CH_3CN$) to give the title compound (TS01-3, 40 mg, 84%).

LCMS (ESI) m/z=475.4 (M−H)−

Retention time: 0.64 min (analysis condition SQDFA05)

Synthesis of cyanomethyl N-(((4-(2-(4-fluorophenyl)acetamide)benzyl)oxy)carbonyl)-O-(2-hydroxy-2-methylpropyl)-N-methyl-L-serinate (TS01-4)

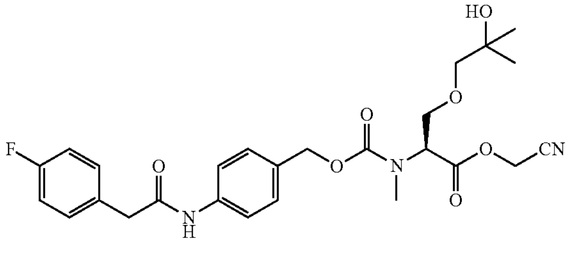 [SMILES: CN(C(=O)OCc1ccc(NC(=O)Cc2ccc(F)cc2)cc1)[C@@H](COCC(C)(C)O)C(=O)OCC#N]

N-(((4-(2-(4-Fluorophenyl)acetamide)benzyl)oxy)carbonyl)-O-(2-hydroxy-2-methylpropyl)-N-methyl-L-serine (TS01-3, 19.0 mg, 0.04 mmol) was dissolved in $CH_3CN$ (0.20 mL), then DIPEA (10.48 μL, 0.06 mmol) and 2-bromoacetonitrile (3.22 μL, 0.048 mmol) were added thereto, and this was stirred at room temperature for 12 hours. The reaction solution was concentrated under reduced pressure to give the title compound (TS01-4) as a crude product.

LCMS (ESI) 514 (M−H)−

Retention time: 0.73 min (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl N-(((4-(2-(4-fluorophenyl)acetamide)benzyl)oxy)carbonyl)-O-(2-hydroxy-2-methylpropyl)-N-methyl-L-serinate (TS01)

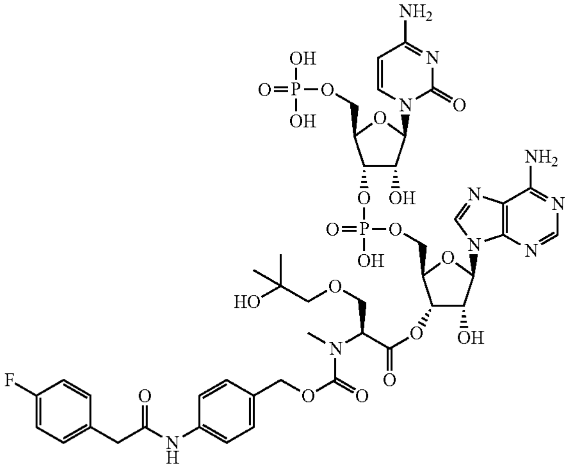 [SMILES: CN(C(=O)OCc1ccc(NC(=O)Cc2ccc(F)cc2)cc1)[C@@H](COCC(C)(C)O)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (28.9 mg, 0.04 mmol) synthesized by the method described in the literature (Helv. Chim. Acta, 90, 297-310) was dissolved in Buffer A (10 mL), a solution of cyanomethyl N-(((4-(2-(4-fluorophenyl)acetamide)benzyl)oxy)carbonyl)-O-(2-hydroxy-2-methylpropyl)-N-methyl-L-serinate (TS01-4, crude product) in acetonitrile (0.021 mg, 0.04 mmol, 0.50 mL) was added dropwise thereto, and this was stirred at room temperature for 60 min. The reaction solution was cooled to 0° C., and then trifluoroacetic acid (0.50 mL) was added. The reaction solution was stirred at 0° C. for 60 min, and then purified by reverse-phase silica gel column chromatography (0.05% aqueous trifluoroacetic acid solution/0.05% trifluoroacetic acid-acetonitrile) to give the title compound (TS01, 8.0 mg, 18.0%).

LCMS (ESI) m/z=1109.7 (M−H)−

Retention time: 0.50 min (analysis condition SQDFA05)

Buffer A was prepared as follows.

Acetic acid was added to an aqueous solution of N,N,N-trimethylhexadecan-1-aminium chloride (6.40 g, 20 mmol) and imidazole (6.81 g, 100 mmol) to give Buffer A (1 L), which was 20 mM N,N,N-trimethylhexadecan-1-aminium and 100 mM imidazole at pH 7.9.

Synthesis of BdpFL-(4-AMF)-pCpA (MT01)

Synthesis of (2S)-3-[4-(aminomethyl)phenyl]-2-[[4-[[2-(4-fluorophenyl)acetyl]amino]phenyl]methoxycarbonylamino]propanoic acid (Compound MT02)

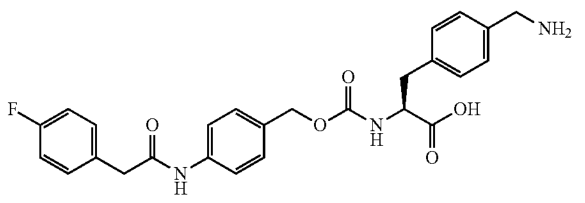 [SMILES: NCc1ccc(C[C@H](NC(=O)OCc2ccc(NC(=O)Cc3ccc(F)cc3)cc2)C(=O)O)cc1]

Under a nitrogen atmosphere, a solution of 4N HCl in 1,4-dioxane was added to a suspension of (2S)-3-[4-(aminomethyl)phenyl]-2-[[4-[[2-(4-fluorophenyl)acetyl]amino]phenyl]methoxycarbonylamino]propanoic acid (500 mg, 0.968 mmol) in dichloromethane (4.5 mL) at room temperature. After stirring the mixture for one hour at room temperature, the solvent was distilled off under reduced pressure. DIPEA (413 mg, 3.19 mmol) was added to a suspension of the obtained residue and [4-[[2-(4-fluorophenyl)acetyl]amino]phenyl]methyl (4-nitrophenyl) carbonate (411 mg, 0.968 mmol) in DMSO (5 mL) at room temperature. After stirring the mixture for two hours at room temperature, piperidine (400 mg, 4.7 mmol) was added thereto at room temperature, and this was stirred for 15 min. The reaction solution was purified by reverse-phase column chromatography (0.1% FA $CH_3CN/H_2O$) to give (2S)-3-[4-(aminomethyl)phenyl]-2-[[4-[[2-(4-fluorophenyl)acetyl]amino]phenyl]methoxycarbonylamino]propanoic acid (Compound MT02) (83.3 mg, 18% yield, 3 steps).

LCMS (ESI) m/z=480.3 (M+H)+

Retention time: 0.46 min (analysis condition SQDFA05)

Synthesis of (S)-3-(4-((3-(5,5-difluoro-7,9-dimethyl-5H-4$\lambda^4$,5$\lambda^4$-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid (Compound MT03)

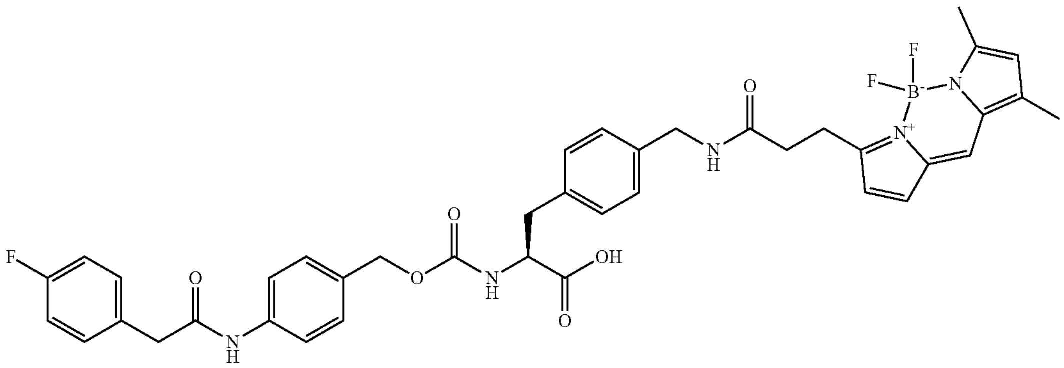 [SMILES: Cc1cc(C)n2c1C=C1C=CC(CCC(=O)NCc3ccc(C[C@H](NC(=O)OCc4ccc(NC(=O)Cc5ccc(F)cc5)cc4)C(=O)O)cc3)=[N+]1[B-]2(F)F]

Under a nitrogen atmosphere, a solution of 3-(3-((2,5-dioxopyrrolidin-1-yl)oxy)-3-oxopropyl)-5,5-difluoro-7,9-dimethyl-5H-5$\lambda^4$-dipyrrolo[1,2-c:2',1'-f][1,3,2]diazaborinin-4-ium in NMP (500 mL) was added to a solution of (2S)-3-[4-(aminomethyl)phenyl]-2-[[4-[[2-(4-fluorophenyl)acetyl]amino]phenyl]methoxycarbonylamino]propanoic acid (Compound MT02) (11.8 mg, 0.030 mmol) in NMP (500 mL) at room temperature. After stirring the mixture at 40° C. for ten min, the reaction solution was purified by reverse-phase column chromatography (0.1% FA $CH_3CN/H_2O$) to give (S)-3-(4-((3-(5,5-difluoro-7,9-dimethyl-5H-4$\lambda^4$,5$\lambda^4$-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid (Compound MT03) (14.6 mg, 64% yield).

LCMS (ESI) m/z=752.2 (M−H)−

Retention time: 0.79 min (analysis condition SQDFA05)

Synthesis of (S)-3-(4-((3-(5,5-difluoro-7,9-dimethyl-5H-4λ[4],5λ[4]-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid cyanomethyl ester (Compound MT04)

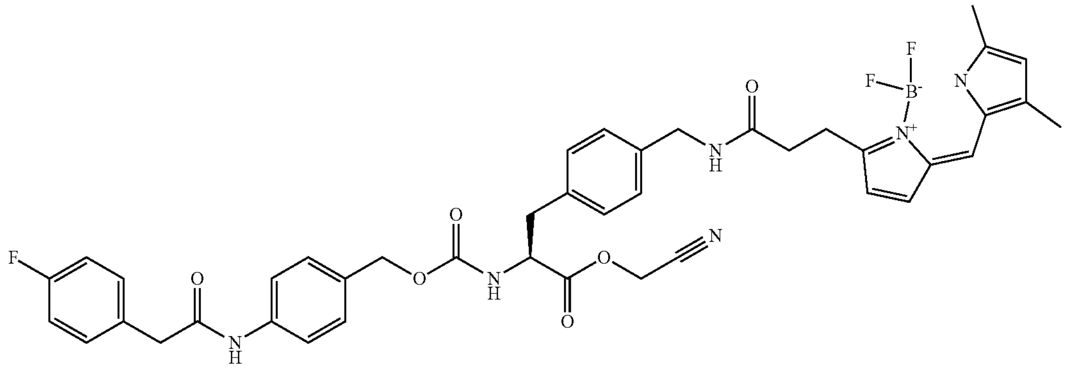

Under a nitrogen atmosphere, (S)-3-(4-((3-(5,5-difluoro-7,9-dimethyl-5H-4λ[4],5λ[4]-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid (50 mg, 0.066 mmol) and N-ethyl-isopropylpropan-2-amine (DIPEA) (23.2 μL, 0.133 mmol) were dissolved in acetonitrile (200 μL), 2-bromoacetonitrile (9.0 μL, 0.133 mmol) was added thereto at 0° C., and this was stirred at 40° C. for 3.5 hours. The reaction solution was concentrated to give (S)-3-(4-((3-(5,5-difluoro-7,9-dimethyl-5H-4λ[4],5λ[4]-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid cyanomethyl ester (Compound MT04) as a crude product. The obtained crude product was directly used in the next step.

LCMS (ESI) 791.4 (M−H)−

Retention time: 0.90 min (analysis condition SQDFA05)

Synthesis of [(2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl] (2S)-3-(4-((3-(5,5-difluoro-7,9-dimethyl-5H-4λ[4],5λ[4]-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoate (Compound MT01, BdpFL-(4-AMF)-pCpA)

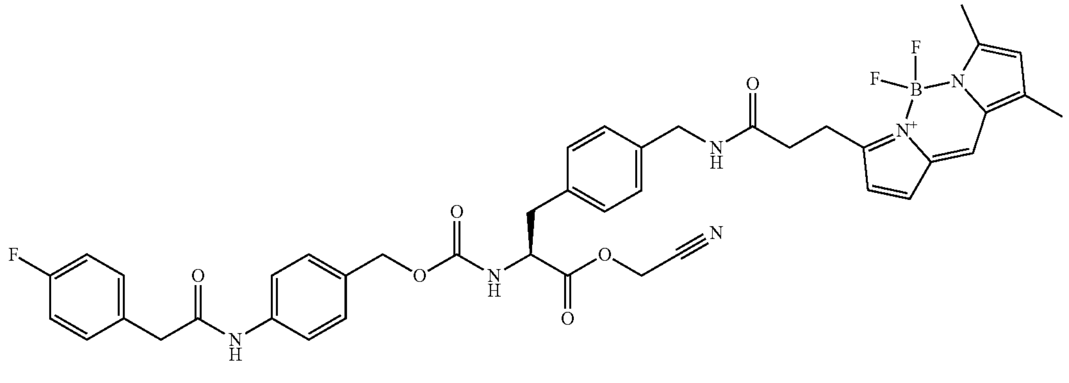

+

-continued

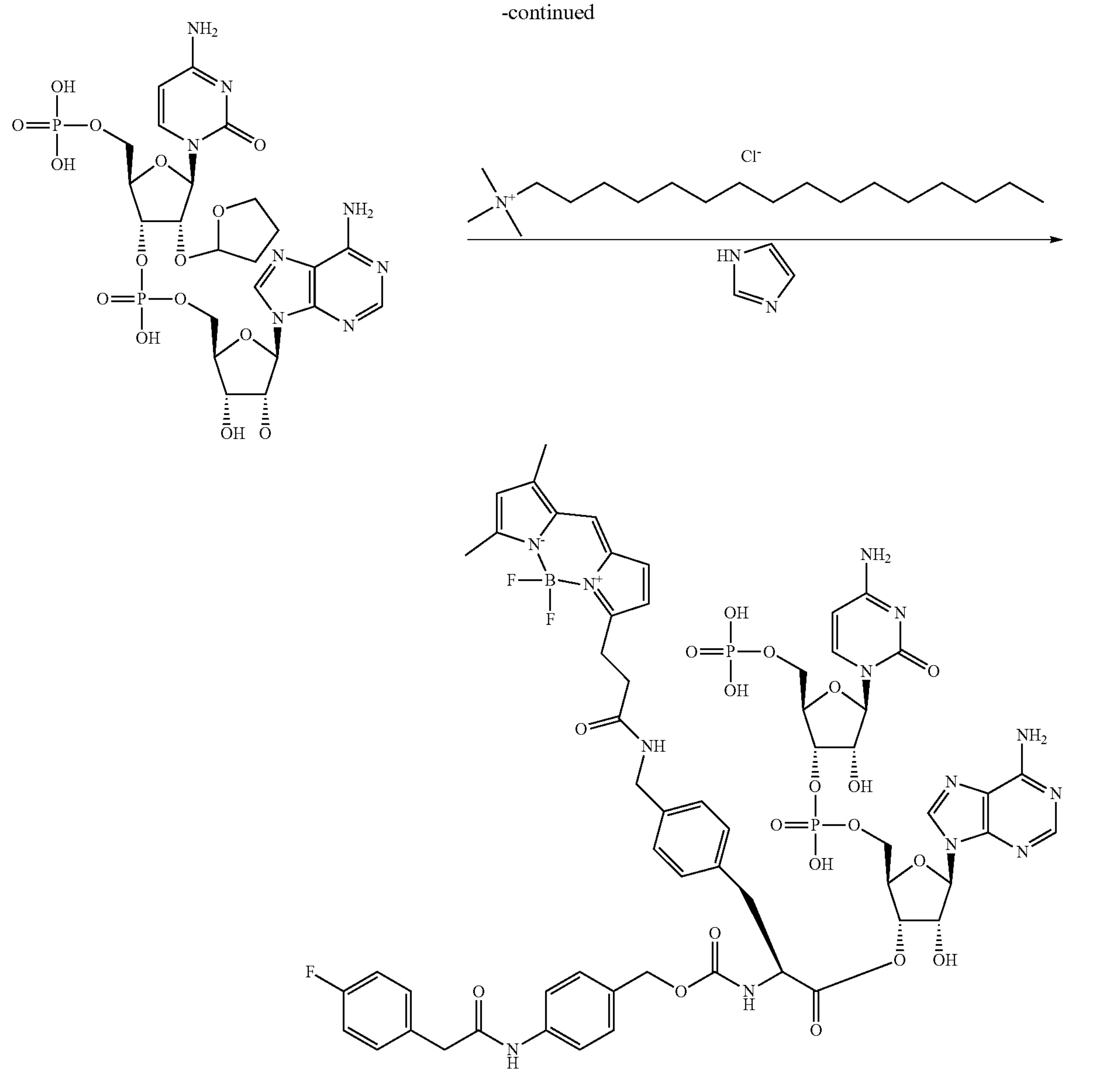

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (47.7 mg, 0.066 mmol) was dissolved in Buffer A (55 mL), and a solution of (S)-3-(4-((3-(5,5-difluoro-7,9-dimethyl-5H-4$\lambda^4$,5$\lambda^4$-dipyrrolo[1,2-c:2',1'-f][1,3,2]diazaborinin-3-yl)propanamide)methyl)phenyl)-2-((((4-(2-(4-fluorophenyl)acetamide)benzyl)oxy)carbonyl)amino)propanoic acid cyanomethyl ester (Compound MT04) (52.3 mg, 0.066 mmol) in acetonitrile (5 mL) was added thereto in three portions, and the mixture was then stirred at room temperature for 90 min. TFA (3 mL) was added to the reaction solution at 0° C., this was stirred for five min, and then stirred at room temperature for 40 min. The reaction solution was purified by reverse-phase silica gel column chromatography (0.05% TFA $CH_3CN/H_2O$) to give the title compound (Compound MT01, BdpFL-(4-AMF)-pCpA) (8.3 mg, 9.1% yield).

LCMS (ESI) m/z=1386.7 (M−H)−

Retention time: 0.65 min (analysis condition SQDFA05)

Example 5. Synthesis of Aminoacyl-tRNA

Sequences of tRNAGlu(-CA)s

The following tRNAGluCUU(-CA) was prepared by a conventional method.

```
Sequence TR-1 (SEQ ID NO: 7)
tRNAGluCUU(-CA) RNA sequence:
GUCCCCUUCGUCUAGAGGCCCAGGACACCGCCCUCUUACGGCGGUAA

CAGGGGUUCGAAUCCCCUAGGGGACGC

p
```

The following tRNAGluCUG(-CA) was prepared by a conventional method.

```
Sequence TR-2 (SEQ ID NO: 8)
tRNAGluCUG(-CA) RNA sequence:
GUCCCCUUCGUCUAGAGGCCCAGGACACCGCCCUCUGACGGCGGUAA

CAGGGGUUCGAAUCCCCUAGGGGACGC
```

The following tRNAfMet(CAU)(-CA) was prepared by a conventional method.

```
Sequence TR-3
                                    (SEQ ID NO: 9)
GGCGGGGUGGAGCAGCCUGGUAGCUCGUCGGGCUCAUAACCCGAAGA

UCGUCGGUUCAAAUCCGGCCCCCGCAAC
```

Synthesis of Aminoacyl-tRNA Using Aminoacyl-pCpA: Part 1

10× Ligation buffer (500 mM HEPES-KOH pH 7.5, 200 mM $MgCl_2$) (4 μL), 10 mM ATP (4 μL), and Nuclease free water (5.6 μL) were added to 50 μM transcribed tRNA-GluCUG(-CA) (SEQ ID NO: 8) (20 μL), the mixture was heated at 95° C. for two min and then left to stand at room temperature for five min for tRNA refolding. Ten units/μL T4 RNA ligase (New England Biolabs) (2.4 μL) and a 2.5 mM solution of aminoacyl-pCpA (TS01) in DMSO (4 μL) were added thereto, and ligation reaction was carried out at 16° C. for 45 min. Sodium acetate was added to the ligation reaction solution at a final concentration of 0.3 M, phenol-chloroform extraction was carried out, and aminoacyl-tRNA (Compound AAtR-1) was recovered by ethanol precipitation. The recovered aminoacyl-tRNA (Compound AAtR-1) was dissolved in 1 mM sodium acetate immediately prior to addition to a mixture for translation.

Compound AAtR-1

MeSer(tBuOH)-tRNAGluCUG

Synthesis of Aminoacyl-tRNA Using Aminoacyl-pCpA: Part 2

10× Ligation buffer (500 mM HEPES-KOH pH 7.5, 200 mM $MgCl_2$) (4 μL), 10 mM ATP (4 μL), and Nuclease free water (5.6 μL) were added to 50 μM transcribed tRNA-GluCUU(-CA) (SEQ ID NO: 7) (20 μL), the mixture was heated at 95° C. for two min and then left to stand at room temperature for five min for tRNA refolding. Ten units/μL T4 RNA ligase (New England Biolabs) (2.4 μL) and a 2.5 mM solution of aminoacyl-pCpA (MT01) in DMSO (4 μL) were added thereto, and ligation reaction was carried out at 16° C. for 45 min. Sodium acetate was added to the ligation reaction solution at a final concentration of 0.3 M, phenol-chloroform extraction was carried out, and aminoacyl-tRNA (Compound AAtR-2) was recovered by ethanol precipitation. The recovered aminoacyl-tRNA (Compound AAtR-2) was dissolved in 1 mM sodium acetate immediately prior to addition to a mixture for translation.

Compound AAtR-2

BODIPYFL-4-AMF-tRNAGluCUU

Synthesis of Aminoacyl-tRNA Using Aminoacyl-pCpA: Part 3

10× Ligation buffer (500 mM HEPES-KOH pH 7.5, 200 mM $MgCl_2$) (4 μL), 10 mM ATP (4 μL), and Nuclease free water (5.6 μL) were added to 50 μM transcribed tRNAfMet-CAU(-CA) (SEQ ID NO: 9) (20 μL), the mixture was heated at 95° C. for two min and then left to stand at room temperature for five min for tRNA refolding. Ten units/μL T4 RNA ligase (New England Biolabs) (2.4 μL) and a 2.5 mM solution of (Acbz-MeCys(StBu)-pCpA (Compound nk14 described in Patent Literature WO 2017150732) in DMSO (4 μL) were added thereto, and ligation reaction was carried out at 16° C. for 45 min. 0.3 M Sodium acetate was added to the ligation reaction solution, phenol-chloroform extraction was carried out, and aminoacyl-tRNA (Compound AAtR-3) was recovered by ethanol precipitation. The recovered aminoacyl-tRNA (Compound AAtR-3) was dissolved in 1 mM sodium acetate immediately prior to addition to a mixture for translation.

Compound AAtR-3

Acbz-MeCys(StBu)-tRNAfMetCAU

Example 6. Synthesis of LCT12

Synthesis of (2S,3R)-2-((((9H-fluoren-9-yl)methoxy)carbonyl)amino)-3-((tetrahydro-2H-pyran-2-yl)oxy)butanoic acid (Fmoc-Thr(THP)-OH) for use in peptide synthesis of LCT-12 by a peptide synthesizer

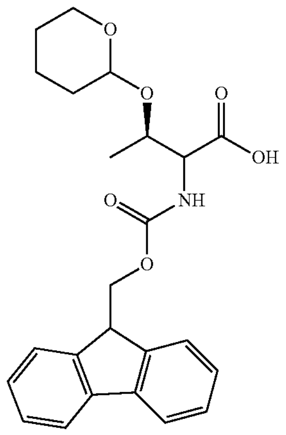 [SMILES: C[C@@H](OC1CCCCO1)C(NC(=O)OCC1c2ccccc2-c2ccccc21)C(=O)O]

Toluene (50 mL) was added to a mixture of (2S,3R)-2-((((9H-fluoren-9-yl)methoxy)carbonyl)amino)-3-hydroxybutanoic acid monohydrate (Fmoc-Thr-OH monohydrate, purchased from Tokyo Chemical Industry, 5.0 g, 13.9 mmol) and pyridinium p-toluenesulfonate (PPTS, 0.175 g, 0.70 mmol), and the included moisture was removed azeotropically by distilling off toluene under reduced pressure. To the resulting residue, ultra-dehydrated tetrahydrofuran (THF, 28 mL) and 3,4-dihydro-2H-pyran (8.8 mL, 97 mmol) were added, and under a nitrogen atmosphere, this mixture was stirred at 50° C. for four hours. After confirming disappearance of the raw materials by LCMS (SQDFA05), the mixture was cooled to 25° C., and ethyl acetate (30 mL) was added. The organic layer was then washed by adding a saturated aqueous sodium chloride solution (30 mL), and the aqueous layer was extracted with ethyl acetate (30 mL). All the resulting organic layers were combined and further washed twice with a saturated aqueous sodium chloride solution (30 mL). The organic layers were dried over sodium sulfate and the solvent was distilled off under reduced pressure to give a crude product (9.3 g).

Dissolution of 4.65 g of the resulting crude product in tetrahydrofuran (THF, 30 mL) was followed by addition of 1.0 M phosphate buffer adjusted to pH 8.0 (30 mL). This mixture was stirred at 50° C. for four hours. After cooling the mixture to 25° C., ethyl acetate (30 mL) was added thereto and the organic layer and the aqueous layer were separated. The aqueous layer was extracted by adding ethyl acetate (30 mL), and then all the resulting organic layers were combined and washed twice with a saturated aqueous sodium chloride solution (30 mL). The organic layers were dried over sodium sulfate, the solvent was distilled off under reduced pressure, and the residue was further dried under reduced pressure using a pump at 25° C. for 30 min.

The resulting residue was dissolved in diethyl ether (50 mL), and then heptane (50 mL) was added. Under controlled reduced pressure (approximately 100 hPa), only the diethyl ether was distilled off and the resulting mixture was filtered to give a solid. This washing operation with heptane was repeated twice. The resulting solid was dried under reduced pressure using a pump at 25° C. for two hours to give a sodium salt of Fmoc-Thr(THP)-OH (2.80 g, 6.26 mmol).

Ethyl acetate (50 mL) and 0.05 M aqueous phosphoric acid solution at pH 2.1 (140 mL) were added to the total amount of the resulting sodium salt of Fmoc-Thr(THP)-OH, this was stirred at 25° C. for five min, and then the organic layer and the aqueous layer were separated. The aqueous layer was extracted by adding ethyl acetate (50 mL), and then all the resulting organic layers were combined and washed twice with a saturated aqueous sodium chloride solution (50 mL). The organic layers were dried over sodium sulfate and the solvent was distilled off under reduced pressure. The residue was dried under reduced pressure using a pump at 25° C. for two hours, the resulting solid was then dissolved in t-butyl methyl ether (TBME, 50 mL), and the solvent was distilled off under reduced pressure. Further drying under reduced pressure using a pump at 25° C. for one hour gave (2S,3R)-2-((((9H-fluoren-9-yl)methoxy)carbonyl)amino)-3-((tetrahydro-2H-pyran-2-yl)oxy)butanoic acid (Fmoc-Thr(THP)-OH, 2.70 g, with residual 30 mol % of t-butyl methyl ether (TBME)) as diastereomers derived from the asymmetric carbon of THP protecting group. The obtained Fmoc-Thr(THP)-OH was stored in a freezer at −25° C.

LCMS (ESI) m/z=424.2 (M−H)−

Retention time: 0.84 min, 0.85 min (analytical condition SQDFA05_01)

Synthesis of a Peptide (LCT-12) Carrying BdpFL at its N-Terminus for Use as a Standard Sample in LC/MS

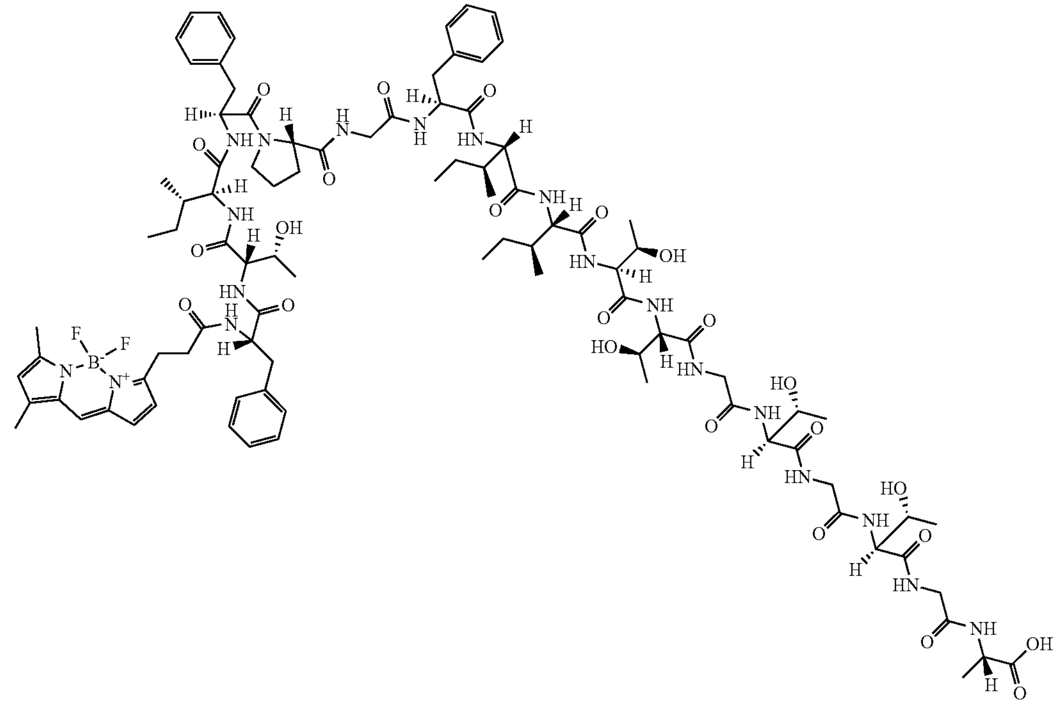 [SMILES: CC[C@H](C)[C@H](NC(=O)[C@H](Cc1ccccc1)NC(=O)CNC(=O)[C@@H]1CCCN1C(=O)[C@H](Cc1ccccc1)NC(=O)[C@@H](NC(=O)[C@@H](NC(=O)[C@H](Cc1ccccc1)NC(=O)CCC1=[N+]2C(=Cc3c(C)cc(C)n3[B-]2(F)F)C=C1)[C@@H](C)O)[C@@H](C)CC)C(=O)N[C@H](C(=O)N[C@H](C(=O)N[C@H](C(=O)NCC(=O)N[C@H](C(=O)NCC(=O)N[C@H](C(=O)NCC(=O)N[C@@H](C)C(=O)O)[C@@H](C)O)[C@@H](C)O)[C@@H](C)O)[C@@H](C)O)[C@@H](C)CC]

Using 2-chlorotrityl resin (100 mg) loaded with Fmoc-Ala-OH, peptide elongation was performed on a peptide synthesizer using Fmoc-Gly-OH, Fmoc-Thr(THP)-OH, Fmoc-Ile-OH, Fmoc-Phe-OH, and Fmoc-Pro-OH as Fmoc amino acids. Peptide elongation was performed by following the peptide synthesis method by the Fmoc method (WO 2013100132 B2). After performing the peptide elongation, the Fmoc group at the N-terminus was removed on the peptide synthesizer, and then the resin was washed with DCM.

TFE/DCM (1:1, v/v, 2 mL) was added to the resin, and this was shaken for one hour to cleave the peptide from the resin. After completion of the reaction, the solution in the tube was filtered through a synthesis column to remove the resin, and the resin was washed twice with TFE/DCM (1:1, v/v, 1 mL). All the extracted solutions were combined, DMF (2 mL) was added, and then this was concentrated under reduced pressure. The resulting residue was dissolved in NMP (0.5 mL), 1/4 (125 μL) of this solution was used for the next reaction. BdpFL succinimide ester adjusted to 76.5 mM (140 μL) was added to the peptide solution in NMP at room temperature, and after stirring this overnight at 40° C., it was concentrated under reduced pressure. The resulting residue was dissolved in 0.05 M tetramethylammonium hydrogen sulfate in HFIP (1.2 mL, 0.060 mmol), and this was stirred at room temperature for two hours. The reaction solution was purified by reverse-phase silica gel column chromatography (0.1% FA MeCN/$H_2O$) to give the title compound (LCT-12c (0.3 mg). The amino acid sequence of LCT-12 is shown in SEQ ID NO: 17.

LCMS (ESI) m/z=1972.9 (M−H)−

Retention time: 0.74 min (analysis condition SQDFA05_01)

Example 7. Ribosomal Synthesis of Peptides

Overview of Experiment 1

An experiment was conducted to compare the translation properties of two ribosomes—the ribosome prepared from the L31intact strain (L31intact ribosome) and the ribosome prepared from the L31short strain (L31short ribosome).

Specifically, peptide compounds were ribosomally synthesized by allowing translation of a template mRNA, which is Sequence mR-1 (SEQ ID NO: 10) or Sequence mR-2 (SEQ ID NO: 11), using Compounds AAtR-1, AAtR-2, and Initiator-tRNA (AAtR-3). The design was such that Acbz-MeCys(StBu):MeSer(tBuOH):MePhe:Ile:Ile:Gly:MePhe:BODIPYFL-4-AMF:Ile:Ile:Pro:Ile:Gly (SEQ ID NO: 14) will be translated from mR-1 and Acbz-MeCys(StBu):T:MePhe:Ile:Ile:Gly:MePhe:BODIPYFL-4-AMF:Ile:Ile:Pro:Ile:Gly (SEQ ID NO: 16) will be translated from mR-2 as the translation product. Hereinafter, amino acids will be presented with a colon separating them.

The target molecules (TM) and by-products were quantified using LC-MS. The main by-products observed were the Initiation Read-through (iRT) peptides whose translation was initiated from the amino acid represented by the third letter from the initial amino acid.

Translation Condition

The translation system used was the PURE system, a reconstituted cell-free protein synthesis system derived from prokaryotes. Specifically, a translation solution contained the following: 1 mM GTP, 1 mM ATP, 20 mM creatine phosphate, 50 mM HEPES-KOH pH 7.6, 100 mM potassium acetate, 2 mM spermidine, 1 mM dithiothreitol, 1.0 mg/mL *E. coli* MRE600 (RNase negative)-derived tRNA (Roche) (some tRNAs had been removed by the method of the non-patent literature (Yokogawa T, Kitamura Y, Nakamura D, Ohno S, Nishikawa K. 2010. Nucleic acids research 38:e89)), 3 μM in vitro transcribed *E. coli* tRNA Ala1B, 0.26 μM EF-G, 4 μg/mL creatine kinase, 3 μg/mL myokinase, 2 units/mL inorganic pyrophosphatase, 1.1 μg/mL nucleoside diphosphate kinase, 2.7 μM IF1, 0.4 μM IF2, 1.5 μM IF3, 40 μM EF-Tu, 35 μM EF-Ts, 1 μM EF-P-Lys, 0.4 units/μL RNasin Ribonuclease inhibitor (Promega, N2111), 0.4 μM to 0.5 μM Penicillin G Amidase (PGA), 2.7 μM AlaRS, 1 μM GlyRS, 0.4 μM IleRS, 0.5 μM mutant PheRS (WO 2016/148044), 0.16 μM ProRS, 0.09 μM ThrRS, 1 μM mutant ValRS (WO 2016/148044), 1 μM mutant SerRS (WO 2016/148044), 250 μM Gly, 250 μM Lys, 100 μM Ile, 250 μM Pro, 250 μM Thr, 5 mM N-methylalanine, 5 mM N-methylphenylalanine, 5 mM N-methylserine, and 5 mM N-methylvaline. Magnesium acetate was prepared at four concentrations, 2 mM, 4 mM, 6 mM, and 8 mM, initiator aminoacyl-tRNA (Compound AAtR-3) was added at 25 μM, and each of the aminoacyl-tRNAs including Compounds AAtR-1 and AAtR-2 was added at 10 μM to the translation reaction mixture. Furthermore, mRNA (mR-1 or mR-2) was added at 1 μM to the translation reaction mixture. The mixture contained 185 μM aminoacyl-tRNAs not used for translation. Translation was performed by adding the L31short ribosome or the L31intact ribosome at 1.2 μM, and leaving the mixture to stand at 37° C. for one hour. Thereafter, the mixture was heated at 95° C. for three min and then left to stand until it reached at room temperature. Peptidyl-tRNA hydrolase (Pth) was added at 8.58 μM and the mixture was left to stand at 37° C. for one hour.

Preparation of mRNA

Template mRNA, Sequence mR-1 or Sequence mR-2, was synthesized from a template DNA (SEQ ID NO: 12 or 13) by in vitro transcription reaction using the RiboMAX Large Scale RNA production System T7 (Promega, P1280) and purified with the RNeasy Mini kit (Qiagen).

Outline of the Analysis

A solution that contained a peptide translation product comprising unnatural amino acids was diluted ten-fold and analyzed using an LC-FLR-MS instrument. For the analytical data, the retention time of the translated peptide of interest was determined from the MS data, and the amount of translated peptide was evaluated by quantifying the fluorescence peak of the corresponding retention time. For the quantitative evaluation, a calibration curve was prepared using the LCT12 synthesized in Example 6 as a standard, and the content was calculated by relative quantitation. LC-MS was performed under the following analysis conditions.

Analysis Conditions

TABLE 2

| | |
|---|---|
| Instrument | Aquity UPLC-FLR-Xevo G2-XS Tof or UPLC-LCT |
| Column | waters BEHC18 (2.1 × 50 mm, ϕ1.7 μm) |
| Mobile phase | A = 0.1% FA with H2O<br>B = 0.1% FA with CH3CN |
| Gradient (% B) | 0-0.2 min = 10%<br>0.2-3.6 min = 98%<br>3.6-4.0 min = 10% |
| Flow rate (mL/min) | 0.5 |
| Column temperature | 40 |
| Fluorescence measurement wavelength (Ex/Em) | 491 nm/515 nm |
| Ms mode | ESI− |

Results

In both translation experiments of the mRNA sequences—mR-1 and mR-2—at the optimum Mg concentration for each ribosome, the translated amount of the target molecule was greater when translated with the L31short ribosome than when translated with the L31intact ribosome.

In both translations of the mRNA sequences—mR-1 and mR-2—at the optimum Mg concentration for each ribosome, the ratio of the amount of the translated iRT peptide, which was a by-product, to the target molecule was lower when using the L31short ribosome than when using the L31intact ribosome.

Compared to the sequence of mR-2, whose second letter from the initial amino acid is Thr, the sequence of mR-1, having MeSer(tBuOH) at the same position, showed greater effect of improving the amount of the target molecule translated by the L31short ribosome at the optimum $Mg^{2+}$ concentration.

This showed the usefulness of using the L31short ribosome prepared from the L31short strain when performing translation using the Initiation Suppression (iSup) method.

The amount of the translated target molecule and the amount of the iRT peptide translated when translation was performed from the mR-1 sequence and mR-2 sequence using the L31short ribosome or the L31intact ribosome are shown below.

TABLE 3-1

| Ribosome | mRNA sequence | Mg concentration | Translation product | Translation amount (nM) |
|---|---|---|---|---|
| L31short ribosome | mR-1 | 2 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 10.2 |
| | | 4 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 36.9 |
| | | 6 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 26.8 |
| | | 8 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 15.7 |
| L31intact ribosome | | 2 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 6.8 |
| | | 4 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 10.7 |
| | | 6 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 8.0 |
| | | 8 | Acbz-MeCys (StBu):MeSer (tBuOH):MePhe:Ile:Ile:Gly:MePhe:BODIPYFL-4-AMF:Ile:Ile:Pro:Ile:Gly (SEQ ID NO: 14) | 2.6 |

TABLE 3-2

| Ribosome | mRNA sequence | Mg concentration | Translation product | Translation amount (nM) |
|---|---|---|---|---|
| L31short ribosome | mR-1 | 2 | MePhe:Ile:Ile:Gly:MePhe:BODIPYFL-4-AMF:Ile:Ile:Pro:Ile:Gly (SEQ ID NO: 15) | 0.3 |
| | | 4 | MePhe:Ile:Ile:Gly:MePhe:BODIPYFL-4-AMF:Ile:Ile:Pro:Ile:Gly (SEQ ID NO: 15) | 22.1 |
| | | 6 | MePhe:Ile:Ile:Gly:MePhe:BODIPYFL-4-AMF:Ile:Ile:Pro:Ile:Gly (SEQ ID NO: 15) | 48.1 |
| | | 8 | MePhe:Ile:Ile:Gly:MePhe:BODIPYFL-4-AMF:Ile:Ile:Pro:Ile:Gly (SEQ ID NO: 15) | 49.5 |
| L31intact ribosome | | 2 | MePhe:Ile:Ile:Gly:MePhe:BODIPYFL-4-AMF:Ile:Ile:Pro:Ile:Gly (SEQ ID NO: 15) | 12.8 |
| | | 4 | MePhe:Ile:Ile:Gly:MePhe:BODIPYFL-4-AMF:Ile:Ile:Pro:Ile:Gly (SEQ ID NO: 15) | 50.5 |
| | | 6 | MePhe:Ile:Ile:Gly:MePhe:BODIPYFL-4-AMF:Ile:Ile:Pro:Ile:Gly (SEQ ID NO: 15) | 58.9 |
| | | 8 | MePhe:Ile:Ile:Gly:MePhe:BODIPYFL-4-AMF:Ile:Ile:Pro:Ile:Gly (SEQ ID NO: 15) | 51.4 |

TABLE 3-3

| Ribosome | mRNA sequence | Mg concentration | Translation product | Translation amount (nM) |
|---|---|---|---|---|
| L31short ribosome | mR-2 | 2 | Acbz-MeCys (StBu):T:MePhe:Ile:Ile:Gly:MePhe:BODIPYFL-4-AMF:Ile:Ile:Pro:Ile:Gly (SEQ ID NO: 16) | 30.7 |
| | | 4 | Acbz-MeCys (StBu):T:MePhe:Ile:Ile:Gly:MePhe:BODIPYFL-4-AMF:Ile:Ile:Pro:Ile:Gly (SEQ ID NO: 16) | 42.7 |
| | | 6 | Acbz-MeCys (StBu):T:MePhe:Ile:Ile:Gly:MePhe:BODIPYFL-4-AMF:Ile:Ile:Pro:Ile:Gly (SEQ ID NO: 16) | 30.8 |
| | | 8 | Acbz-MeCys (StBu):T:MePhe:Ile:Ile:Gly:MePhe:BODIPYFL-4-AMF:Ile:Ile:Pro:Ile:Gly (SEQ ID NO: 16) | 19.9 |
| L31intact ribosome | | 2 | Acbz-MeCys (StBu):T:MePhe:Ile:Ile:Gly:MePhe:BODIPYFL-4-AMF:Ile:Ile:Pro:Ile:Gly (SEQ ID NO: 16) | 24.5 |
| | | 4 | Acbz-MeCys (StBu):T:MePhe:Ile:Ile:Gly:MePhe:BODIPYFL-4-AMF:Ile:Ile:Pro:Ile:Gly (SEQ ID NO: 16) | 20.5 |
| | | 6 | Acbz-MeCys (StBu):T:MePhe:Ile:Ile:Gly:MePhe:BODIPYFL-4-AMF:Ile:Ile:Pro:Ile:Gly (SEQ ID NO: 16) | 13.2 |
| | | 8 | Acbz-MeCys (StBu):T:MePhe:Ile:Ile:Gly:MePhe:BODIPYFL-4-AMF:Ile:Ile:Pro:Ile:Gly (SEQ ID NO: 16) | 4.7 |

TABLE 3-4

| Ribosome | mRNA sequence | Mg concentration | Translation product | Translation amount (nM) |
|---|---|---|---|---|
| L31short ribosome | mR-2 | 2 | MePhe:Ile:Ile:Gly:MePhe:BODIPYFL-4-AMF:Ile:Ile:Pro:Ile:Gly (SEQ ID NO: 15) | 3.5 |
| | | 4 | MePhe:Ile:Ile:Gly:MePhe:BODIPYFL-4-AMF:Ile:Ile:Pro:Ile:Gly (SEQ ID NO: 15) | 15.8 |
| | | 6 | MePhe:Ile:Ile:Gly:MePhe:BODIPYFL-4-AMF:Ile:Ile:Pro:Ile:Gly (SEQ ID NO: 15) | 28.3 |
| | | 8 | MePhe:Ile:Ile:Gly:MePhe:BODIPYFL-4-AMF:Ile:Ile:Pro:Ile:Gly (SEQ ID NO: 15) | 32.4 |
| L31intact ribosome | | 2 | MePhe:Ile:Ile:Gly:MePhe:BODIPYFL-4-AMF:Ile:Ile:Pro:Ile:Gly (SEQ ID NO: 15) | 25.0 |
| | | 4 | MePhe:Ile:Ile:Gly:MePhe:BODIPYFL-4-AMF:Ile:Ile:Pro:Ile:Gly (SEQ ID NO: 15) | 37.3 |
| | | 6 | MePhe:Ile:Ile:Gly:MePhe:BODIPYFL-4-AMF:Ile:Ile:Pro:Ile:Gly (SEQ ID NO: 15) | 49.1 |
| | | 8 | MePhe:Ile:Ile:Gly:MePhe:BODIPYFL-4-AMF:Ile:Ile:Pro:Ile:Gly (SEQ ID NO: 15) | 48.8 |

Overview of Experiment 2

In Example 2, wild-type *E. coli* derived from the W3110 strain was used, and ribosomes were prepared using disruption buffers prepared at three $Mg^{2+}$ concentrations—10 mM, 5 mM, and 0 mM. Ribosomes prepared by their respective preparation methods are called the WT-10MG ribosome, the WT-5MG ribosome, and the WT-0MG ribosome. In Example 3, the percentage of the L31 protein degraded during purification was determined by MALDI-MS for each of the ribosomes. The results showed that the lower $Mg^{2+}$ concentration in the disruption solution was, the more L31 was degraded.

Using these ribosomes, translation experiments were performed using the mR-2 sequence, as in Experiment 1.

The results revealed that when using the WT-0MG ribosome having the most degraded L31, the amount of the target molecule was the largest.

Translation Condition

The translation system used was the PURE system, a reconstituted cell-free protein synthesis system derived from prokaryotes. Specifically, a translation solution contained the following: 1 mM GTP, 1 mM ATP, 20 mM creatine phosphate, 50 mM HEPES-KOH pH 7.6, 100 mM potassium acetate, 4 mM magnesium acetate, 2 mM spermidine, 1 mM dithiothreitol, 1.0 mg/mL *E. coli* MRE600 (RNase negative)-derived tRNA (Roche) (some tRNAs had been removed by the method of the non-patent literature (Yokogawa T, Kitamura Y, Nakamura D, Ohno S, Nishikawa K. 2010. Nucleic acids research 38:e89)), 3 μM in vitro transcribed *E. coli* tRNA Ala1B, 0.26 μM EF-G, 4 μg/mL creatine kinase, 3 μg/mL myokinase, 2 units/mL inorganic pyrophosphatase, 1.1 μg/mL nucleoside diphosphate kinase, 2.7 μM IF1, 0.4 μM IF2, 1.5 μM IF3, 40 μM EF-Tu, 35 μM EF-Ts, 1 μM EF-P-Lys, 0.4 units/μL RNasin Ribonuclease inhibitor (Promega, N2111), 0.5 μM Penicillin G Amidase (PGA), 2.7 μM AlaRS, 1 μM GlyRS, 0.4 μM IleRS, 0.5 μM mutant PheRS (WO 2016/148044), 0.16 μM ProRS, 0.09 μM ThrRS, 1 μM mutant ValRS (WO 2016/148044), 1 μM mutant SerRS (WO 2016/148044), 250 μM Gly, 250 μM Lys, 100 μM Ile, 250 μM Pro, 250 μM Thr, 5 mM N-methylalanine, 5 mM N-methylphenylalanine, 5 mM N-methylserine, and 5 mM N-methylvaline. Initiator aminoacyl-tRNA (Compound AAtR-3) was added at 25 μM, and each of the aminoacyl-tRNAs including Compounds AAtR-1 and AAtR-2 was added at 10 μM to the translation reaction mixture. The mixture contained 185 μM aminoacyl-tRNAs not used for translation. Translation was performed by adding the WT-0MG ribosome, the WT-5MG ribosome, or the WT-10MG ribosome at 1.2 μM, and leaving the mixture to stand at 37° C. for one hour. Thereafter, the mixture was heated at 95° C. for three min and then left to stand until it reached at room temperature. Peptidyl-tRNA hydrolase (Pth) was added at 8.58 μM and the mixture was left to stand at 37° C. for one hour.

Overview of the Analysis

A solution that contained a peptide translation product comprising unnatural amino acids was diluted ten-fold and analyzed using an LC-FLR-MS instrument. For the analytical data, the retention time of the translated peptide of interest was determined from the MS data, and the amount of translated peptide was evaluated by quantifying the fluorescence peak of the corresponding retention time. For the quantitative evaluation, a calibration curve was prepared using the LCT12 synthesized in Example 6 as a standard, and the content was calculated by relative quantitation. LC-MS was performed under the following analysis conditions. Analysis conditions

TABLE 4

| | |
|---|---|
| Instrument | Aquity UPLC-FLR-Xevo G2-XS Tof |
| Column | waters BEHC18 (2.1 × 50 mm, ϕ1.7 μm) |
| Mobile phase | A = 0.1% FA with H2O<br>B = 0.1% FA with CH3CN |
| Gradient (% B) | 0-0.2 min = 10%<br>0.2-3.6 min = 98%<br>3.6-4.0 min = 10% |
| Flow rate (mL/min) | 0.5 |
| Column temperature | 40 |
| Fluorescence measurement wavelength (Ex/Em) | 491 nm/515 nm |
| Ms mode | ESI− |

Results

The ribosomes in descending order of the amount of the target molecule translated were the WT-0MG ribosome, the WT-5MG ribosome, and the WT-10MG ribosome.

Furthermore, the ribosomes in ascending order of the percentage of iRT peptide to the target molecule were the WT-0MG ribosome, the WT-5MG ribosome, and the WT-10MG ribosome.

The results from Experiment 1 and Example 3 showed that under conditions of low $Mg^{2+}$ concentration in the disruption solution, the percentage of ribosomes in which L31 was degraded increased, and the amount of translation in the iSup method can be increased.

TABLE 5

| Ribosome | mRNA sequence | Mg concentration | Translation product | Translation amount (nM) |
|---|---|---|---|---|
| WT-0MG ribosome | mR-2 | 4 | Acbz-MeCys (StBu):T:MePhe:Ile:Ile:Gly:MePhe:BODIPYFL-4-AMF:Ile:Ile:Pro:Ile:Gly (SEQ ID NO: 16) | 27.9 |
| WT-5MG ribosome | | | Acbz-MeCys (StBu):T:MePhe:Ile:Ile:Gly:MePhe:BODIPYFL-4-AMF:Ile:Ile:Pro:Ile:Gly (SEQ ID NO: 16) | 25.2 |
| WT-10MG ribosome | | | Acbz-MeCys (StBu):T:MePhe:Ile:Ile:Gly:MePhe:BODIPYFL-4-AMF:Ile:Ile:Pro:Ile:Gly (SEQ ID NO: 16) | 18.2 |
| WT-0MG ribosome | | | MePhe:Ile:Ile:Gly:MePhe:BODIPYFL-4-AMF:Ile:Ile:Pro:Ile:Gly (SEQ ID NO: 15) | 23.2 |
| WT-5MG ribosome | | | MePhe:Ile:Ile:Gly:MePhe:BODIPYFL-4-AMF:Ile:Ile:Pro:Ile:Gly (SEQ ID NO: 15) | 28.7 |
| WT-10MG ribosome | | | MePhe:Ile:Ile:Gly:MePhe:BODIPYFL-4-AMF:Ile:Ile:Pro:Ile:Gly (SEQ ID NO: 15) | 34.7 |

Example 8. Panning Using the L31Short Ribosome

Synthesis of Acylated tRNAs

Acylated tRNAs used for panning were prepared by the methods described in the patent literature (WO 2013/100132). Fifteen amino acids including Pic(2), MeAla(3-pyr), Ser(Ph-2-Cl), and MeGly described in the patent literature (WO 2018/225864) were used to prepare a mixture of Elongator aminoacyl-tRNAs. The final concentrations of each of the acylated tRNAs in the translation solution were from 10 μM to 20 μM. Operations following phenol extraction were performed on Pnaz-protected pCpA amino acids without subjecting them to deprotection. The initiator aminoacyl-tRNA was the same compound as Compound AAtR-3 of Example 5, and it was used by addition to the translation solution at a final concentration of 25 μM.

Randomized Double-Stranded DNA Library Encoding a Peptide Compound Library

A DNA library was constructed by the method described in the patent literature (WO 2013/100132). DNAs in which 24 triplets, including TTT, TTG, CTT, ATT, ATG, GTT, CCG, ACT, GCT, CAT, CAG, AAC, GAA, TGG, CGG, AGT, AGG, and GGT, randomly and repeatedly appear 8 or 9 times were prepared.

Preparation of Biotinylated Target Proteins

Glutathione S-transferase (GST) was used as the target protein for panning. GST expressed in *E. coli* was prepared and used. Biotinylation was performed according to Non-patent Literatures BMC biotechnology, 2008, 8, 41 and Protein Science, 1990; 108(4): 673-6.

Translation Solution Used for Panning

The translation solution contained the following substances: 1 mM GTP, 1 mM ATP, 20 mM creatine phosphate, 50 mM HEPES-KOH pH 7.6, 100 mM potassium acetate, 6 mM magnesium acetate, 2 mM spermidine, 1 mM dithiothreitol, 1 mg/mL *E. coli* MRE600 (RNase negative)-derived tRNA (Roche) (some of the tRNAs have been removed by the method of the non-patent literature (Yokogawa T, Kitamura Y, Nakamura D, Ohno S, Nishikawa K. 2010. Nucleic acids research 38:e89)), 4 μg/mL creatine kinase, 3 μg/mL myokinase, 2 units/mL inorganic pyrophosphatase, 1.1 μg/mL nucleoside diphosphate kinase, 0.26 μM EF-G, 2.7 μM IF1, 0.4 μM IF2, 1.5 μM IF3, 40 μM EF-Tu, 49 μM EF-Ts, 1 μM EF-P-Lys, 1.2 μM ribosome (L31short or L31intact), 2.73 μM AlaRS, 1 μM GlyRS, 0.4 μM IleRS, 0.5 μM mutant PheRS (WO 2016/148044), 0.16 μM ProRS, 1 μM mutant SerRS (WO 2016/148044), 0.09 μM ThrRS, 1 μM mutant ValRS (WO 2016/148044), 0.11 μM LysRS, 3 μM in vitro transcribed *E. coli* tRNA Ala1B, 250 μM glycine, 100 μM isoleucine, 250 μM proline, 250 μM threonine, 250 μM lysine, 5 mM N-methylvaline, 5 mM N-methylserine, 5 mM N-methylalanine, 5 mM N-methylphenylalanine, mixture of Elongator aminoacyl-tRNAs, 25 μM Initiator aminoacyl-tRNA, and 10 μM Penicillin G Amidase (PGA).

Panning

The above-mentioned double-stranded DNA library and the translation solution containing L31short or the translation solution containing L31intact were used to perform panning according to the patent literature (WO 2013/100132). A TEV protease recognition sequence was inserted between GST and biotin, and elution was performed with TEV protease. After the peptide library was allowed to interact with the biotinylated protein, it was recovered using streptavidin-immobilized magnetic beads, and then washed, and subsequently a solution for TEV elution (50 mM Tris-HCl pH 8.0, 0.5 mM EDTA, 1 mM DTT, 0.1 U/μL AcTEV protease (Thermo Fisher Scientific, Product No. 12575015)) was added to the beads to allow reaction. After the reaction, the supernatant was collected and PCR was performed.

Analysis of the Enriched Sequence

The extracted sequences were as follows: appearance frequency upon at least one or more rounds of panning was Rank A: 0.5% or more; Rank B: 0.05% or more; or Rank C: number of reads by NGS is 50 or more, and appearance frequency increased by ten-fold or more when panning was performed by dividing pool of the latest round and adding a target, as compared to when the panning was performed without target addition. As a result, when a translation system using the L31short ribosome was used, 33 sequences were Rank A, 253 sequences were Rank B, and 396 sequences were Rank C. On the other hand, when a translation system using the L31intact ribosome was used, 32 sequences were Rank A, 175 sequences were Rank B, and 247 sequences were Rank C. When panning was performed using the L31short ribosome, more sequences could be enriched than when panning was performed using the L31intact ribosome.

Example 9. Translation Experiment Using the L31 Mutant Ribosome

Overview of Example 9

As described later in Example 14, eight L31 mutant strains each having different lengths of L31 were constructed. As described in Example 15, ribosomes were prepared from these strains, as well as the L31short strain, the L31intact strain, and the W3110 strain. Translation properties of ribosomes respectively comprising the L31 mutant were investigated by performing ribosomal syntheses of peptides using the eleven obtained ribosomes.

Specifically, the following three peptides having different amino acids corresponding to the second letter were ribosomally synthesized using the eleven ribosomes R1 to R11 shown in Table 6. Herein, amino acid sequences may be represented by separating the amino acids with a colon as follows.

AcbzMeCStBu:MeG:MeF:I:I:G:MeF:Bdp4AMF:I:I:P:I:G (SEQ ID NO: 29)

AcbzMeCStBu:MeStBuOH:MeF:I:I:G:MeF:Bdp4AMF:I:I:P:I:G (SEQ ID NO: 30)

AcbzMeCStBu:L:MeF:I:I:G:MeF:Bdp4AMF:I:I:P:I:G (SEQ ID NO: 31)

The template mRNA sequence mR-1 (SEQ ID NO: 10) was used with each of MeG-tRNAGlu(CUG), MeSer(tBuOH)-tRNAGlu(CUG), and Leu-tRNAGlu(CUG), which were the aminoacyl-tRNAs that processed the second letter. The aminoacyl-tRNAs prepared in Example 13 were used.

TABLE 6

| Ribosome abbreviation | Ribosome name |
|---|---|
| R1 | L31 (1-27) ribosome |
| R2 | L31 (1-32) ribosome |
| R3 | L31 (1-37) ribosome |
| R4 | L31 (1-42) ribosome |
| R5 | L31 (1-47) ribosome |
| R6 | L31 (1-52) ribosome |
| R7 | L31 (1-57) ribosome |
| R8 | L31 (1-67) ribosome |
| R9 | WT ribosome |
| R10 | L31intact ribosome |
| R11 | L31short ribosome |

The target molecules (TM) and by-products were quantified using LC-MS. The main by-products observed were the Initiation Read-through (iRT) peptides whose translation was initiated from the amino acid corresponding to the third letter from the initial amino acid. Herein, a peptide whose translation was started from the second letter from the initiation may be referred to as 1iRT, and a peptide whose translation was started from the third letter from the initiation may be referred to as 2iRT. Tables 7 to 9 show the TMs (SEQ ID NO: 29 to 31) and each of the corresponding 1iRTs and 2iRTs.

TABLE 7

| | Amino acid sequence | SEQ ID NO |
|---|---|---|
| TM | AcbzMeCStBu:MeG:MeF:I:I:G:MeF:Bdp4AMF:I:I:P:I:G | 29 |
| 1iRT | MeG:MeF:I:I:G:MeF:Bdp4AMF:I:I:P:I:G | 32 |
| 2iRT | MeF:I:I:G:MeF:Bdp4AMF:I:I:P:I:G | 35 |

TABLE 8

| | Amino acid sequence | SEQ ID NO |
|---|---|---|
| TM | AcbzMeCStBu:MeStBuOH:MeF:I:I:G:MeF:Bdp4AMF:I:I:P:I:G | 30 |
| 1iRT | MeStBuOH:MeF:I:I:G:MeF:Bdp4AMF:I:I:P:I:G | 33 |
| 2iRT | MeF:I:I:G:MeF:Bdp4AMF:I:I:P:I:G | 35 |

TABLE 9

| | Amino acid sequence | SEQ ID NO |
|---|---|---|
| TM | AcbzMeCStBu:L:MeF:I:I:G:MeF:Bdp4AMF:I:I:P:I:G | 31 |
| 1iRT | L:MeF:I:I:G:MeF:Bdp4AMF:I:I:P:I:G | 34 |
| 2iRT | MeF:I:I:G:MeF:Bdp4AMF:I:I:P:I:G | 35 |

Translation Conditions

Upon excluding in vitro transcribed *E. coli* tRNA Ala1B, Lys, and aminoacyl-tRNA from the translation solution composition of Experiment 1 in Example 7, the translation conditions of Experiment 1 in Example 7 were followed, except that 0.5 μM HisRS was added and the composition was 6.72 units/mL myokinase, 59 μM EF-Ts, 4 mM magnesium acetate, 20 μM initiator aminoacyl-tRNA (Compound AAtR-3), 10 μM each of the aminoacyl-tRNAs coding for the second letter, 1.2 μM each of the ribosomes, and 1 μM mRNA.

Overview of the Analysis

The analysis was performed according to the method of Experiment 2 of Example 7, except that quantitative evaluation was performed upon preparing the calibration curve using the LCT67 synthesized in Example 11 as a standard.

Results

As shown in Table 10, all three sequences showed translation properties that the amount of translated TM was high and the percentage of Initiation Read-through (iRT) peptide was low in translation using the ribosomes R1 to R7 and R11. Ribosomes comprising the L31 mutants with 62 or fewer amino acid residues from the N-terminus were shown to have properties of high translational activity and a low percentage of Initiation Read-through (iRT) peptides. The iRT percentage was calculated by the following equation.

iRT percentage=(total iRT concentration [nM]/(total iRT concentration [nM]+TM concentration [nM])×100 (Equation 1)

TABLE 10

| No. | Ribosome abbreviation | Amino acid representing second letter | TM concentration [nM] | 1iRT concentration [nM] | 2iRT concentration [nM] | Total iRT concentration [nM] | iRT percentage |
|---|---|---|---|---|---|---|---|
| 1 | R1 | MeG | 88 | 0 | 71 | 71 | 45% |
| 2 | R2 | MeG | 83 | 0 | 83 | 83 | 50% |
| 3 | R3 | MeG | 89 | 0 | 67 | 67 | 43% |
| 4 | R4 | MeG | 97 | 0 | 72 | 72 | 42% |
| 5 | R5 | MeG | 86 | 0 | 78 | 78 | 48% |
| 6 | R6 | MeG | 95 | 0 | 73 | 73 | 44% |
| 7 | R7 | MeG | 97 | 0 | 60 | 60 | 39% |
| 8 | R8 | MeG | 49 | 0 | 115 | 115 | 70% |
| 9 | R9 | MeG | 37 | 0 | 137 | 137 | 79% |
| 10 | R10 | MeG | 35 | 0 | 151 | 151 | 81% |
| 11 | R11 | MeG | 80 | 0 | 73 | 73 | 48% |
| 12 | R1 | MeStBuOH | 108 | 0 | 83 | 83 | 44% |
| 13 | R2 | MeStBuOH | 111 | 0 | 100 | 100 | 47% |
| 14 | R3 | MeStBuOH | 119 | 0 | 96 | 96 | 45% |
| 15 | R4 | MeStBuOH | 116 | 0 | 101 | 101 | 46% |
| 16 | R5 | MeStBuOH | 119 | 0 | 102 | 102 | 46% |
| 17 | R6 | MeStBuOH | 109 | 0 | 101 | 101 | 48% |
| 18 | R7 | MeStBuOH | 121 | 0 | 103 | 103 | 46% |
| 19 | R8 | MeStBuOH | 58 | 0 | 117 | 117 | 67% |
| 20 | R9 | MeStBuOH | 51 | 0 | 141 | 141 | 74% |
| 21 | R10 | MeStBuOH | 43 | 0 | 134 | 134 | 76% |
| 22 | R11 | MeStBuOH | 86 | 0 | 88 | 88 | 51% |
| 23 | R1 | L | 117 | 0 | 15 | 15 | 11% |
| 24 | R2 | L | 107 | 0 | 19 | 19 | 15% |
| 25 | R3 | L | 124 | 0 | 19 | 19 | 14% |
| 26 | R4 | L | 119 | 0 | 24 | 24 | 17% |
| 27 | R5 | L | 113 | 0 | 22 | 22 | 16% |
| 28 | R6 | L | 120 | 0 | 19 | 19 | 14% |
| 29 | R7 | L | 110 | 0 | 21 | 21 | 16% |
| 30 | R8 | L | 66 | 0 | 39 | 39 | 37% |
| 31 | R9 | L | 65 | 0 | 37 | 37 | 36% |
| 32 | R10 | L | 59 | 0 | 46 | 46 | 44% |
| 33 | R11 | L | 95 | 0 | 15 | 15 | 14% |

Example 10. Effects of the L31Short Ribosome on Ribosomal Synthesis of Various Peptides

Experiment 1. AcbzdMeCStBu was Placed as the Initial Amino Acid, and Various Amino Acids were Placed as the Second Letter

Overview of Experiment 1

Using the L31short ribosome and the L31intact ribosome purified in Example 2, six peptides having different amino acids representing the second letter were ribosomally synthesized to confirm that advantageous translation properties of the L31short ribosome were shown in ribosomal synthesis of a number of peptides.

Specifically, six peptides with different amino acids representing the second letter (X) of the following amino acid sequence (SEQ ID NO: 36) were ribosomally synthesized. Here, X was Nle, S3F5MePyr, SPh2Cl, I, T, or L.

AcbzdMeCStBu:X:MeF:I:I:G:MeF:Bdp4AMF:I:I:P:I:G (SEQ ID NO: 36)

The template mRNA sequence mR-1 (SEQ ID NO: 10) was used with each of Nle-tRNAGlu(CUG), S3F5MePyr-tRNAGlu(CUG), SPh2Cl-tRNAGlu(CUG), Ile-tRNAGlu (CUG), Thr-tRNAGlu(CUG), and Leu-tRNAGlu(CUG), which were the aminoacyl-tRNAs that processed the second letter. Aminoacyl-tRNAs prepared in Example 13 were used.

The target molecules (TM) and by-products were quantified using LC-MS. The main by-products observed were 1iRT and 2iRT. The iRT percentage was calculated by the following equation.

iRT percentage=(total iRT concentration [nM]/(total iRT concentration [nM]+TM concentration [nM])×100 (Equation 1)

Translation Conditions

Upon excluding HisRS from the translation conditions of Example 9, the translation conditions of Example 9 were followed except that the composition was 8 mM magnesium acetate, 3 μg/mL myokinase, 49 μM EF-Ts, and 20 μM initiator aminoacyl-tRNA (Acbz-D-MeCys(StBu)-tRNAfMetCAU) (Patent Literature WO 2017150732).

Overview of the Analysis

The analysis was performed according to the method of Example 9.

Results

As shown in Table 11, the amount of translated TM in four out of the six sequences was increased by 2.8 times to 3.9 times when the L31short ribosome was used, as compared to when the L31intact ribosome was used, and in all of the six sequences, the percentage of iRT decreased when the L31short ribosome was used, as compared to when the L31intact ribosome was used.

TABLE 11

| Serial number | Ribosome | Amino acid representing second letter | TM concentration [nM] | 1iRT concentration [nM] | 2iRT concentration [nM] | Total iRT concentration [nM] | iRT percentage |
|---|---|---|---|---|---|---|---|
| 1 | L31short | Nle | 106 | 19 | 65 | 84 | 44% |
| 2 | ribosome | S3F5MePyr | 112 | 74 | 45 | 119 | 52% |
| 3 | | SPh2Cl | 26 | 44 | 14 | 58 | 69% |
| 4 | | I | 86 | 23 | 96 | 119 | 58% |
| 5 | | T | 15 | 44 | 111 | 155 | 91% |
| 6 | | L | 118 | 33 | 88 | 121 | 51% |
| 7 | L31intact | Nle | 27 | 26 | 56 | 82 | 75% |
| 8 | ribosome | S3F5MePyr | 40 | 144 | 60 | 204 | 84% |
| 9 | | SPh2Cl | 39 | 130 | 39 | 169 | 81% |
| 10 | | I | 28 | 13 | 189 | 202 | 88% |
| 11 | | T | 16 | 66 | 171 | 237 | 94% |
| 12 | | L | 37 | 67 | 115 | 182 | 83% |

Experiment 2. AcbzMeCStBu was Placed as the Initial Amino Acid, and Various Amino Acids were Placed as the Second Letter

Overview of Experiment 2

Using the L31short ribosome and the L31intact ribosome purified in Example 2, twelve peptides having different amino acids representing the second letter were ribosomally synthesized to confirm that advantageous translation properties of the L31short ribosome were shown in ribosomal synthesis of a number of peptides.

Specifically, twelve peptides with different amino acids representing the second letter (X) of the following amino acid sequence (SEQ ID NO: 37) were ribosomally synthesized. Here, X was Nle, MeG, MeF, S3F5MePyr, MeHph, MeA3Pyr, SPh2Cl, G, I, T, MeStBuOH, or L.

AcbzMeCStBu:X:MeF:I:I:G:MeF:Bdp4AMF:I:I:P:I:G (SEQ ID NO: 37)

Except that MeG-tRNAGlu(CUG), MePhe-tRNAGlu (CUG), MeHph-tRNAGlu(CUG), MeA3Pyr-tRNAGlu (CUG), Gly-tRNAGlu(CUG), or MeSer(tBuOH)-tRNAGlu (CUG) was additionally used as the aminoacyl-tRNAs that processed the second letter, the experiment was performed by a method following that of Experiment 1 of Example 10. The main by-products observed were 1iRT and 2iRT.

Translation Conditions

The translation conditions of Experiment 1 in Example 10 were followed, except that 4 mM magnesium acetate and 20 μM initiator aminoacyl-tRNA (Compound AAtR-3) were used.

Overview of the Analysis

The analysis was performed according to the method of Example 9.

Results

As shown in Table 12, the amount of translated TM in eleven out of the twelve sequences was increased by 1.6 times to 3.7 times when the L31short ribosome was used, as compared to when the L31intact ribosome was used, and in all of the twelve sequences, the percentage of iRT decreased when the L31short ribosome was used, as compared to when the L31intact ribosome was used.

TABLE 12

| Serial number | Ribosome | Amino acid representing second letter | TM concentration [nM] | 1iRT concentration [nM] | 2iRT concentration [nM] | Total iRT concentration [nM] | iRT percentage |
|---|---|---|---|---|---|---|---|
| 1 | L31short | Nle | 155 | 0 | 22 | 22 | 12% |
| 2 | ribosome | MeG | 94 | 0 | 54 | 54 | 36% |
| 3 | | MeF | 257 | 0 | 23 | 23 | 8% |
| 4 | | S3F5MePyr | 174 | 0 | 14 | 14 | 7% |
| 5 | | MeHph | 151 | 0 | 29 | 29 | 16% |
| 6 | | MeA3Pyr | 153 | 0 | 31 | 31 | 17% |
| 7 | | SPh2Cl | 195 | 13 | 11 | 24 | 11% |
| 8 | | G | 111 | 0 | 22 | 22 | 17% |
| 9 | | I | 166 | 0 | 23 | 23 | 12% |
| 10 | | T | 112 | 0 | 30 | 30 | 21% |
| 11 | | MeStBuOH | 25 | 0 | 12 | 12 | 32% |
| 12 | | L | 46 | 0 | 12 | 12 | 21% |
| 13 | L31intact | Nle | 76 | 0 | 82 | 82 | 52% |
| 14 | ribosome | MeG | 38 | 0 | 131 | 131 | 78% |
| 15 | | MeF | 69 | 0 | 58 | 58 | 46% |
| 16 | | S3F5MePyr | 77 | 52 | 66 | 118 | 61% |
| 17 | | MeHph | 93 | 0 | 89 | 89 | 49% |
| 18 | | MeA3Pyr | 75 | 0 | 113 | 113 | 60% |
| 19 | | SPh2Cl | 85 | 48 | 42 | 90 | 51% |
| 20 | | G | 41 | 0 | 105 | 105 | 72% |
| 21 | | I | 77 | 0 | 71 | 71 | 48% |

TABLE 12-continued

| Serial number | Ribosome | Amino acid representing second letter | TM concentration [nM] | 1iRT concentration [nM] | 2iRT concentration [nM] | Total iRT concentration [nM] | iRT percentage |
|---|---|---|---|---|---|---|---|
| 22 | | T | 57 | 0 | 85 | 85 | 60% |
| 23 | | MeStBuOH | 16 | 0 | 67 | 67 | 81% |
| 24 | | L | 50 | 18 | 72 | 90 | 64% |

Experiment 3. AcbzCStBu was Placed as the Initial Amino Acid, and Various Amino Acids were Placed as the Second Letter

Overview of Experiment 3

Using the L31short ribosome and the L31intact ribosome purified in Example 2, twelve peptides having different amino acids representing the second letter were ribosomally synthesized to confirm that advantageous translation properties of the L31short ribosome were shown in ribosomal synthesis of a number of peptides.

Specifically, twelve peptides with different amino acids representing the second letter (X) of the following amino acid sequence (SEQ ID NO: 38) were ribosomally synthesized. Here, X was Nle, MeG, MeF, S3F5MePyr, MeHph, MeA3Pyr, SPh2Cl, G, I, T, MeStBuOH, or L. The experiment was performed by a method following that of Experiment 2 of Example 10.

AcbzCStBu:X:MeF:I:I:G:MeF:Bdp4AMF:I:I:P:I:G (SEQ ID NO: 38)

The target molecules (TM) and by-products were quantified using LC-MS. The main by-products observed were 1iRT and 2iRT.

Translation Conditions

The translation conditions of Example 9 were followed, except that 0.23 μM EF-G, 5.92 units/mL myokinase 2, 1.0 μg/mL nucleoside diphosphate kinase, 2.4 μM IF1, 1.3 μM IF3, 35 μM EF-Tu, 52 μM EF-Ts, and 20 μM initiator aminoacyl-tRNA Acbz-Cys(StBu)-tRNAfMetCAU (WO 2017/150732) were used.

Overview of the Analysis

The analysis was performed according to the method of Example 9.

Results

As shown in Table 13, the amount of translated TM in all of the twelve sequences was increased by 1.7 times to 3.8 times when the L31short ribosome was used, as compared to when the L31intact ribosome was used, and in all of the twelve sequences, the percentage of iRT decreased when the L31short ribosome was used, as compared to when the L31intact ribosome was used.

TABLE 13

| Serial number | Ribosome | Amino acid representing second letter | TM concentration [nM] | 1iRT concentration [nM] | 2iRT concentration [nM] | Total iRT concentration [nM] | iRT percentage |
|---|---|---|---|---|---|---|---|
| 1 | L31short | Nle | 26 | 0 | 28 | 28 | 52% |
| 2 | ribosome | MeG | 14 | 0 | 43 | 43 | 76% |
| 3 | | MeF | 52 | 0 | 15 | 15 | 22% |
| 4 | | S3F5MePvr | 33 | 0 | 15 | 15 | 31% |
| 5 | | MeHph | 39 | 0 | 14 | 14 | 27% |
| 6 | | MeA3Pyr | 39 | 0 | 27 | 27 | 41% |
| 7 | | SPh2Cl | 32 | 0 | 8 | 8 | 19% |
| 8 | | G | 22 | 0 | 22 | 22 | 50% |
| 9 | | I | 44 | 0 | 8 | 8 | 16% |
| 10 | | T | 27 | 0 | 22 | 22 | 45% |
| 11 | | MeStBuOH | 29 | 0 | 16 | 16 | 35% |
| 12 | | L | 28 | 0 | 8 | 8 | 21% |
| 13 | L31intact | Nle | 16 | 0 | 22 | 22 | 59% |
| 14 | ribosome | MeG | 6 | 0 | 42 | 42 | 88% |
| 15 | | MeF | 19 | 0 | 24 | 24 | 55% |
| 16 | | S3F5MePvr | 16 | 0 | 22 | 22 | 58% |
| 17 | | MeHph | 17 | 0 | 29 | 29 | 62% |
| 18 | | MeA3Pyr | 14 | 0 | 37 | 37 | 73% |
| 19 | | SPh2Cl | 14 | 0 | 11 | 11 | 44% |
| 20 | | G | 6 | 0 | 33 | 33 | 85% |
| 21 | | I | 19 | 0 | 24 | 24 | 56% |
| 22 | | T | 11 | 0 | 31 | 31 | 73% |
| 23 | | MeStBuOH | 11 | 0 | 23 | 23 | 68% |
| 24 | | L | 12 | 0 | 22 | 22 | 65% |

Experiment 4. fMet was Placed as the Initial Amino Acid, and Various Amino Acids were Placed as the Second Letter

Overview of Experiment 4

Using the L31 short ribosome and the L31intact ribosome purified in Example 2, 13 peptides having different amino acids representing the second letter were ribosomally synthesized to confirm that advantageous translation properties of the L31 short ribosome were shown in ribosomal synthesis of a number of peptides.

Specifically, 13 peptides with different amino acids representing the second letter (X) of the following amino acid sequence (SEQ ID NO: 39) were ribosomally synthesized. Here, X was Nle, MeG, MeF, S3F5MePyr, Pic(2), MeHph, MeA3Pyr, SPh2Cl, G, I, T, MeStBuOH, or L.

fMet:X:MeF:I:IG:MeF:Bdp4AMF:I:IP:I:G (SEQ ID NO: 39)

Except that Pic(2)-tRNAGlu(CUG) was additionally used as the aminoacyl-tRNA that processed the second letter, the experiment was performed by a method following that of Experiment 2 of Example 10. The target molecules (TM) and by-products were quantified using LC-MS. The main by-products observed were 1iRT and 2iRT.

Translation Conditions

The translation conditions of Experiment 2 in Example 10 were followed, except that the initiator aminoacyl-tRNA (Compound AAtR-3) was removed, and 0.03 μM MetRS, 0.6 μM methionyl tRNA formyl transferase, 0.25 mM methionine, and 0.1 mM folate were added.

Overview of the Analysis

The analysis was performed according to the method of Example 9.

Results

As shown in Table 14, the amount of translated TM in 12 out of the 13 sequences was increased by 1.2 times to 2 times when the L31short ribosome was used, as compared to when the L31intact ribosome was used, and in all of the 13 sequences, the percentage of iRT decreased when the L31short ribosome was used, as compared to when the L31intact ribosome was used.

TABLE 14

| Serial number | Ribosome | Amino acid representing second letter | TM concentration [nM] | 1iRT concentration [nM] | 2iRT concentration [nM] | Total iRT concentration [nM] | iRT percentage |
|---|---|---|---|---|---|---|---|
| 1 | L31short | Nle | 298 | 0 | 0 | 0 | 0% |
| 2 | ribosome | MeG | 153 | 0 | 0 | 0 | 0% |
| 3 | | MeF | 302 | 0 | 0 | 0 | 0% |
| 4 | | S3F5MePyr | 374 | 0 | 0 | 0 | 0% |
| 5 | | Pic2 | 115 | 0 | 0 | 0 | 0% |
| 6 | | MeHph | 260 | 0 | 0 | 0 | 0% |
| 7 | | MeA3Pyr | 318 | 0 | 0 | 0 | 0% |
| 8 | | SPh2Cl | 298 | 0 | 0 | 0 | 0% |
| 9 | | G | 265 | 0 | 0 | 0 | 0% |
| 10 | | I | 290 | 0 | 0 | 0 | 0% |
| 11 | | T | 287 | 0 | 0 | 0 | 0% |
| 12 | | MeStBuOH | 278 | 0 | 0 | 0 | 0% |
| 13 | | L | 243 | 0 | 0 | 0 | 0% |
| 14 | L31intact | Nle | 148 | 0 | 0 | 0 | 0% |
| 15 | ribosome | MeG | 96 | 0 | 61 | 61 | 39% |
| 16 | | MeF | 219 | 0 | 35 | 35 | 14% |
| 17 | | S3F5MePyr | 222 | 0 | 32 | 32 | 12% |
| 18 | | Pic2 | 115 | 0 | 91 | 91 | 44% |
| 19 | | MeHph | 216 | 0 | 49 | 49 | 19% |
| 20 | | MeA3Pyr | 274 | 0 | 51 | 51 | 16% |
| 21 | | SPh2Cl | 183 | 0 | 27 | 27 | 13% |
| 22 | | G | 155 | 0 | 43 | 43 | 22% |
| 23 | | I | 192 | 0 | 33 | 33 | 15% |
| 24 | | T | 189 | 0 | 31 | 31 | 14% |
| 25 | | MeStBuOH | 187 | 0 | 64 | 64 | 25% |
| 26 | | L | 194 | 0 | 26 | 26 | 12% |

Experiment 5. AcbzMeCStBu was Placed as the Initial Amino Acid, Thr was Placed as the Amino Acid Representing the Second Letter, and Various Amino Acids were Placed as the Third Letter

Overview of Experiment 5

Using the L31 short ribosome and the L31intact ribosome purified in Example 15, 14 peptides having different amino acids representing the third letter were ribosomally synthesized to confirm that advantageous translation properties of the L31short ribosome were shown in ribosomal synthesis of a number of peptides.

Specifically, 14 peptides with different amino acids representing the third letter (X) of the following amino acid sequence (SEQ ID NO: 40) were ribosomally synthesized. Here, X was Nle, MeF, S3F5MePyr, Pic(2), MeHph, MeA3Pyr, SPh2Cl, G, I, P, T, MeStBuOH, dA, or L.

AcbzMeCStBu:T:X:I:IG:MeF:Bdp4AMF:I:IP:I:G (SEQ ID NO: 40)

The template mRNA sequence mR-3 (SEQ ID NO: 28) was used with each of the aminoacyl-tRNAs, Nle-tRNAGlu (CUG), MePhe-tRNAGlu(CUG), S3F5MePyr-tRNAGlu (CUG), Pic(2)-tRNAGlu(CUG), MeHph-tRNAGlu(CUG), MeA3Pyr-tRNAGlu(CUG), SPh2Cl-tRNAGlu(CUG), Gly-tRNAGlu(CUG), Ile-tRNAGlu(CUG), Pro-tRNAGlu (CUG), Thr-tRNAGlu(CUG), MeSer(tBuOH)-tRNAGlu (CUG), D-Ala-tRNAGlu(CUG), and Leu-tRNAGlu(CUG), which processed the third letter. Aminoacyl-tRNAs prepared in Example 13 were used.

The target molecules (TM) and by-products were quantified using LC-MS. The main by-products observed were 1iRT and 2iRT.

Preparation of mRNA

The template mRNA, Sequence mR-3 (SEQ ID NO: 28), was prepared from the template DNA (SEQ ID NO: 27) by in vitro transcription reaction using the RiboMAX Large Scale RNA production System T7 (Promega, P1280) and purified with the RNeasy Mini kit (Qiagen).

Translation Conditions

The translation conditions of Example 9 were followed, except that 10 μM respective aminoacyl-tRNA coding for the third letter was added.

Overview of the Analysis

The analysis was performed according to the method of Example 9.

Results

As shown in Table 15, the amount of translated TM in all of the 14 sequences was increased by 1.1 times to 20.9 times when the L31short ribosome was used, as compared to when the L31intact ribosome was used, and in all of the 14 sequences, the percentage of iRT decreased when the L31short ribosome was used, as compared to when the L31intact ribosome was used. In the Table, "1iRT+2iRT concentration" represents the sum of the concentrations of 1iRT and 2iRT quantified from the sum of each peak when the peaks corresponding to 1iRT and 2iRT respectively could not be separated in the chromatogram.

TABLE 15

| Serial number | Ribosome | Amino acid representing third letter | TM concentration [nM] | 1iRT concentration [nM] | 2iRT concentration [nM] | 1iRT + 2iRT concentration [nM] | Total iRT concentration [nM] | iRT percentage |
|---|---|---|---|---|---|---|---|---|
| 1 | L31short | Nle | 83 | 24 | 0 | 0 | 24 | 23% |
| 2 | ribosome | MeF | 131 | 0 | 41 | 0 | 41 | 24% |
| 3 | | S3F5MePyr | 90 | 0 | 0 | 39 | 39 | 30% |
| 4 | | Pic2 | 104 | 0 | 40 | 0 | 40 | 28% |
| 5 | | MeHph | 108 | 0 | 50 | 0 | 50 | 32% |
| 6 | | MeA3Pyr | 78 | 0 | 52 | 0 | 52 | 40% |
| 7 | | SPh2Cl | 123 | 0 | 43 | 0 | 43 | 26% |
| 8 | | G | 96 | 0 | 0 | 27 | 27 | 22% |
| 9 | | I | 97 | 24 | 0 | 0 | 24 | 20% |
| 10 | | P | 123 | 25 | 0 | 0 | 25 | 17% |
| 11 | | T | 106 | 0 | 0 | 26 | 26 | 20% |
| 12 | | MeStBuOH | 32 | 0 | 46 | 0 | 46 | 59% |
| 13 | | dA | 136 | 0 | 37 | 0 | 37 | 22% |
| 14 | | L | 87 | 20 | 0 | 0 | 20 | 18% |
| 15 | L31intact | Nle | 59 | 67 | 0 | 0 | 67 | 53% |
| 16 | ribosome | MeF | 88 | 0 | 130 | 0 | 130 | 60% |
| 17 | | S3F5MePyr | 56 | 0 | 0 | 140 | 140 | 71% |
| 18 | | Pic2 | 69 | 0 | 0 | 96 | 96 | 58% |
| 19 | | MeHph | 76 | 0 | 101 | 0 | 101 | 57% |
| 20 | | MeA3Pyr | 53 | 0 | 76 | 0 | 76 | 59% |
| 21 | | SPh2Cl | 59 | 0 | 0 | 80 | 80 | 58% |
| 22 | | G | 58 | 0 | 0 | 90 | 90 | 61% |
| 23 | | I | 57 | 60 | 0 | 0 | 60 | 51% |
| 24 | | P | 66 | 92 | 0 | 0 | 92 | 58% |
| 25 | | T | 65 | 75 | 0 | 0 | 75 | 54% |
| 26 | | MeStBuOH | 29 | 0 | 73 | 0 | 73 | 72% |
| 27 | | dA | 43 | 0 | 41 | 0 | 41 | 48% |
| 28 | | L | 4 | 66 | 0 | 0 | 66 | 94% |

Experiment 6. fMet was Placed as the Initial Amino Acid, Thy was Placed as the Amino Acid Representing the Second Letter, and Various Amino Acids were Placed as the Third Letter

Overview of Experiment 6

Using the L31 short ribosome and the L31intact ribosome purified in Example 15, 15 peptides having different amino acids representing the third letter were ribosomally synthesized to confirm that advantageous translation properties of the L31short ribosome were shown in ribosomal synthesis of a number of peptides.

Specifically, 15 peptides with different amino acids representing the third letter (X) of the following amino acid sequence (SEQ ID NO: 41) were ribosomally synthesized. Here, X was Nle, MeG, MeF, S3F5MePyr, Pic(2), MeHph, MeA3Pyr, SPh2Cl, G, I, P, T, MeStBuOH, dA, or L.

```
(SEQ ID NO: 41)
fMet:T:X:I:I:G:MeF:Bdp4AMF:I:I:P:I:G
```

Except that MeG-tRNAGlu(CUG) was additionally used as the aminoacyl-tRNA that processed the third letter, the experiment was performed by a method following that of Experiment 5 of Example 10. The target molecules (TM) and by-products were quantified using LC-MS. The main by-products observed were 1iRT and 2iRT.

Translation Conditions

The conditions of Experiment 4 in Example 10 were followed, except that 6.72 units/mL myokinase, 59 μM EF-Ts, and 0.09 μM GlyRS were used.

Overview of the Analysis

The analysis was performed according to the method of Example 9.

Results

As shown in Table 16, the amount of translated TM in all of the 15 sequences was increased when the L31short ribosome was used, as compared to when the L31intact ribosome was used, and the amount of translated TM when L31intact was used was at the detection limit or below. In all of the 15 sequences, the percentage of iRT decreased when the L31short ribosome was used, as compared to when the L31intact ribosome was used. In the Table, "1iRT+2iRT concentration" represents the sum of the concentrations of 1iRT and 2iRT quantified from the sum of each peak when the peaks corresponding to 1iRT and 2iRT respectively could not be separated in the chromatogram.

TABLE 16

| Serial number | Ribosome | Amino acid representing third letter | TM concentration [nM] | 1iRT concentration [nM] | 2iRT concentration [nM] | Total iRT concentration [nM] | iRT percentage |
|---|---|---|---|---|---|---|---|
| 1 | L31short ribosome | Nle | 27 | 57 | 0 | 57 | 68% |
| 2 | | MeG | 42 | 0 | 89 | 89 | 68% |
| 3 | | MeF | 52 | 0 | 62 | 62 | 54% |
| 4 | | S3F5MePyr | 48 | 31 | 52 | 83 | 64% |
| 5 | | Pic2 | 50 | 32 | 54 | 86 | 63% |
| 6 | | MeHph | 41 | 0 | 67 | 67 | 62% |
| 7 | | MeA3Pyr | 50 | 0 | 52 | 52 | 51% |
| 8 | | SPh2Cl | 10 | 27 | 24 | 51 | 84% |
| 9 | | G | 43 | 29 | 52 | 82 | 66% |
| 10 | | I | 18 | 46 | 0 | 46 | 72% |
| 11 | | P | 47 | 73 | 0 | 73 | 61% |
| 12 | | T | 44 | 43 | 0 | 43 | 49% |
| 13 | | MeStBuOH | 29 | 0 | 85 | 85 | 74% |
| 14 | | dA | 36 | 0 | 73 | 73 | 67% |
| 15 | | L | 29 | 56 | 0 | 56 | 66% |
| 16 | L31intact ribosome | Nle | 0 | 34 | 0 | 34 | 100% |
| 17 | | MeG | 0 | 0 | 31 | 31 | 100% |
| 18 | | MeF | 0 | 21 | 39 | 59 | 100% |
| 19 | | S3F5MePyr | 0 | 29 | 35 | 65 | 100% |
| 20 | | Pic2 | 0 | 0 | 46 | 46 | 100% |
| 21 | | MeHph | 0 | 0 | 36 | 36 | 100% |
| 22 | | MeA3Pyr | 0 | 22 | 0 | 22 | 100% |
| 23 | | SPh2Cl | 0 | 32 | 41 | 73 | 100% |
| 24 | | G | 0 | 44 | 0 | 44 | 100% |
| 25 | | I | 0 | 58 | 0 | 58 | 100% |
| 26 | | P | 0 | 45 | 0 | 45 | 100% |
| 27 | | T | 0 | 0 | 65 | 65 | 100% |
| 28 | | MeStBuOH | 0 | 0 | 58 | 58 | 100% |
| 29 | | dA | 0 | 33 | 0 | 33 | 100% |
| 30 | | L | 0 | 38 | 20 | 58 | 100% |

Example 11. Synthesis of LCT-67

A peptide having BdpFL at its N-terminus (LCT-67), which was used as a standard in LC/MS, was synthesized by the following procedure.

Using 2-chlorotrityl resin (100 mg) loaded with Fmoc-Gly-OH, peptide elongation was performed on a peptide synthesizer using Fmoc-Gly-OH, Fmoc-Thr(THP)-OH synthesized by the method described in the patent literature (WO 2018225864) (aa01), Fmoc-Ile-OH, Fmoc-Leu-OH, Fmoc-Phe-OH, Fmoc-MePhe-OH, and Fmoc-Pro-OH as the Fmoc amino acids (amino acid abbreviations are described in the other portion in this specification). Peptide elongation was performed by following the peptide synthesis method by the Fmoc method (see for example, WO 2013100132). After the peptide elongation, the Fmoc group at the N-terminus was removed on the peptide synthesizer, and then the resin was washed with DCM.

TFE/DCM (1:1, v/v, 2 mL) was added to the resin, and this was shaken for one hour to cleave the peptide from the resin. After completion of the reaction, the solution in the tube was filtered through a synthesis column to remove the resin, and the resin was washed twice with TFE/DCM (1:1, v/v, 1 mL). All the extracted solutions were combined, DMF (2 mL) was added, and then this was concentrated under reduced pressure. The resulting residue was dissolved in NMP (1 mL), 4,4-difluoro-5,7-dimethyl-4-bora-3a,4a-diaza-s-indacene-3-propionic acid N-succinimidyl ester (5 mg, 0.013 mmol) was added thereto at room temperature, and this was stirred for 19 hours. The reaction solution was then subjected to reverse-phase silica gel column chromatography (0.1% FA MeCN/$H_2O$), and the fraction containing the intermediate was concentrated under reduced pressure. The resulting residue was dissolved in 5% TFA in DCM (2 mL), and this was stirred at room temperature for two hours. The reaction solution was concentrated under reduced pressure, and then the resulting residue was purified by reverse-phase silica gel column chromatography (0.1% FA MeCN/$H_2O$) to give the title compound (LCT-67) (13 mg). The amino acid sequence of LCT-67 is shown in SEQ ID NO: 223.

LCMS (ESI) m/z=1751.2 (M−H)−

Retention time: 0.97 min (analysis condition SQDFA05_02)

Example 12. Synthesis of pCpA Amino Acids

The following abbreviations were used in the present Examples: Gly or G (glycine), Ile or I (isoleucine), Leu or L (leucine), Phe or F (phenylalanine), Pro or P (proline), and Thr or T (threonine).

The LCMS analysis conditions are shown in Table 17 below.

TABLE 17

| Preparative condition | Instrument | Column (I.D. × length) (mm) | Mobile phase | Gradient (A/B) | Flow rate (mL/min) | Column temperature (° C.) | Wavelength |
|---|---|---|---|---|---|---|---|
| SQD FA05_01 | Acquity UPLC/SQD | Aldrich Ascentis Express C18 1.7 μm (2.1 × 50) | A) 0.1% FA, H2O B) 0.1% FA CH3CN | 95/5 => 0/100 (1.0 min) => 0/100 (0.4 min) | 1.0 | 35 | 210-400 nm PDA total |
| SQD FA05_02 | Acquity UPLC/SQD2 | Aldrich Ascentis Express C18 2.7 μm (2.1 × 50) | A) 0.1% FA, H2O B) 0.1% FA CH3CN | 95/5 => 0/100 (1.0 min) => 0/100 (0.4 min) | 0.9 | 35 | 210-400 nm PDA total |
| SMD method 1 | Shimadzu LCMS-2020 LC-20ADXR | kinetex 2.6u XB-C18 100A 2.6 μm (3.0 × 50) | A) 0.1% FA, H2O B) 0.1% FA CH3CN | 90/10 => 0/100 (1.2 min) => 0/100 (0.5 min) | 1.5 | 40 | 190-400 nm PDA total |
| SMD method 2 | Shimadzu LCMS-2020 LC-30AD | kinetex 2.6u XB-G18 100A 2.6 μm (2.1 × 50) | A) 0.05% TFA, H2O B) 0.05% TFA CH3CN | 95/5 => 0/100 (1.1 min) => 0/100 (0.5 min) | 1.0 | 40 | 190-400 nm PDA total |
| SMD method 3 | Shimadzu LCMS-2020 LC-20AD | Shim-Pack XR-ODS 2.2 μm (30 × 50) | A) 0.05% TFA, H2O B) 0.05% TFA CH3CN | 95/5 => 0/100 (1.1 min) => 0/100 (0.6 min) | 1.2 | 40 | 190-400 nm PDA total |
| SMD method 4 | Shimadzu LCMS-2020 LC-20ADXR | CORTECS C18 2.7 μm (2.1 × 50) | A) 0.1% FA, H2O B) 0.1% FA CH3CN | 90/10 => 0/100 (1.2 min) => 0/100 (0.5 min) | 1.0 | 40 | 190-400 nm PDA total |
| SMD method 5 | Shimadzu LCMS-2020 LC-30AD | Ascentis Express C18 2.7 μm (2.1 × 50) | A) 0.05% TFA, H2O B) 0.05% TFA CH3CN | 95/5 => 0/100 (1.1 min) => 0/100 (0.5 min) | 1.0 | 40 | 190-400 nm PDA total |
| SMD method 6 | Shimadzu LCMS-2020 LC-20AD | Shim-Pack XR-ODS 1.7 μm (2.1 × 50) | A) 0.1% FA, H2O B) 0.1% FA CH3CN | 90/10 => 0/100 (1.1 min) => 0/100 (0.6 min) | 1.2 | 40 | 190-400 nm PDA total |

Aminoacyl-pCpAs (ST04, ST08, ST11, ST14, ST17, ST20, ST23, ST28, ST31, ST32, ST33, and ST34) were synthesized according to the following scheme.

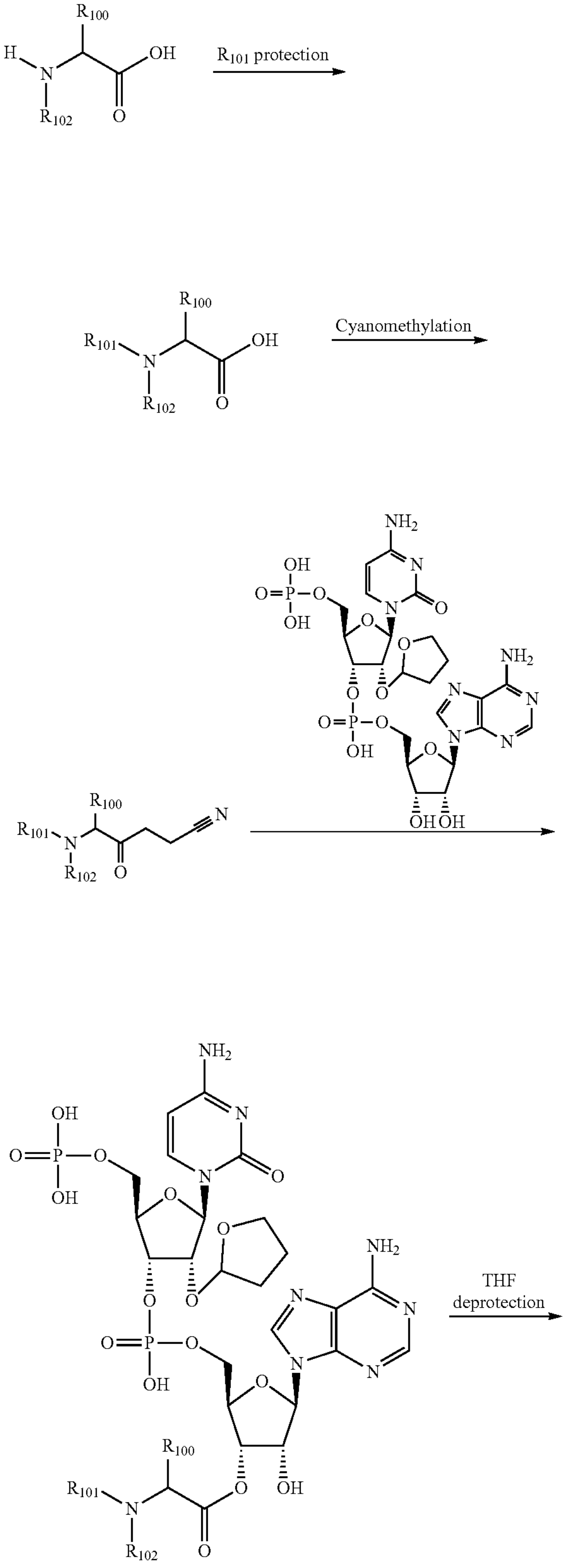

-continued

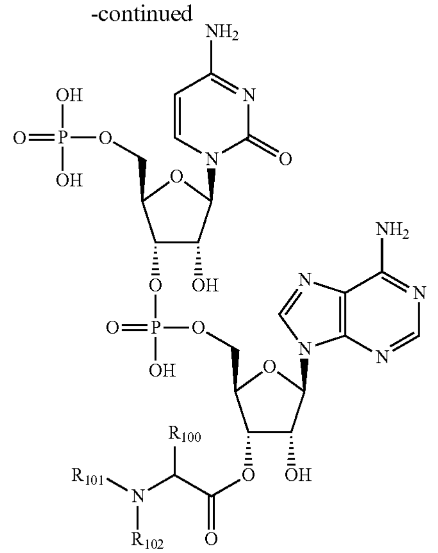

Synthesis of (2S)-2-aminohexanoic acid (Compound ST01, Nle-OH)

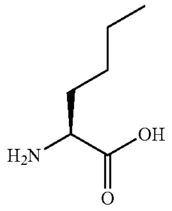

Under a nitrogen atmosphere, DCM (0.2 mL) and $H_2O$ (0.8 mL) were added at room temperature to (2S)-2-(9H-fluoren-9-ylmethoxycarbonylamino)hexanoic acid (35.3 mg, 0.10 mmol) synthesized by the method described in the patent literature (WO 2018225851 A1), 4-(3-phenylpropyl) piperidine (0.212 mL, 1.00 mmol) was then added at room temperature, and this mixture was stirred for 30 min. The reaction mixture was left to stand and then the aqueous layer was purified by reverse-phase silica gel column chromatography (0.1% aqueous formic acid solution/0.1% formic acid-acetonitrile solution) to give (2S)-2-aminohexanoic acid (Compound ST01, Nle-OH) (10 mg, 76%).

LCMS (ESI) m/z=130.0 (M−H)−

Retention time: 0.14 min (analysis condition SQDFA05_02)

Synthesis of (2S)-2-[[4-[[2-(4-fluorophenyl)acetyl] amino]phenyl]methoxycarbonylamino]hexanoic acid (Compound ST02, F-Pnaz-Nle-OH)

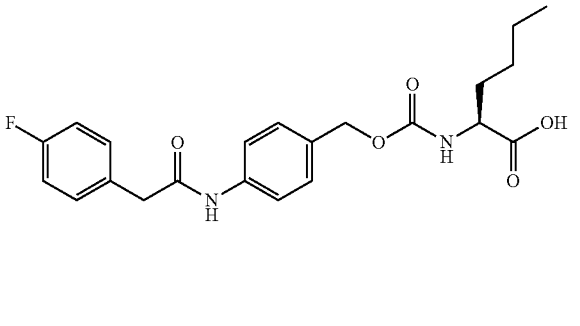 [SMILES: CCCC[C@H](NC(=O)OCc1ccc(NC(=O)Cc2ccc(F)cc2)cc1)C(=O)O]

Under a nitrogen atmosphere, DMSO (150 μL) and triethylamine (9.62 μL, 0.07 mmol) were added at room temperature to a mixture of (2S)-2-aminohexanoic acid (Compound ST01, Nle-OH) (3.94 mg, 0.03 mmol) and (4-nitrophenyl)-4-(2-(4-fluorophenyl)acetamide)benzyl carbonate (12.7 mg, 0.03 mmol) synthesized by the method described in the patent literature (WO 2018143145 A1). The reaction mixture was placed at room temperature and stirred for one hour, and then purified by reverse-phase silica gel column chromatography (0.1% aqueous formic acid solution/0.1% formic acid-acetonitrile solution) to give (2S)-2-[[4-[[2-(4-fluorophenyl)acetyl]amino]phenyl]methoxycarbonylamino]hexanoic acid (Compound ST02, F-Pnaz-Nle-OH) (9 mg, 72%).

LCMS (ESI) m/z=415.3 (M−H)−

Retention time: 0.74 min (analysis condition SQDFA05_02)

Synthesis of cyanomethyl (2S)-2-[[4-[[2-(4-fluorophenyl)acetyl]amino]phenyl]methoxycarbonylamino]hexanoate (Compound ST03, F-Pnaz-Nle-$OCH_2CN$)

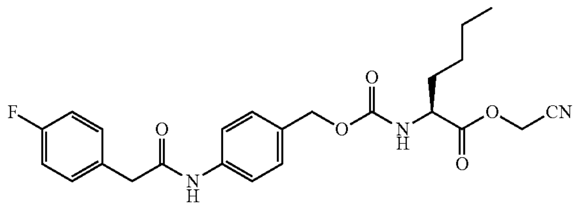 [SMILES: CCCC[C@H](NC(=O)OCc1ccc(NC(=O)Cc2ccc(F)cc2)cc1)C(=O)OCC#N]

Under a nitrogen atmosphere, 2-bromoacetonitrile (2.0 μL, 0.03 mmol) and N-ethyl-isopropylpropan-2-amine (DIPEA) (7.0 μL, 0.04 mmol) were added sequentially at room temperature to a solution of (2S)-2-[[4-[[2-(4-fluorophenyl)acetyl]amino]phenyl]methoxycarbonylamino] hexanoic acid (Compound ST02, F-Pnaz-Nle-OH) (8.3 mg, 0.02 mmol) in acetonitrile (0.1 mL). The reaction mixture was stirred at room temperature for 16 hours, and then the reaction solution was concentrated to give cyanomethyl (2S)-2-[[4-[[2-(4-fluorophenyl)acetyl]amino]phenyl] methoxycarbonylamino]hexanoate (Compound ST03, F-Pnaz-Nle-$OCH_2CN$) as a crude product. The obtained crude product was dissolved in acetonitrile (0.45 mL) and directly used in the next step.

LCMS (ESI) m/z=454.4 (M−H)−

Retention time: 0.83 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl) acetyl]amino]phenyl]methoxycarbonylamino] hexanoate (Compound ST04, F-Pnaz-Nle-pCpA)

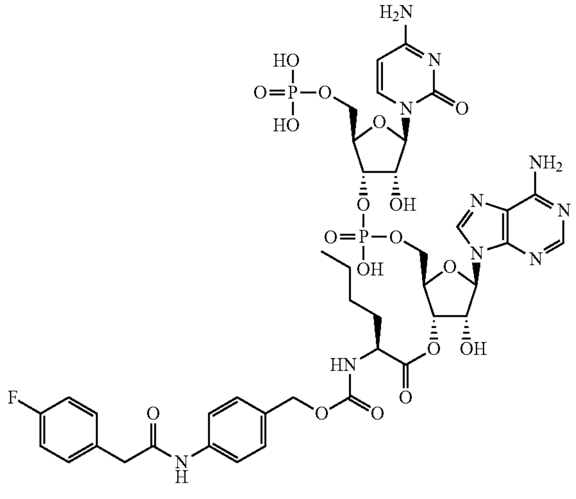 [SMILES: CCCC[C@H](NC(=O)OCc1ccc(NC(=O)Cc2ccc(F)cc2)cc1)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl) oxy)-4-((tetrahydrofuran-2-yl)oxy)tetrahydrofuran-2-yl) methyl dihydrogenphosphate (22 mg, 0.03 mmol) synthesized by the method described in the literature (Helv. Chim. Acta, 90, 297-310) was dissolved in Buffer A (9 mL), a solution of cyanomethyl (2S)-2-[[4-[[2-(4-fluorophenyl) acetyl]amino]phenyl]methoxycarbonylamino]hexanoate (Compound ST03, F-Pnaz-Nle-$OCH_2CN$) in acetonitrile (0.45 mL, 0.02 mmol) was added thereto, and this was stirred at room temperature for 90 min. The reaction solution was cooled to 0° C., and then trifluoroacetic acid (0.45 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST04, F-Pnaz-Nle-pCpA) (5.7 mg, 27%).

LCMS (ESI) m/z=1049.7 (M−H)−

Retention time: 0.54 min (analysis condition SQDFA05_02)

Buffer A was prepared as follows.

Acetic acid was added to an aqueous solution of N,N,N-trimethylhexadecan-1-aminium chloride (6.40 g, 20 mmol) and imidazole (6.81 g, 100 mmol) to give Buffer A (1 L), which was 20 mM N,N,N-trimethylhexadecan-1-aminium and 100 mM imidazole at pH 8.

Synthesis of (2S)-2-amino-3-[(5-fluoropyridin-3-yl)methoxy]propanoic acid (Compound ST05, S3F5MePyr-OH)

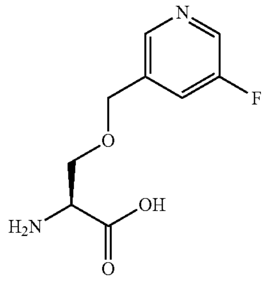 [SMILES: N[C@@H](COCc1cncc(F)c1)C(=O)O]

Under a nitrogen atmosphere, DCM (0.2 mL) and $H_2O$ (0.2 mL) were added at room temperature to (2S)-2-(9H-fluoren-9-ylmethoxycarbonylamino)-3-[(5-fluoropyridin-3-yl)methoxy]propanoic acid (43.6 mg, 0.10 mmol) synthesized by the method described in the patent literature (WO2018225864A1), 4-(3-phenylpropyl)piperidine (63.5 µL, 0.3 mmol) was then added at room temperature, and this mixture was stirred for one hour. The reaction mixture was left to stand, and the aqueous layer was purified by reverse-phase silica gel column chromatography (0.1% aqueous formic acid solution/0.1% formic acid-acetonitrile solution) to give (2S)-2-amino-3-[(5-fluoropyridin-3-yl)methoxy]propanoic acid (Compound ST05, S3F5MePyr-OH) (14 mg, 66%).

LCMS (ESI) m/z=213.0 (M−H)−

Retention time: 0.19 min (analysis condition SQDFA05_02)

Synthesis of (2S)-2-[[4-[[2-(4-fluorophenyl)acetyl]amino]phenyl]methoxycarbonylamino]-3-[(5-fluoropyridin-3-yl)methoxy]propanoic acid (Compound ST06, F-Pnaz-S3F5MePyr-OH)

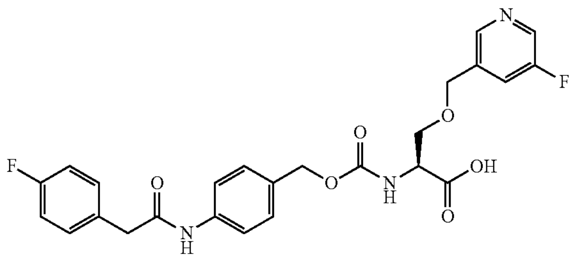 [SMILES: O=C(Cc1ccc(F)cc1)Nc1ccc(COC(=O)N[C@@H](COCc2cncc(F)c2)C(=O)O)cc1]

Under a nitrogen atmosphere, DMSO (250 µL) and triethylamine (16.0 µL, 0.12 mmol) were added at room temperature to a mixture of (2S)-2-amino-3-[(5-fluoropyridin-3-yl)methoxy]propanoic acid (Compound ST05, S3F5MePyr-OH) (10.7 mg, 0.05 mmol) and (4-nitrophenyl)-4-(2-(4-fluorophenyl)acetamide)benzyl carbonate (21.2 mg, 0.05 mmol) synthesized by the method described in the patent literature (WO 2018143145 A1). The reaction mixture was placed at room temperature and stirred for one hour, and then purified by reverse-phase silica gel column chromatography (0.1% aqueous formic acid solution/0.1% formic acid-acetonitrile solution) to give (2S)-2-[[4-[[2-(4-fluorophenyl)acetyl]amino]phenyl]methoxycarbonylamino]-3-[(5-fluoropyridin-3-yl)methoxy]propanoic acid (Compound ST06, F-Pnaz-S3F5MePyr-OH) (23 mg, 92%).

LCMS (ESI) m/z=498.4 (M−H)−

Retention time: 0.66 min (analysis condition SQDFA05_02)

Synthesis of cyanomethyl (2S)-2-[[4-[[2-(4-fluorophenyl)acetyl]amino]phenyl]methoxycarbonylamino]-3-[(5-fluoropyridin-3-yl)methoxy]propanoate (Compound ST07. F-Pnaz-S3F5MePyr-$OCH_2CN$)

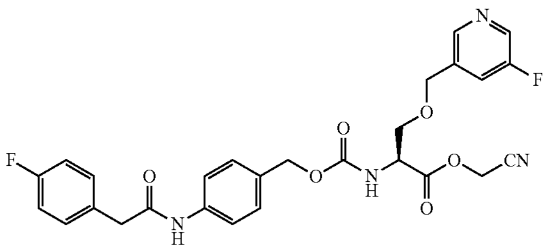 [SMILES: N#CCOC(=O)[C@H](COCc1cncc(F)c1)NC(=O)OCc1ccc(NC(=O)Cc2ccc(F)cc2)cc1]

Under a nitrogen atmosphere, 2-bromoacetonitrile (2.0 µL, 0.03 mmol) and N-ethyl-isopropylpropan-2-amine (DIPEA) (7.0 µL, 0.04 mmol) were added sequentially at room temperature to a solution of (2S)-2-[[4-[[2-(4-fluorophenyl)acetyl]amino]phenyl]methoxycarbonylamino]-3-[(5-fluoropyridin-3-yl)methoxy]propanoic acid (Compound ST06, F-Pnaz-S3F5MePyr-OH) (9.99 mg, 0.02 mmol) in acetonitrile (0.1 mL). The reaction mixture was stirred at room temperature for 16 hours, and then the reaction solution was concentrated to give cyanomethyl (2S)-2-[[4-[[2-(4-fluorophenyl)acetyl]amino]phenyl]methoxycarbonylamino]-3-[(5-fluoropyridin-3-yl)methoxy]propanoate (Compound ST07, F-Pnaz-S3F5MePyr-$OCH_2CN$) as a crude product. The obtained crude product was dissolved in acetonitrile (0.45 mL) and directly used in the next step.

LCMS (ESI) m/z=537.3 (M−H)−

Retention time: 0.74 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonylamino]-3-[(5-fluoropyridin-3-yl)methoxy]propanoate (Compound ST08, F-Pnaz-S3F5MePyr-pCpA)

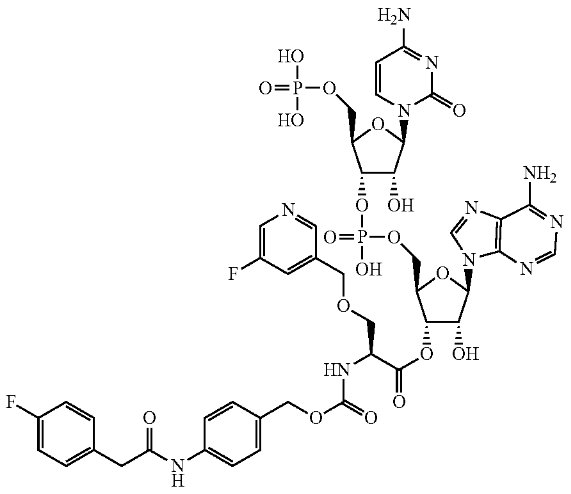 [SMILES: Nc1ccn([C@@H]2O[C@H](COP(=O)(O)O)[C@@H](OP(=O)(O)OC[C@H]3O[C@@H](n4cnc5c(N)ncnc54)[C@H](O)[C@@H]3OC(=O)[C@H](COCc3cncc(F)c3)NC(=O)OCc3ccc(NC(=O)Cc4ccc(F)cc4)cc3)[C@H]2O)c(=O)n1]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (22 mg, 0.03 mmol) synthesized by the method described in the literature (Helv. Chim. Acta, 90, 297-310) was dissolved in Buffer A (9 mL), a solution of cyanomethyl (2S)-2-[[4-[[2-(4-fluorophenyl)acetyl]amino]phenyl]methoxycarbonylamino]-3-[(5-fluoropyridin-3-yl)methoxy]propanoate (Compound ST07, F-Pnaz-S3F5MePyr-$OCH_2CN$) in acetonitrile (0.45 mL, 0.02 mmol) was added thereto, and this was stirred at room temperature for 40 min. The reaction solution was cooled to 0° C., and then trifluoroacetic acid (0.45 mL) was added. The reaction solution was stirred at 0° C. for one hour, and then purified by reverse-phase silica gel column chromatography (0.05% aqueous trifluoroacetic acid solution/0.05% trifluoroacetic acid-acetonitrile) to give the title compound (Compound ST08, F-Pnaz-S3F5MePyr-pCpA) (6.5 mg, 29%).

LCMS (ESI) m/z=1132.7 (M−H)−

Retention time: 0.51 min (analysis condition SQDFA05_02)

Synthesis of (2S)-1-[[4-[[2-(4-fluorophenyl)acetyl]amino]phenyl]methoxycarbonyl]pyrrolidine-2-carboxylic acid (Compound ST09, F-Pnaz-Pro-OH)

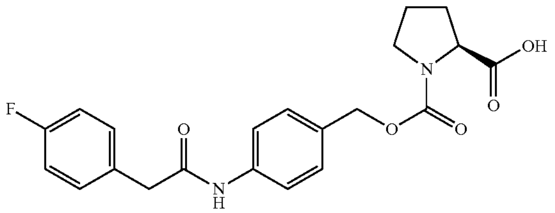 [SMILES: O=C(Cc1ccc(F)cc1)Nc1ccc(COC(=O)N2CCC[C@H]2C(=O)O)cc1]

Under a nitrogen atmosphere, DMSO (2.00 mL) and triethylamine (128 μL, 0.92 mmol) were added at room temperature to a mixture of L-proline (46.1 mg, 0.40 mmol) and (4-nitrophenyl)-4-(2-(4-fluorophenyl)acetamide benzyl carbonate (178 mg, 0.42 mmol) synthesized by the method described in the patent literature (WO 2018143145 A1). The reaction mixture was placed at room temperature and stirred for two days, and then purified by reverse-phase silica gel column chromatography (0.1% aqueous formic acid solution/0.1% formic acid-acetonitrile solution) to give (2S)-1-[[4-[[2-(4-fluorophenyl)acetyl]amino]phenyl]methoxycarbonyl]pyrrolidine-2-carboxylic acid (Compound ST09, F-Pnaz-Pro-OH) (157 mg, 98%).

LCMS (ESI) m/z=399.2 (M−H)−

Retention time: 0.66 min (analysis condition SQDFA05_02)

Synthesis of 2-O-(cyanomethyl) 1-O-[[4-[[2-(4-fluorophenyl)acetyl]amino]phenyl]methyl] (2S)-pyrrolidin-1,2-dicarboxylate (Compound ST10, F-Pnaz-Pro-$OCH_2CN$)

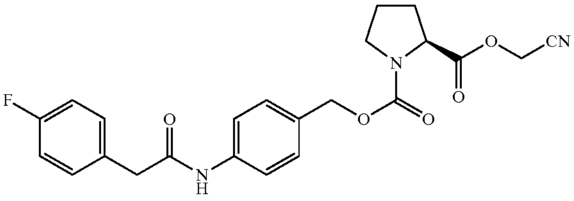 [SMILES: N#CCOC(=O)[C@@H]1CCCN1C(=O)OCc1ccc(NC(=O)Cc2ccc(F)cc2)cc1]

Under a nitrogen atmosphere, 2-bromoacetonitrile (13.0 μL, 0.20 mmol) and N-ethyl-isopropylpropan-2-amine (DIPEA) (35.0 μL, 0.20 mmol) were added sequentially at room temperature to a solution of (2S)-1-[[4-[[2-(4-fluorophenyl)acetyl]amino]phenyl]methoxycarbonyl]pyrrolidine-2-carboxylic acid (Compound ST09, F-Pnaz-Pro-OH) (40.0 mg, 0.10 mmol) in acetonitrile (0.5 mL). The reaction mixture was stirred at room temperature for 16 hours, and then the reaction solution was concentrated to give 2-O-(cyanomethyl) 1-O-[[4-[[2-(4-fluorophenyl)acetyl]amino]phenyl]methyl](2S)-pyrrolidin-1,2-dicarboxylate (Compound ST10, F-Pnaz-Pro-$OCH_2CN$) as a crude product. The obtained crude product was dissolved in acetonitrile (3.00 mL) and directly used in the next step.

LCMS (ESI) m/z=438.3 (M−H)−

Retention time: 0.76 min (analysis condition SQDFA05_02)

Synthesis of 2-O-[(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl]1-O-[[4-[[2-(4-fluorophenyl)acetyl]amino]phenyl]methyl] (2S)-pyrrolidin-1,2-dicarboxylate (Compound ST11, F-Pnaz-Pro-pCpA)

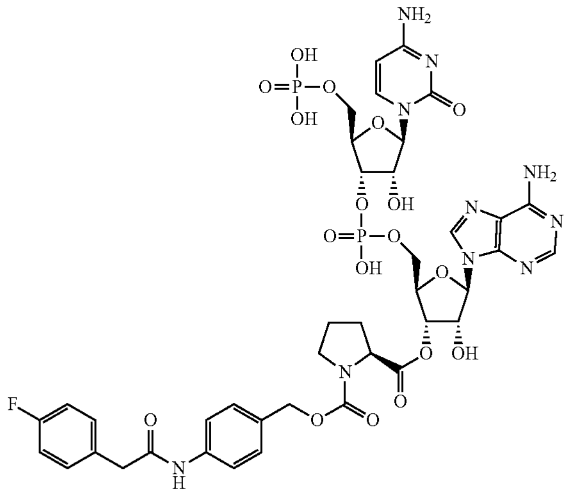 [SMILES: Nc1ccn([C@@H]2O[C@H](COP(=O)(O)O)[C@@H](OP(=O)(O)OC[C@H]3O[C@@H](n4cnc5c(N)ncnc54)[C@H](O)[C@@H]3OC(=O)[C@@H]3CCCN3C(=O)OCc3ccc(NC(=O)Cc4ccc(F)cc4)cc3)[C@H]2O)c(=O)n1]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (72.2 mg, 0.10 mmol) synthesized by the method described in the literature (Helv. Chim. Acta, 90, 297-310) was dissolved in Buffer A (60 mL), a solution of 2-O-(cyanomethyl) 1-O-[[4-[[2-(4-fluorophenyl)acetyl]amino]phenyl]methyl](2S)-pyrrolidin-1,2-dicarboxylate (Compound ST10, F-Pnaz-Pro-$OCH_2CN$) in acetonitrile (3.00 mL, 0.10 mmol) was added thereto, and this was stirred at room temperature for 20 hours. The reaction solution was cooled to 0° C., and then trifluoroacetic acid (3.00 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST11, F-Pnaz-Pro-pCpA) (11 mg, 11%).

LCMS (ESI) m/z=1033.4 (M−H)−

Retention time: 0.49 min (analysis condition SQDFA05_02)

Synthesis of 2-[[4-[[2-(4-fluorophenyl)acetyl]amino]phenyl]methoxycarbonylamino]acetic acid (Compound ST12, F-Pnaz-Gly-OH)

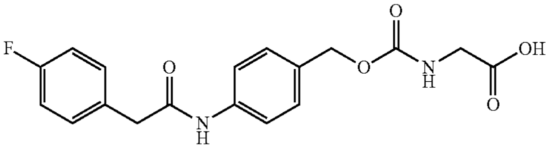

Under a nitrogen atmosphere, DMSO (2.00 mL) and triethylamine (128 μL, 0.92 mmol) were added at room temperature to a mixture of glycine (30.0 mg, 0.40 mmol) and (4-nitrophenyl)-4-(2-(4-fluorophenyl)acetamide)benzyl carbonate (178 mg, 0.42 mmol) synthesized by the method described in the patent literature (WO 2018143145 A1). The reaction mixture was placed at room temperature and stirred for two days, and then purified by reverse-phase silica gel column chromatography (0.1% aqueous formic acid solution/0.1% formic acid-acetonitrile solution) to give 2-[[4-[[2-(4-fluorophenyl)acetyl]amino]phenyl]methoxycarbonylamino]acetic acid (Compound ST12, F-Pnaz-Gly-OH) (57 mg, 40%).

LCMS (ESI) m/z=359.2 (M−H)−

Retention time: 0.60 min (analysis condition SQDFA05_02)

Synthesis of cyanomethyl 2-[[4-[[2-(4-fluorophenyl)acetyl]amino]phenyl]methoxycarbonylamino]acetate (Compound ST13, F-Pnaz-Gly-$OCH_2CN$)

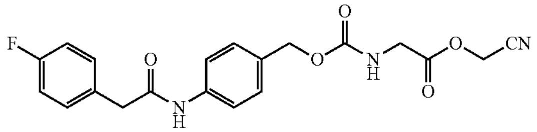 [SMILES: N#CCOC(=O)CNC(=O)OCc1ccc(NC(=O)Cc2ccc(F)cc2)cc1]

Under a nitrogen atmosphere, 2-bromoacetonitrile (13.0 μL, 0.20 mmol) and N-ethyl-isopropylpropan-2-amine (DIPEA) (35.0 μL, 0.20 mmol) were added sequentially at room temperature to a solution of 2-[[4-[[2-(4-fluorophenyl)acetyl]amino]phenyl]methoxycarbonylamino]acetic acid (Compound ST12, F-Pnaz-Gly-OH) (36.0 mg, 0.10 mmol) in acetonitrile (0.5 mL). The reaction mixture was stirred at room temperature for 16 hours, and then the reaction solution was concentrated to give cyanomethyl 2-[[4-[[2-(4-fluorophenyl)acetyl]amino]phenyl]methoxycarbonylamino]acetate (Compound ST13, F-Pnaz-Gly-$OCH_2CN$) as a crude product. The obtained crude product was dissolved in acetonitrile (3.00 mL) and directly used in the next step.

LCMS (ESI) m/z=398.3 (M−H)−

Retention time: 0.69 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] 2-[[4-[[2-(4-fluorophenyl) acetyl]amino]phenyl]methoxycarbonylamino]acetate (Compound ST14, F-Pnaz-Gly-pCpA)

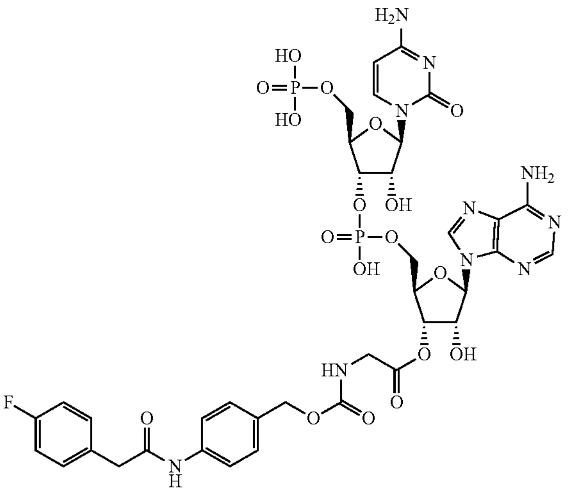 [SMILES: Nc1ccn([C@@H]2O[C@H](COP(=O)(O)O)[C@@H](OP(=O)(O)OC[C@H]3O[C@@H](n4cnc5c(N)ncnc54)[C@H](O)[C@@H]3OC(=O)CNC(=O)OCc3ccc(NC(=O)Cc4ccc(F)cc4)cc3)[C@H]2O)c(=O)n1]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl) oxy)-4-((tetrahydrofuran-2-yl)oxy)tetrahydrofuran-2-yl) methyl dihydrogenphosphate (72.2 mg, 0.10 mmol) synthesized by the method described in the literature (Helv. Chim. Acta, 90, 297-310) was dissolved in Buffer A (60 mL), a solution of cyanomethyl 2-[[4-[[2-(4-fluorophenyl) acetyl]amino]phenyl]methoxycarbonylamino]acetate (Compound ST13, F-Pnaz-Gly-$OCH_2CN$) in acetonitrile (3.00 mL, 0.10 mmol) was added thereto, and this was stirred at room temperature for 90 min. The reaction solution was cooled to 0° C., and then trifluoroacetic acid (3.00 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST14, F-Pnaz-Gly-pCpA) (16 mg, 16%).

LCMS (ESI) m/z=993.6 (M−H)−

Retention time: 0.47 min (analysis condition SQDFA05_02)

Synthesis of (2S)-2-[[4-[[2-(4-fluorophenyl)acetyl] amino]phenyl]methoxycarbonylamino]-3-hydroxybutanoic acid (Compound ST115, F-Pnaz-Thr-OH)

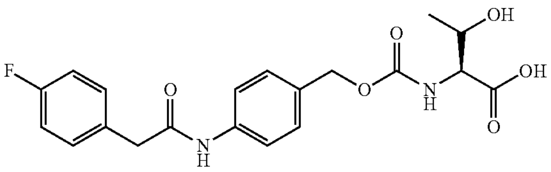 [SMILES: CC(O)[C@H](NC(=O)OCc1ccc(NC(=O)Cc2ccc(F)cc2)cc1)C(=O)O]

Under a nitrogen atmosphere, DMSO (2.00 mL) and triethylamine (128 μL, 0.92 mmol) were added at room temperature to a mixture of L-threonine (47.6 mg, 0.40 mmol) and (4-nitrophenyl)-4-(2-(4-fluorophenyl)acetamide) benzyl carbonate (178 mg, 0.42 mmol) synthesized by the method described in the patent literature (WO 2018143145 A1). The reaction mixture was placed at room temperature and stirred for two days, and then purified by reverse-phase silica gel column chromatography (0.1% aqueous formic acid solution/0.1% formic acid-acetonitrile solution) to give (2S)-2-[[4-[[2-(4-fluorophenyl)acetyl]amino]phenyl] methoxycarbonylamino]-3-hydroxybutanoic acid (Compound ST15, F-Pnaz-Thr-OH) (141 mg, 87%).

LCMS (ESI) m/z=403.3 (M−H)−

Retention time: 0.59 min (analysis condition SQDFA05_02)

Synthesis of cyanomethyl (2S)-2-[[4-[[2-(4-fluorophenyl)acetyl]amino]phenyl]methoxycarbonylamino]-3-hydroxybutanoate (Compound ST16, F-Pnaz-Thr-$OCH_2CN$)

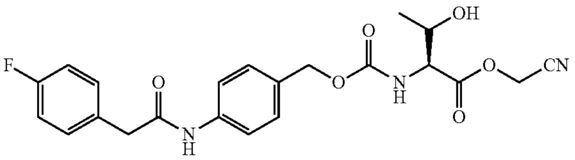 [SMILES: CC(O)[C@H](NC(=O)OCc1ccc(NC(=O)Cc2ccc(F)cc2)cc1)C(=O)OCC#N]

Under a nitrogen atmosphere, 2-bromoacetonitrile (268 μL, 4.00 mmol) and N-ethyl-isopropylpropan-2-amine (DIPEA) (69.9 μL, 0.40 mmol) were added sequentially at room temperature to a solution of (2S)-2-[[4-[[2-(4-fluorophenyl)acetyl]amino]phenyl]methoxycarbonylamino]-3-hydroxybutanoic acid (Compound ST15, F-Pnaz-Thr-OH) (81.0 mg, 0.20 mmol) in acetonitrile (1.0 mL). The reaction mixture was stirred at room temperature for 3 hours, and then purified by reverse-phase silica gel column chromatography (0.1% aqueous formic acid solution/0.1% formic acid-acetonitrile solution) to give cyanomethyl (2S)-2-[[4-[[2-(4-fluorophenyl)acetyl]amino]phenyl]methoxycarbonylamino]-3-hydroxybutanoate (Compound ST16, F-Pnaz-Thr-$OCH_2CN$) (72.0 mg, 81%).

LCMS (ESI) m/z=442.3 (M−H)−

Retention time: 0.68 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S,3R)-2-[[4-[[2-(4-fluorophenyl)acetyl]amino]phenyl]methoxycarbonylamino]-3-hydroxybutanoate (Compound ST17, F-Pnaz-Thr-pCpA)

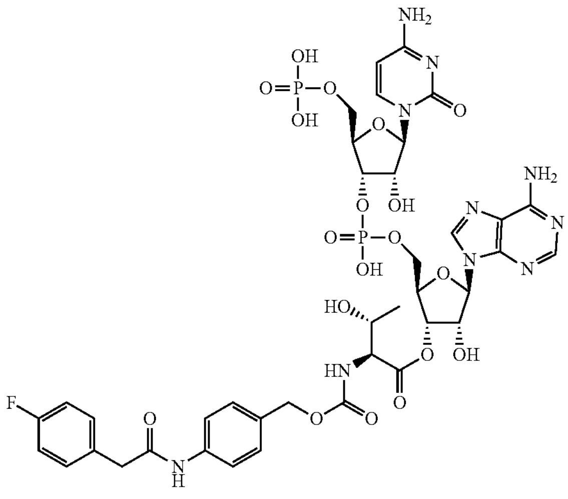 [SMILES: C[C@@H](O)[C@H](NC(=O)OCc1ccc(NC(=O)Cc2ccc(F)cc2)cc1)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (72.2 mg, 0.10 mmol) synthesized by the method described in the literature (Helv. Chim. Acta, 90, 297-310) was dissolved in Buffer A (60 mL), a solution of cyanomethyl (2S)-2-[[4-[[2-(4-fluorophenyl)acetyl]amino]phenyl]methoxycarbonylamino]-3-hydroxybutanoate (Compound ST16, F-Pnaz-Thr-$OCH_2CN$) in acetonitrile (3.00 mL, 0.10 mmol) was added thereto, and this was stirred at room temperature for 90 min. The reaction solution was cooled to 0° C., and then trifluoroacetic acid (3.00 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST17, F-Pnaz-Thr-pCpA) (7 mg, 7%).

LCMS (ESI) m/z=1037.4 (M−H)−

Retention time: 0.48 min (analysis condition SQDFA05_02)

Synthesis of (2S)-2-[[4-[[2-(4-fluorophenyl)acetyl]amino]phenyl]methoxycarbonylamino]-4-methylpentanoic acid (Compound ST18, F-Pnaz-Leu-OH)

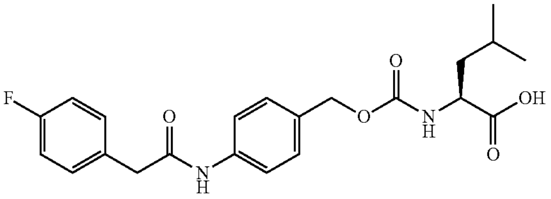 [SMILES: CC(C)C[C@H](NC(=O)OCc1ccc(NC(=O)Cc2ccc(F)cc2)cc1)C(=O)O]

Under a nitrogen atmosphere, DMSO (0.50 mL) and triethylamine (32.1 μL, 0.23 mmol) were added at room temperature to a mixture of L-leucine (13.1 mg, 0.10 mmol) and (4-nitrophenyl)-4-(2-(4-fluorophenyl)acetamide)benzyl carbonate (42.4 mg, 0.10 mmol) synthesized by the method described in the patent literature (WO 2018143145 A1). The reaction mixture was placed at room temperature and stirred for one hour, and then purified by reverse-phase silica gel column chromatography (0.1% aqueous formic acid solution/0.1% formic acid-acetonitrile solution) to give (2S)-2-[[4-[[2-(4-fluorophenyl)acetyl]amino]phenyl]methoxycarbonylamino]-4-methylpentanoic acid (Compound ST18, F-Pnaz-Leu-OH) (28 mg, 67%).

LCMS (ESI) m/z=415.3 (M−H)−

Retention time: 0.73 min (analysis condition SQDFA05_02)

Synthesis of cyanomethyl (2S)-2-[[4-[[2-(4-fluorophenyl)acetyl]amino]phenyl]methoxycarbonylamino]-4-methylpentanoate (Compound ST19, F-Pnaz-Leu-$OCH_2CN$)

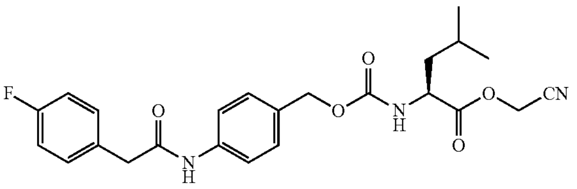 [SMILES: CC(C)C[C@H](NC(=O)OCc1ccc(NC(=O)Cc2ccc(F)cc2)cc1)C(=O)OCC#N]

Under a nitrogen atmosphere, 2-bromoacetonitrile (20.0 μL, 0.30 mmol) and N-ethyl-isopropylpropan-2-amine (DIPEA) (7.86 μL, 0.05 mmol) were added sequentially at room temperature to a solution of (2S)-2-[[4-[[2-(4-fluorophenyl)acetyl]amino]phenyl]methoxycarbonylamino]-4-methylpentanoic acid (Compound ST18, F-Pnaz-Leu-OH) (12.0 mg, 0.03 mmol) in acetonitrile (75.0 μL). The reaction mixture was stirred at room temperature for one hour, and then the reaction solution was concentrated to give cyanomethyl (2S)-2-[[4-[[2-(4-fluorophenyl)acetyl]amino]phenyl]methoxycarbonylamino]-4-methylpentanoate (Compound ST19, F-Pnaz-Leu-$OCH_2CN$) as a crude product. The obtained crude product was dissolved in acetonitrile (0.75 mL) and directly used in the next step.

LCMS (ESI) m/z=454.3 (M−H)−

Retention time: 0.82 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonylamino]-4-methylpentanoate (Compound ST20, F-Pnaz-Leu-pCpA)

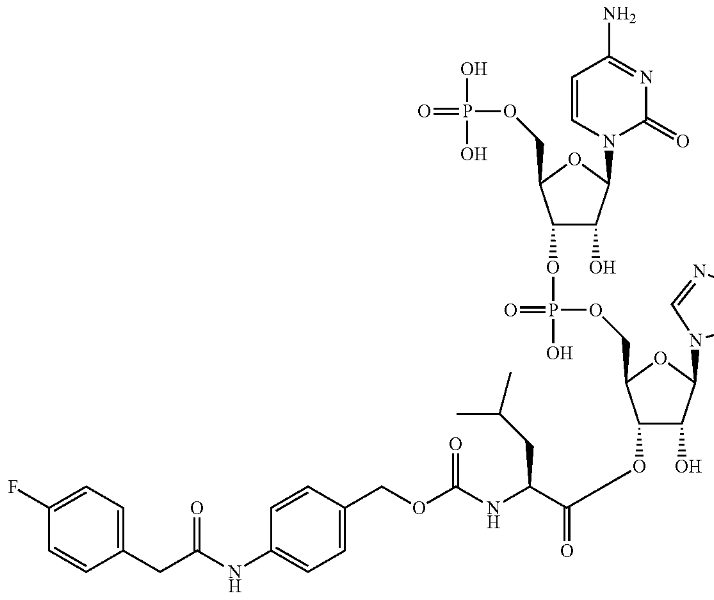

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (72.2 mg, 0.10 mmol) synthesized by the method described in the literature (Helv. Chim. Acta, 90, 297-310) was dissolved in Buffer A (15 mL), a solution of cyanomethyl (2S)-2-[[4-[[2-(4-fluorophenyl)acetyl]amino]phenyl]methoxycarbonylamino]-4-methylpentanoate (Compound ST19, F-Pnaz-Leu-$OCH_2CN$) in acetonitrile (0.75 mL, 0.10 mmol) was added thereto, and this was stirred at room temperature for 60 min. The reaction solution was cooled to 0° C., and then trifluoroacetic acid (0.75 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST20, F-Pnaz-Leu-pCpA) (9.6 mg, 31%).

LCMS (ESI) m/z=1049.6 (M−H)−

Retention time: 0.54 min (analysis condition SQDFA05_02)

Synthesis of 2-[[4-[[2-(4-fluorophenyl)acetyl]amino]phenyl]methoxycarbonyl-methylamino]acetic acid (Compound ST21, F-Pnaz-MeG-OH)

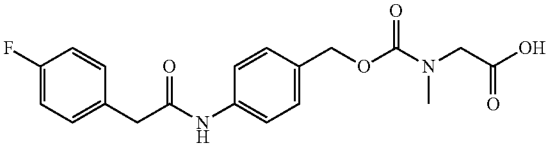 [SMILES: CN(CC(=O)O)C(=O)OCc1ccc(NC(=O)Cc2ccc(F)cc2)cc1]

Under a nitrogen atmosphere, DMSO (15 mL) and triethylamine (953.4 mg, 9.42 mmol) were added at room temperature to a mixture of sarcosine (483 mg, 5.42 mmol) and (4-nitrophenyl)-4-(2-(4-fluorophenyl)acetamide)benzyl) carbonate (2.0 g, 4.71 mmol) synthesized by the method described in the patent literature (WO 2018143145 A1). The reaction mixture was placed at room temperature and stirred for 16 hours, and then purified by reverse-phase silica gel column chromatography (0.1% aqueous formic acid solution/0.1% formic acid-acetonitrile solution) to give 2-[[4-[[2-(4-fluorophenyl)acetyl]amino]phenyl]methoxycarbonyl-methylamino]acetic acid (Compound ST21, F-Pnaz-MeG-OH) (1.4 g, 79%).

LCMS (ESI) m/z=397 (M+Na)+

Retention time: 0.88 min (analysis condition SMD method 3)

Synthesis of cyanomethyl 2-[[4-[[2-(4-fluorophenyl) acetyl]amino]phenyl]methoxycarbonyl-methyl-amino]acetate (Compound ST22, F-Pnaz-MeG-$OCH_2CN$)

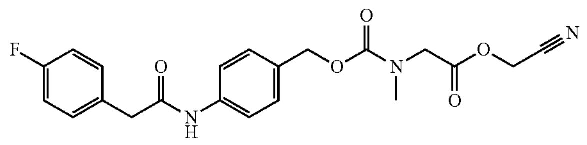 [SMILES: CN(CC(=O)OCC#N)C(=O)OCc1ccc(NC(=O)Cc2ccc(F)cc2)cc1]

Under a nitrogen atmosphere, 2-[[4-[[2-(4-fluorophenyl) acetyl]amino]phenyl]methoxycarbonyl-methylamino]acetic acid (Compound ST21, F-Pnaz-MeG-OH) (1.38 g, 3.69 mmol) and N-ethyl-isopropylpropan-2-amine (DIPEA) (0.95 g, 7.38 mmol) were dissolved in DMF (28 mL), 2-bromoacetonitrile (1.74 g, 14.75 mmol) was added thereto at room temperature, and the mixture was stirred at room temperature for 16 hours. The reaction solution was concentrated and purified by normal-phase silica gel column chromatography (ethyl acetate/petroleum ether) to give cyanomethyl 2-[[4-[[2-(4-fluorophenyl)acetyl]amino]phenyl] methoxycarbonyl-methylamino]acetate (Compound ST22, F-Pnaz-MeG-$OCH_2CN$) (1.2 g, 79%).

LCMS (ESI) m/z=436 (M+Na)+

Retention time: 0.70 min (analysis condition SMD method 4)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] 2-[[4-[[2-(4-fluorophenyl) acetyl]amino]phenyl]methoxycarbonyl-methylamino]acetate (Compound ST23. F-Pnaz-MeG-pCpA)

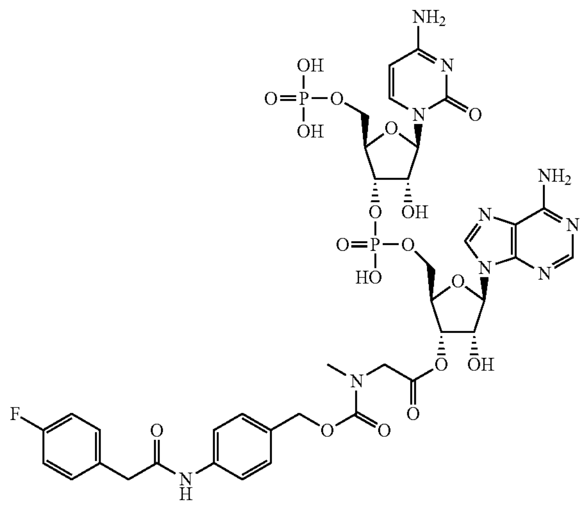 [SMILES: CN(CC(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O)C(=O)OCc1ccc(NC(=O)Cc2ccc(F)cc2)cc1]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl) oxy)-4-((tetrahydrofuran-2-yl)oxy)tetrahydrofuran-2-yl) methyl dihydrogenphosphate (422 mg, 0.58 mmol) synthesized by the method described in the literature (Helv. Chim. Acta, 90, 297-310) was dissolved in Buffer A (100 mL), a solution of cyanomethyl 2-[[4-[[2-(4-fluorophenyl) acetyl]amino]phenyl]methoxycarbonyl-methylamino]acetate (Compound ST22, F-Pnaz-MeG-$OCH_2CN$) (120.7 mg, 0.29 mmol) in acetonitrile (5 mL) was added dropwise thereto over 15 min using a syringe pump, and this was stirred at room temperature for 5 hours. Trifluoroacetic acid (2.3 mL) was added to the reaction solution, then the reaction solution was freeze-dried, and then this was purified by reverse-phase silica gel column chromatography (0.05% aqueous trifluoroacetic acid solution/0.05% trifluoroacetic acid-acetonitrile) to give the title compound (Compound ST23, F-Pnaz-MeG-pCpA) (76.7 mg, 26%).

LCMS (ESI) m/z=1007.5 (M−H)−

Retention time: 0.48 min (analysis condition SQDFA05_02)

The synthetic intermediate of Compound ST28 was synthesized according to the following scheme.

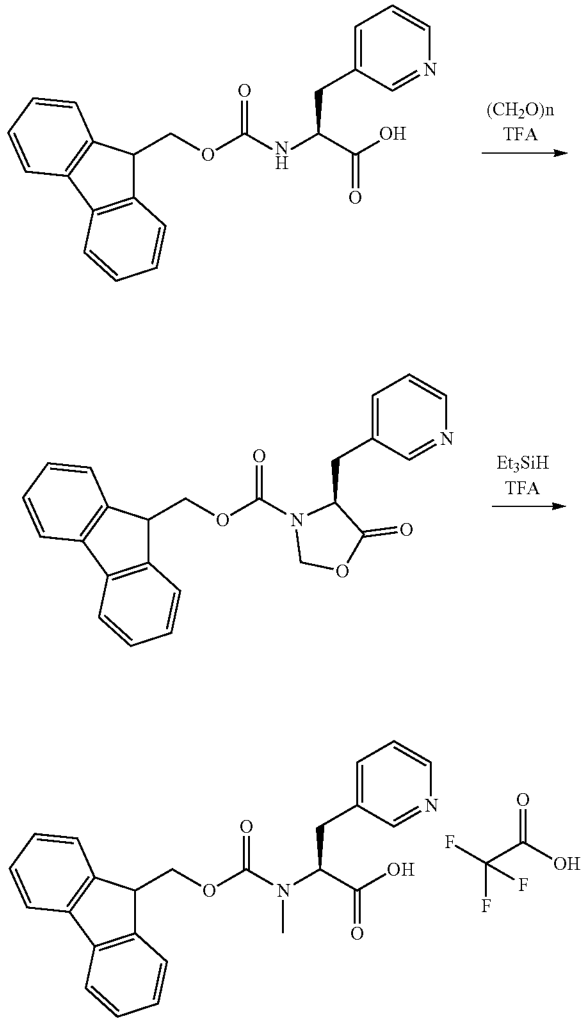

Synthesis of (2S)-2-[9H-fluoren-9-ylmethoxycarbonyl(methyl)amino]-3-pyridin-3-ylpropanoic acid 2,2,2-trifluoroacetic acid (Compound ST24, Fmoc-MeA3Pyr-OH. TFA)

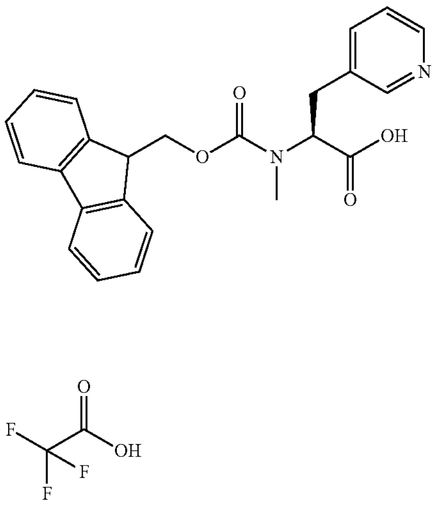

(2S)-2-(9H-Fluoren-9-ylmethoxycarbonylamino)-3-pyridin-3-ylpropanoic acid (15 g, 38.62 mmol), trifluoroacetic acid (27 mL, 348 mmol), and paraformaldehyde ($(CH_2O)_n$) (3.48 g, 116 mmol) were suspended in toluene (50 mL), and this was stirred under a nitrogen atmosphere at 40° C. for 16 hours. After cooling to room temperature, the reaction solution was concentrated under reduced pressure. The residue was dissolved in DCM, and washed with a saturated aqueous sodium bicarbonate solution. The organic layer was dried over anhydrous sodium sulfate, and then it was subjected to filtration and the solvent was removed by concentration under reduced pressure to give (9H-fluoren-9-yl) methyl (S)-5-oxo-4-(pyridin-3-ylmethyl)oxazolidine-3-carboxylate as a crude product.

The obtained crude product, (9H-fluoren-9-yl)methyl (S)-5-oxo-4-(pyridin-3-ylmethyl)oxazolidine-3-carboxylate (18 g, 44.95 mmol), was dissolved in dichloroethane (100 mL), and triethylsilane ($Et_3SiH$) (47 g, 404.20 mmol) and trifluoroacetic acid (100 mL) were added thereto at room temperature. The reaction solution was stirred under a nitrogen atmosphere at 70° C. for 16 hours, and then concentrated under reduced pressure. The resulting residue was dissolved in isopropyl acetate, and a mixed solution of t-butyl methyl ether and hexane (9:1) was added thereto. This solution was stirred at room temperature for 20 min, and then left to stand at 4° C. for one hour. The formed precipitates were collected by filtration, and this was washed with a cooled, mixed solution of t-butyl methyl ether and hexane (9:1) to give (2S)-2-[9H-fluoren-9-ylmethoxycarbonyl(methyl)amino]-3-pyridin-3-ylpropanoic acid 2,2,2-trifluoroacetic acid (Compound ST24, Fmoc-MeA3Pyr-OH·TFA) (19 g, 95%).

LCMS (ESI) m/z=403 (M+H)+

Retention time: 0.77 min (analysis condition SMD method 1)

Synthesis of (2S)-2-(methylamino)-3-pyridin-3-ylpropanoic acid (Compound ST25, MeA3Pyr-OH)

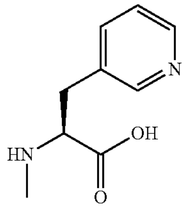

DMF (72 mL) and piperidine (28.5 mL) were added to (2S)-2-[9H-fluoren-9-ylmethoxycarbonyl(methyl)amino]-3-pyridin-3-ylpropanoic acid; 2,2,2-trifluoroacetic acid (Compound ST24, Fmoc-MeA3Pyr-OH·TFA) (19 g, 47.21 mmol) at room temperature, and the reaction mixture was stirred at room temperature for 3 hours. Diethyl ether (140 mL) and hexane (280 mL) were added thereto, and this was stirred at room temperature for another 3 hours. The formed precipitates were collected by filtration to quantitatively give (2S)-2-(methylamino)-3-pyridin-3-ylpropanoic acid (Compound ST25, MeA3Pyr-OH) (7 g).

LCMS (ESI) m/z=181 (M+H)+

Retention time: 0.15 min (analysis condition SMD method 2)

Synthesis of (2S)-2-[[4-[[2-(4-fluorophenyl)acetyl]amino]phenyl]methoxycarbonyl-methylamino]-3-pyridin-3-ylpropanoic acid (Compound ST26, F-Pnaz-MeA3Pyr-OH)

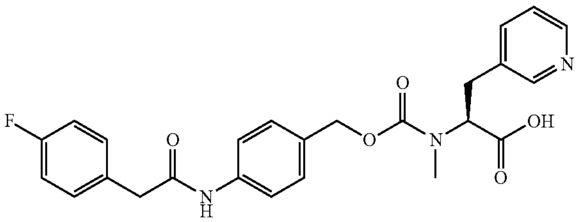 [SMILES: CN(C(=O)OCc1ccc(NC(=O)Cc2ccc(F)cc2)cc1)[C@@H](Cc1cccnc1)C(=O)O]

Under a nitrogen atmosphere, DMSO (15 mL) and triethylamine (950 mg, 9.43 mmol) were added at room temperature to a mixture of (2S)-2-(methylamino)-3-pyridin-3-ylpropanoic acid (Compound ST25, MeA3Pyr-OH) (970 mg, 5.38 mmol) and (4-nitrophenyl)-4-(2-(4-fluorophenyl)acetamide)benzyl carbonate (2 g, 4.71 mmol) synthesized by the method described in the patent literature (WO 2018143145 A1). The reaction mixture was stirred at 40° C. for 16 hours, and then purified by reverse-phase silica gel column chromatography (0.1% aqueous formic acid solution/0.1% formic acid-acetonitrile solution) to give (2S)-2-[[4-[[2-(4-fluorophenyl)acetyl]amino]phenyl]methoxycarbonyl-methylamino]-3-pyridin-3-ylpropanoic acid (Compound ST26, F-Pnaz-MeA3Pyr-OH) (1.0 g, 46%).

LCMS (ESI) m/z=466 (M+H)+

Retention time: 0.98 min (analysis condition SMD method 3)

Synthesis of cyanomethyl (2S)-2-[[4-[[2-(4-fluorophenyl)acetyl]amino]phenyl]methoxycarbonyl-methylamino]-3-pyridin-3-ylpropanoate (Compound ST27, F-Pnaz-MeA3Pyr-$OCH_2CN$)

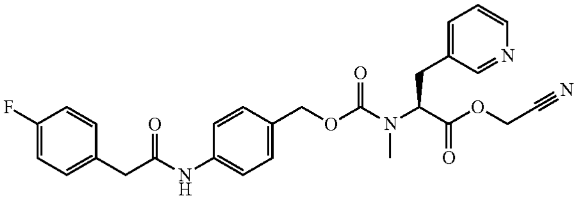 [SMILES: CN(C(=O)OCc1ccc(NC(=O)Cc2ccc(F)cc2)cc1)[C@@H](Cc1cccnc1)C(=O)OCC#N]

Under a nitrogen atmosphere, a mixture of (2S)-2-[[4-[[2-(4-fluorophenyl)acetyl]amino]phenyl]methoxycarbonyl-methylamino]-3-pyridin-3-ylpropanoic acid (Compound ST26, F-Pnaz-MeA3Pyr-OH) (800 mg, 1.72 mmol) and N-ethyl-isopropylpropan-2-amine (DIPEA) (444 mg, 3.44 mmol) was dissolved in DCM (20 mL), 2-bromoacetonitrile (818 mg, 6.82 mmol) was added thereto at room temperature, and the mixture was stirred at room temperature for 6 hours. The reaction solution was concentrated and purified by normal-phase silica gel column chromatography (ethyl acetate/petroleum ether) to give cyanomethyl (2S)-2-[[4-[[2-(4-fluorophenyl)acetyl]amino]phenyl]methoxycarbonyl-methylamino]-3-pyridin-3-ylpropanoate (Compound ST27, F-Pnaz-MeA3Pyr-$OCH_2CN$) (221 mg, 25%).

LCMS (ESI) m/z=505 (M+H)+

Retention time: 0.83 min (analysis condition SMD method 4)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonyl-methylamino]-3-pyridin-3-ylpropanoate (Compound ST28. F-Pnaz-MeA3Pyr-pCpA)

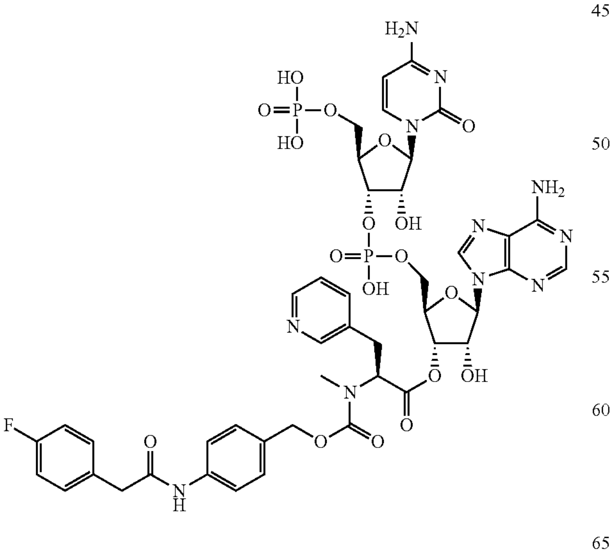

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (400 mg, 0.55 mmol) synthesized by the method described in the literature (Helv. Chim. Acta, 90, 297-310) was dissolved in Buffer A (100 mL), a solution of cyanomethyl (2S)-2-[[4-[[2-(4-fluorophenyl)acetyl]amino]phenyl]methoxycarbonyl-methylamino]-3-pyridin-3-ylpropanoate (Compound ST27, F-Pnaz-MeA3Pyr-$OCH_2CN$) (146 mg, 0.29 mmol) in acetonitrile (5 mL) was added dropwise thereto over 15 min using a syringe pump, and this was stirred at room temperature for one hour. Trifluoroacetic acid (2.3 mL) was added to the reaction solution, then the reaction solution was freeze-dried and purified by reverse-phase silica gel column chromatography (0.05% aqueous trifluoroacetic acid solution/0.05% trifluoroacetic acid-acetonitrile) to give the title compound (Compound ST28, F-Pnaz-MeA3Pyr-pCpA) (64.4 mg, 5%).

LCMS (ESI) m/z=1098.5 (M−H)−

Retention time: 0.39 min (analysis condition SQDFA05_01)

Synthesis of (2S,3S)-2-[[4-[[2-(4-fluorophenyl)acetyl]amino]phenyl]methoxycarbonylamino]-3-methylpentanoic acid (Compound ST29, F-Pnaz-Ile-OH)

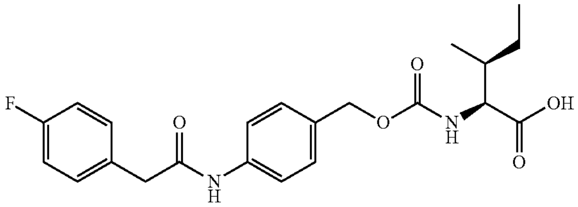 [SMILES: CC[C@H](C)[C@H](NC(=O)OCc1ccc(NC(=O)Cc2ccc(F)cc2)cc1)C(=O)O]

Under a nitrogen atmosphere, DMSO (2 mL) and triethylamine (128 μL, 0.92 mmol) were added at room temperature to a mixture of L-isoleucine (52.5 mg, 0.40 mmol) and (4-nitrophenyl)-4-(2-(4-fluorophenyl)acetamide)benzyl carbonate (178 mg, 0.42 mmol) synthesized by the method described in the patent literature (WO 2018143145 A1). The reaction mixture was stirred at room temperature for 2.5 days, and then purified by reverse-phase silica gel column chromatography (0.1% aqueous formic acid solution/0.1% formic acid-acetonitrile solution) to give (2S,3S)-2-[[4-[[2-(4-fluorophenyl)acetyl]amino]phenyl]methoxycarbonylamino]-3-methylpentanoic acid (Compound ST29, F-Pnaz-Ile-OH) (125 mg, 75%).

LCMS (ESI) m/z=415.4 (M−H)−

Retention time: 0.74 min (analysis condition SQDFA05_02)

Synthesis of cyanomethyl (2S,3S)-2-[[4-[[2-(4-fluorophenyl)acetyl]amino]phenyl]methoxycarbonylamino]-3-methylpentanoate (Compound ST30, F-Pnaz-Ile-$OCH_2CN$)

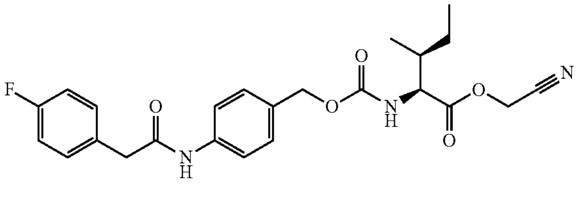 [SMILES: CC[C@H](C)[C@H](NC(=O)OCc1ccc(NC(=O)Cc2ccc(F)cc2)cc1)C(=O)OCC#N]

Under a nitrogen atmosphere, (2S,3S)-2-[[4-[[2-(4-fluorophenyl)acetyl]amino]phenyl]methoxycarbonylamino]-3-methylpentanoic acid (Compound ST29, F-Pnaz-Ile-OH) (42 mg, 0.1 mmol) and 2-bromoacetonitrile (13 μL, 0.200 mmol) were dissolved in acetonitrile (500 μL), N-ethyl-isopropylpropan-2-amine (DIPEA) (35 μL, 0.200 mmol) was added thereto at room temperature, and the mixture was stirred at room temperature for 16 hours. The reaction solution was concentrated to give cyanomethyl (2S,3S)-2-[[4-[[2-(4-fluorophenyl)acetyl]amino]phenyl]methoxycarbonylamino]-3-methylpentanoate (Compound ST30, F-Pnaz-Ile-$OCH_2CN$) as a crude product. The obtained crude product was dissolved in acetonitrile (3.00 mL) and directly used in the next step.

LCMS (ESI) m/z=454 (M−H)−

Retention time: 0.83 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S,3S)-2-[[4-[[2-(4-fluorophenyl)acetyl]amino]phenyl]methoxycarbonylamino]-3-methylpentanoate (Compound ST31, F-Pnaz-Ile-pCpA)

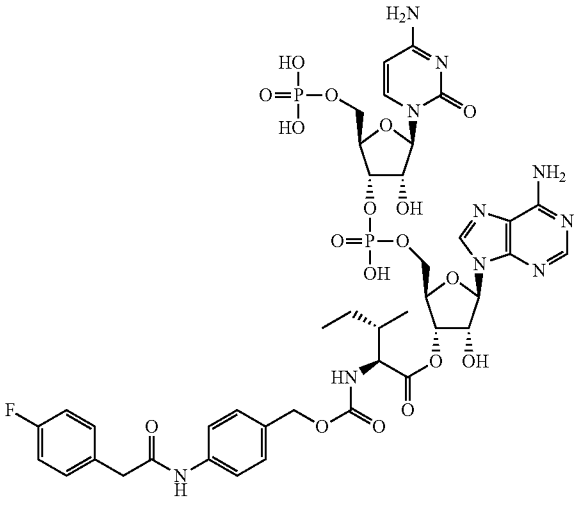 [SMILES: CC[C@H](C)[C@H](NC(=O)OCc1ccc(NC(=O)Cc2ccc(F)cc2)cc1)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]

((2R,3R,4R,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (72.2 mg, 0.100 mmol) synthesized by the method described in the literature (Helv. Chim. Acta, 90, 297-310) was dissolved in Buffer A (60 mL), a solution of cyanomethyl (2S,3S)-2-[[4-[[2-(4-fluorophenyl)acetyl]amino]phenyl]methoxycarbonylamino]-3-methylpentanoate (Compound ST30, F-Pnaz-Ile-$OCH_2CN$) (45.5 mg, 0.100 mmol) in acetonitrile (3.00 mL) was added thereto, and this was stirred at room temperature for 20 hours. The reaction solution was cooled to 0° C., and then trifluoroacetic acid (3.00 mL) was added. The reaction solution was stirred at room temperature for 30 min, and then purified by reverse-phase silica gel column chromatography (0.05% aqueous trifluoroacetic acid solution/0.05% trifluoroacetic acid-acetonitrile) to give the title compound (Compound ST31, F-Pnaz-Ile-pCpA) (12 mg, 11.4%).

LCMS (ESI) m/z=1049.4 (M−H)−

Retention time: 0.54 min (analysis condition SQDFA05_02)

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonyl-methylamino]-3-phenylpropanoate (Compound ST32. F-Pnaz-MePhe-pCpA)

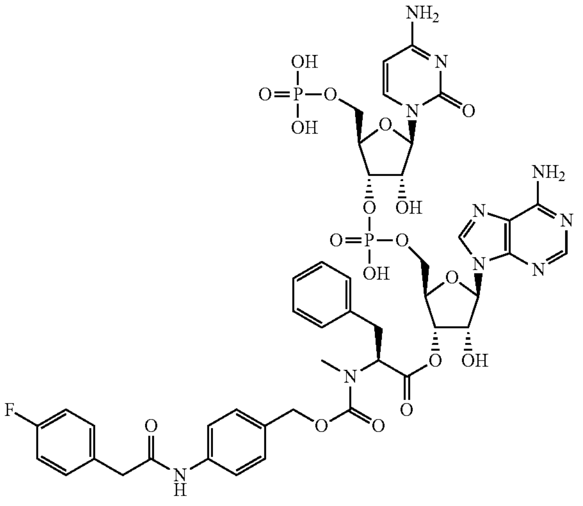 [SMILES: CN(C(=O)OCc1ccc(NC(=O)Cc2ccc(F)cc2)cc1)[C@@H](Cc1ccccc1)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]

This was synthesized by the method described in WO 2018/225864.

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2R)-2-[[4-[[2-(4-fluorophenyl)acetyl]amino]phenyl]methoxycarbonylamino]propanoate (Compound ST33, F-Pnaz-D-Ala-pCpA)
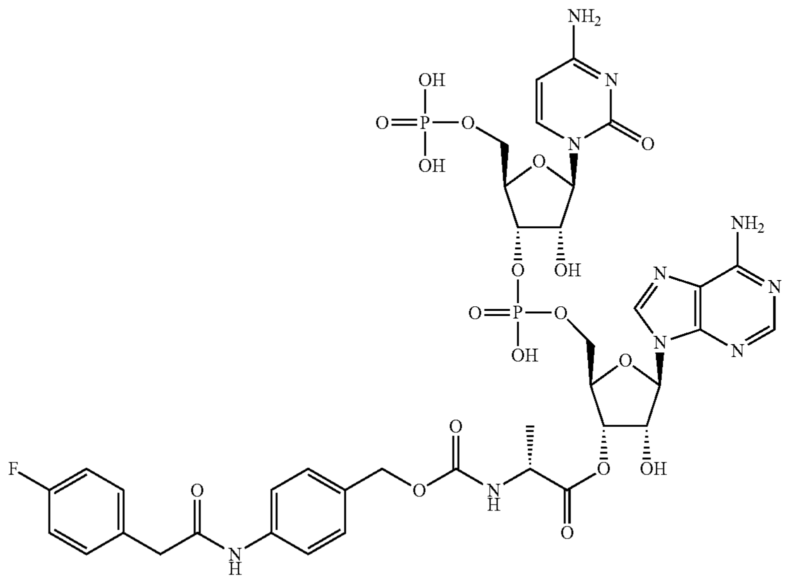 [SMILES: C[C@@H](NC(=O)OCc1ccc(NC(=O)Cc2ccc(F)cc2)cc1)C(=O)O[C@H]1[C@@H](O)[C@H](n2cnc3c(N)ncnc32)O[C@@H]1COP(=O)(O)O[C@H]1[C@@H](O)[C@H](n2ccc(N)nc2=O)O[C@@H]1COP(=O)(O)O]
This was synthesized by the method described in WO 2018/143145.

Synthesis of 2-O-[(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl]-O-[[4-[[2-(4-fluorophenyl)acetyl]amino]phenyl]methyl] (2S)-piperidin-1,2-dicarboxylate (Compound ST34, F-Pnaz-Pic(2)-pCpA)
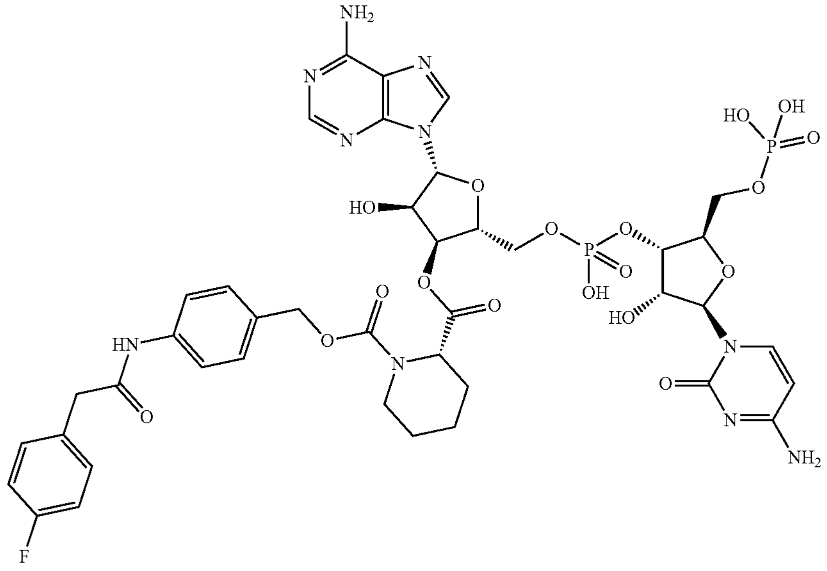 [SMILES: Nc1ccn([C@@H]2O[C@H](COP(=O)(O)O)[C@@H](OP(=O)(O)OC[C@H]3O[C@@H](n4cnc5c(N)ncnc54)[C@H](O)[C@@H]3OC(=O)[C@@H]3CCCCN3C(=O)OCc3ccc(NC(=O)Cc4ccc(F)cc4)cc3)[C@H]2O)c(=O)n1]
This was synthesized by the method described in WO 2020/138336.

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonyl-methylamino]-4-phenylbutanoate (Compound ST35, F-Pnaz-MeHph-pCpA)

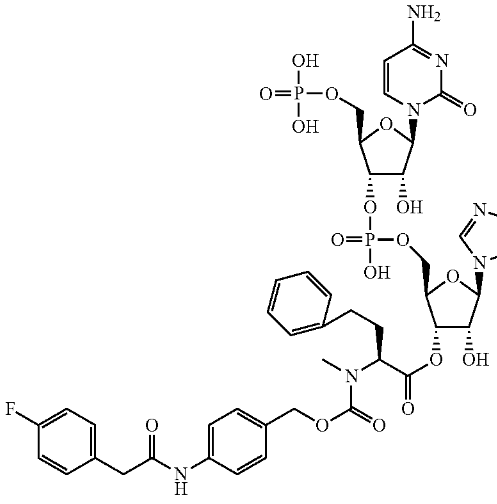

This was synthesized by the method described in the patent literature (WO 2020138336 A1).

Synthesis of [(2R,3S,4R,5R)-2-[[[(2R,3S,4R,5R)-5-(4-amino-2-oxopyrimidin-1-yl)-4-hydroxy-2-(phosphonooxymethyl)oxolan-3-yl]oxy-hydroxy-phosphoryl]oxymethyl]-5-(6-aminopurin-9-yl)-4-hydroxyoxolan-3-yl] (2S)-2-[[4-[[2-(4-fluorophenyl)acetyl]amino]phenyl]methoxycarbonyl-methylamino]-4-phenylbutanoate (Compound ST36, F-Pnaz-SPh2Cl-pCpA)

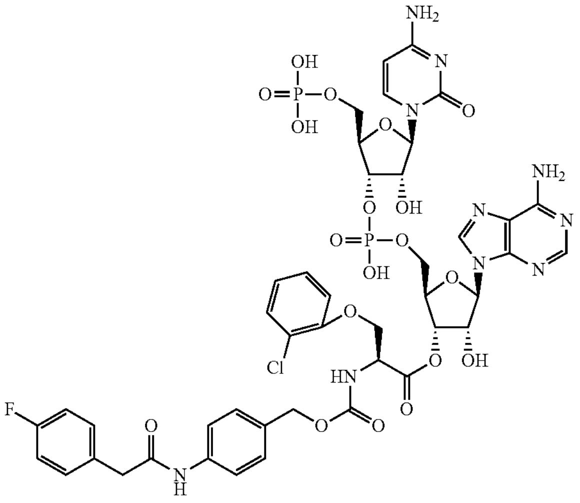 [SMILES: Nc1ccn([C@@H]2O[C@H](COP(=O)(O)O)[C@@H](OP(=O)(O)OC[C@H]3O[C@@H](n4cnc5c(N)ncnc54)[C@H](O)[C@@H]3OC(=O)[C@H](COc3ccccc3Cl)NC(=O)OCc3ccc(NC(=O)Cc4ccc(F)cc4)cc3)[C@H]2O)c(=O)n1]

This was synthesized by the method described in the patent literature (WO 2020138336 A1).

Example 13. Synthesis of Aminoacyl-tRNA

Various aminoacyl-tRNAs were synthesized and recovered according to the method described in "Synthesis of aminoacyl-tRNA using aminoacyl-pCpA: Part 1" of Example 5. The various aminoacyl-tRNAs that were recovered were respectively dissolved in 1 mM sodium acetate. Table 18 shows the correspondence between the names of the prepared aminoacyl-tRNAs and the aminoacyl-pCpA amino acids to be used.

TABLE 18

| Abbreviation of aminoacyl tRNA | Name of pCpA amino acid | Compound No. | Amino acid abbreviation |
|---|---|---|---|
| Nle-tRNAGlu (CUG) | F-Pnaz-Nle-pCpA | ST04 | Nle |
| MeGly-tRNAGlu (CUG) | F-Pnaz-MeG-pCpA | ST23 | MeG |
| MePhe-tRNAGlu (CUG) | F-Pnaz-MePhe-pCpA | ST32 | MePhe |
| S3F5MePyr-tRNAGlu (CUG) | F-Pnaz-S3F5MePyr-pCpA | ST08 | S3F5MePyr |
| Pic (2)-tRNAGlu (CUG) | F-Pnaz-Pic (2)-pCpA | ST34 | Pic (2) |
| MeHph-tRNAGlu (CUG) | F-Pnaz-MeHph-pCpA | ST35 | MeHph |
| MeA3Pyr-tRNAGlu (CUG) | F-Pnaz-MeA3Pyr-pCpA | S T 2 6 | MeA3Pyr |
| SPh2Cl-tRNAGlu (CUG) | F-Pnaz-SPh2Cl-pCpA | ST36 | SPh2CI |
| Gly-tRNAGlu (CUG) | F-Pnaz-Gly-pCpA | ST14 | Gly |
| Ile-tRNAGlu (CUG) | F-Pnaz-Ile-pCpA | S T 3 1 | Ile |
| Pro-tRNAGlu (CUG) | F-Pnaz-Pro-pCpA | S T 1 1 | Pro |
| Thr-tRNAGlu (CUG) | F-Pnaz-Thr-pCpA | S T 1 5 | Thr |
| MeSer (tBuOH)-tRNAGlu (CUG) | Pnaz-MeSer (tBuOH)-pCpA | TS01 | MeSer (tBuOH) |
| D-Ala-tRNAGlu (CUG) | F-Pnaz-D-Ala-pCpA | S T 3 3 | D-Ala |
| Leu-tRNAGlu (CUG) | F-Pnaz-Leu-pCpA | S T 20 | Leu |

Example 14. Production of *E. coli* Strains Expressing the Variants

Eight L31 variant strains (L31(1-27), L31(1-32), L31(1-37), L31(1-42), L31(1-47), L31(1-52), L31(1-57), and L31 (1-67)) that express the L31 protein from the N terminal side in various lengths were constructed. The *E. coli* strains were constructed according to the protocol attached to the Quick and Easy Conditional Knockout Kit (loxP/Cre) (Gene Bridges).

Production of a functional cassette with added homology arms Functional cassettes were constructed according to the method described in Example 1. Table 19 shows the lengths of the L31 expression regions of each of the strains and their corresponding primers used to perform PCR on the functional cassettes used to produce the strains.

TABLE 19

| | L31 expression region | | | | | | | |
|---|---|---|---|---|---|---|---|---|
| | 1-27 | 1-32 | 1-37 | 1-42 | 1-47 | 1-52 | 1-57 | 1-67 |
| SEQ ID NO of forward primer | 18 | 19 | 20 | 21 | 22 | 23 | 24 | 25 |
| SEQ ID NO of reverse primer | 26 | 26 | 26 | 26 | 26 | 26 | 26 | 26 |

Production of L31 Variant Strains

L31 variant strains were produced according to the method described in Example 1.

Example 15. Purification of Ribosomes

Preparation of Ribosomes Using the L31 Variant Strains, the L31short Strain, the L31Intact Strain, AND the W3110 Strain Culturing of the strains, disruption of *E. coli*, purification of *E. coli*, butyl sepharose purification, and ultracentrifugation purification were performed according to the methods described in Example 2. For all the strains, the descriptions relating to the L31intact strain and the L31short strain in Example 2 were followed. For disruption of *E. coli*, the Mg10 Lysis Buffer described in Example 2 was used. A total of 11 ribosomes—the L31short ribosome, the L31intact ribosome, the WT ribosome, and the eight L31 variant ribosomes—were prepared so that their final concentrations were 10 μM to 20 μM.

INDUSTRIAL APPLICABILITY

The present invention provides methods for producing peptides and peptide libraries comprising unnatural amino acids, and engineered L31 proteins and such for use in these methods. Use of the production methods of the present invention enables efficient translation of mRNAs encoding peptides comprising unnatural amino acids, and efficient production of these peptides and libraries comprising them.

The invention claimed is:

1. A method for producing a peptide, comprising a step of translating an mRNA encoding a peptide comprising one or more types of unnatural amino acids in a translation system that comprises a ribosome comprising an engineered L31 protein, wherein the engineered L31 protein is selected from the group consisting of the proteins of (1) to (3) below:

(1) a protein comprising an amino acid sequence with deletion of 6 to 50 amino acid residues from the C terminus in the amino acid sequence set forth in SEQ ID NO: 1;

(2) a protein comprising an amino acid sequence in which 1, 2, 3, 4, or 5 amino acid(s) are inserted, substituted, deleted and/or added compared to the amino acid sequence of the protein of (1); and (3) a protein comprising an amino acid sequence having 95% or more sequence identity to the amino acid sequence of the protein of (1); and wherein the ribosome comprising the protein of (2) and (3) has greater activity for translation of the peptide comprising the unnatural amino acid(s), as compared to the ribosome comprising the wild-type *Escherichia coli* L31 that comprises the amino acid sequence of SEQ ID NO: 1.

2. The method of claim 1, wherein the proportion of ribosomes comprising the engineered L31 protein relative to all ribosomes in the translation system is 50% or more.

3. The method of claim 1, further comprising a step of cyclizing the peptide.

4. The method of claim 1, wherein the peptide comprises an unnatural amino acid at a position corresponding to its initial amino acid.

5. A method of screening for a peptide that binds to a target substance, comprising steps (a) to (c) below:

(a) producing a peptide by the method of claim 1;

(b) contacting a target substance with the peptide or a library comprising the peptides; and (c) selecting a peptide that binds to the target substance.

* * * * *